US008241213B2

(12) United States Patent
Lynn et al.

(10) Patent No.: US 8,241,213 B2
(45) Date of Patent: *Aug. 14, 2012

(54) MICROPROCESSOR SYSTEM FOR THE ANALYSIS OF PHYSIOLOGIC DATASETS

(76) Inventors: Lawrence A. Lynn, Columbus, OH (US); Eric N. Lynn, Villa Ridge, MO (US)

( * ) Notice: Subject to any disclaimer, the term of this patent is extended or adjusted under 35 U.S.C. 154(b) by 55 days.

This patent is subject to a terminal disclaimer.

(21) Appl. No.: 12/839,177

(22) Filed: Jul. 19, 2010

(65) Prior Publication Data
US 2011/0015501 A1    Jan. 20, 2011

Related U.S. Application Data

(63) Continuation of application No. 10/150,842, filed on May 17, 2002, now Pat. No. 7,758,503, and a continuation-in-part of application No. 09/628,655, filed on Jul. 28, 2000, now Pat. No. 6,609,016, and a continuation-in-part of application No. 09/115,226, filed on Jul. 14, 1998, now Pat. No. 6,223,064, and a continuation-in-part of application No. 08/789,460, filed on Jan. 27, 1997, now Pat. No. 5,891,023.

(60) Provisional application No. 60/291,691, filed on May 17, 2001, provisional application No. 60/291,687, filed on May 17, 2001.

(51) Int. Cl.
*A61B 5/00* (2006.01)
*A61B 5/08* (2006.01)
(52) U.S. Cl. .......................... 600/301; 600/323; 600/529
(58) Field of Classification Search ........................ None
See application file for complete search history.

(56) References Cited

U.S. PATENT DOCUMENTS 4,106,503 A    8/1978    Rosenthal et al.
(Continued)

FOREIGN PATENT DOCUMENTS

DE    9200422    7/1992
(Continued)

OTHER PUBLICATIONS

"Critical Alarms and Patient Safety: ECRI's guide to developing effective alarm strategies and responding to JCAHO's alarm-safety goal," Health Devices (no author listed), Nov. 2002, vol. 31, No. 11, pp. 397-417.

(Continued)

*Primary Examiner* — Sam Yao
*Assistant Examiner* — Shirley Jian
(74) *Attorney, Agent, or Firm* — International IP Law Group, PLLC

(57) ABSTRACT

A system and method for organization and analysis of complex and dynamically interactive time series is disclosed. One example comprises a processor based system for relational analysis of physiologic signals for providing early recognition of catastrophic and pathologic events such as pathophysiologic divergence. The processor is programmed to identify pathophysiologic divergence of at least one of first and second physiologic parameters in relationship to the other and to output an indication of the divergence. An object-based method of iterative relational processing waveform fragments in the time domain is described wherein each more complex waveform object inherits the characteristics of the waveform objects from which it is derived. The first physiologic parameter can be the amplitude and frequency of the variation in chest wall impedance or nasal pressure and the second parameter can be a measure or indication of the arterial oxygen saturation.

18 Claims, 23 Drawing Sheets

U.S. PATENT DOCUMENTS

| | | | |
|---|---|---|---|
| 4,365,636 A | 12/1982 | Barker | |
| 4,523,279 A | 6/1985 | Sperinde et al. | |
| 4,630,614 A | 12/1986 | Atlas | |
| 4,651,746 A | 3/1987 | Wall | |
| 4,738,266 A | 4/1988 | Thatcher | |
| 4,757,824 A | 7/1988 | Chaumet | |
| 4,765,340 A | 8/1988 | Sakai et al. | |
| 4,802,485 A | 2/1989 | Bowers et al. | |
| 4,869,253 A | 9/1989 | Craig, Jr. et al. | |
| 5,123,420 A | 6/1992 | Paret | |
| 5,134,995 A | 8/1992 | Gruenke et al. | |
| 5,199,424 A | 4/1993 | Sullivan et al. | |
| 5,206,807 A | 4/1993 | Hatke et al. | |
| 5,218,962 A | 6/1993 | Mannheimer et al. | |
| 5,233,983 A | 8/1993 | Markowitz | |
| 5,275,159 A | 1/1994 | Griebel | |
| 5,303,699 A | 4/1994 | Bonassa et al. | |
| 5,312,454 A | 5/1994 | Roline et al. | |
| 5,318,597 A | 6/1994 | Hauck et al. | |
| 5,329,931 A | 7/1994 | Clauson et al. | |
| 5,335,654 A | 8/1994 | Rapoport | |
| 5,353,788 A | 10/1994 | Miles | |
| 5,355,880 A | 10/1994 | Thomas et al. | |
| 5,368,026 A | 11/1994 | Swedlow et al. | |
| 5,385,144 A | 1/1995 | Yamanishi et al. | |
| 5,398,682 A * | 3/1995 | Lynn | 600/335 |
| 5,483,969 A | 1/1996 | Testerman et al. | |
| 5,485,851 A | 1/1996 | Erickson | |
| 5,490,502 A | 2/1996 | Rapoport et al. | |
| 5,535,739 A | 7/1996 | Rapoport et al. | |
| 5,540,733 A | 7/1996 | Testerman et al. | |
| 5,549,106 A | 8/1996 | Gruenke et al. | |
| 5,551,419 A | 9/1996 | Froehlich et al. | |
| 5,605,151 A * | 2/1997 | Lynn | 600/323 |
| 5,632,270 A | 5/1997 | O'Mahony et al. | |
| 5,645,053 A | 7/1997 | Remmers et al. | |
| 5,645,054 A | 7/1997 | Cotner et al. | |
| 5,682,878 A | 11/1997 | Ogden | |
| 5,704,345 A | 1/1998 | Berthon-Jones | |
| 5,730,144 A | 3/1998 | Katz et al. | |
| 5,740,795 A | 4/1998 | Brydon | |
| 5,743,250 A | 4/1998 | Gonda et al. | |
| 5,749,900 A | 5/1998 | Schroeppel et al. | |
| 5,751,911 A | 5/1998 | Goldman | |
| 5,765,563 A | 6/1998 | Vander Schaaf | |
| 5,769,084 A | 6/1998 | Katz et al. | |
| 5,782,240 A | 7/1998 | Raviv et al. | |
| 5,794,614 A | 8/1998 | Gruenke et al. | |
| 5,794,615 A | 8/1998 | Estes | |
| 5,803,065 A | 9/1998 | Zdrojkowski et al. | |
| 5,803,066 A | 9/1998 | Rapoport et al. | |
| 5,823,187 A | 10/1998 | Estes et al. | |
| 5,827,179 A | 10/1998 | Lichter et al. | |
| 5,830,135 A | 11/1998 | Bosque et al. | |
| 5,845,636 A | 12/1998 | Gruenke et al. | |
| 5,853,364 A | 12/1998 | Baker, Jr. et al. | |
| 5,865,173 A | 2/1999 | Froehlich | |
| 5,865,736 A | 2/1999 | Baker, Jr. et al. | |
| 5,891,022 A | 4/1999 | Pologe | |
| 5,891,023 A | 4/1999 | Lynn | |
| 5,902,250 A | 5/1999 | Verrier et al. | |
| 5,957,885 A | 9/1999 | Bollish et al. | |
| 6,006,379 A | 12/1999 | Hensley | |
| 6,015,388 A | 1/2000 | Sackner et al. | |
| 6,083,156 A | 7/2000 | Lisiecki | |
| 6,105,575 A | 8/2000 | Estes et al. | |
| 6,120,441 A | 9/2000 | Griebel | |
| 6,138,675 A | 10/2000 | Berthon-Jones | |
| 6,144,877 A | 11/2000 | DePetrillo | |
| 6,148,814 A | 11/2000 | Clemmer et al. | |
| 6,171,258 B1 | 1/2001 | Karakasoglu et al. | |
| 6,190,324 B1 | 2/2001 | Kieval et al. | |
| 6,215,403 B1 | 4/2001 | Chan et al. | |
| 6,216,032 B1 | 4/2001 | Griffin et al. | |
| 6,223,064 B1 | 4/2001 | Lynn et al. | |
| 6,286,508 B1 | 9/2001 | Remmers et al. | |
| 6,299,581 B1 | 10/2001 | Rapoport et al. | |
| 6,305,374 B1 | 10/2001 | Zdrojkowski et al. | |
| 6,342,039 B1 | 1/2002 | Lynn et al. | |
| 6,345,619 B1 | 2/2002 | Finn | |
| 6,367,474 B1 | 4/2002 | Berthon-Jones et al. | |
| 6,371,113 B1 | 4/2002 | Tobia et al. | |
| 6,371,114 B1 | 4/2002 | Schmidt et al. | |
| 6,375,623 B1 | 4/2002 | Gavriely | |
| 6,397,092 B1 | 5/2002 | Norris et al. | |
| 6,398,727 B1 | 6/2002 | Bui et al. | |
| 6,401,713 B1 | 6/2002 | Hill et al. | |
| 6,415,166 B1 | 7/2002 | Van Hoy et al. | |
| 6,425,861 B1 | 7/2002 | Haberland et al. | |
| 6,449,501 B1 | 9/2002 | Reuss | |
| 6,463,326 B1 | 10/2002 | Hartley et al. | |
| 6,488,634 B1 | 12/2002 | Rapoport et al. | |
| 6,502,572 B1 | 1/2003 | Berthon-Jones et al. | |
| 6,519,486 B1 | 2/2003 | Edgar, Jr. et al. | |
| 6,529,752 B2 | 3/2003 | Krausman et al. | |
| 6,532,960 B1 | 3/2003 | Yurko | |
| 6,539,940 B2 | 4/2003 | Zdrojkowski et al. | |
| 6,572,557 B2 | 6/2003 | Tchou et al. | |
| 6,579,242 B2 | 6/2003 | Bui et al. | |
| 6,609,016 B1 | 8/2003 | Lynn | |
| 6,609,517 B1 | 8/2003 | Estes et al. | |
| 6,622,726 B1 | 9/2003 | Du | |
| 6,637,434 B2 | 10/2003 | Noble | |
| 6,640,806 B2 | 11/2003 | Yurko | |
| 6,641,542 B2 | 11/2003 | Cho et al. | |
| 6,661,161 B1 | 12/2003 | Lanzo et al. | |
| 6,675,797 B1 | 1/2004 | Berthon-Jones | |
| 6,691,705 B2 | 2/2004 | Dittmann et al. | |
| 6,745,764 B2 | 6/2004 | Hickle | |
| 6,748,252 B2 | 6/2004 | Lynn et al. | |
| 6,752,150 B1 * | 6/2004 | Remmers et al. | 128/204.18 |
| 6,760,608 B2 * | 7/2004 | Lynn | 600/324 |
| 6,761,167 B1 | 7/2004 | Nadjafizadeh et al. | |
| 6,804,656 B1 | 10/2004 | Rosenfeld et al. | |
| 6,807,965 B1 | 10/2004 | Hickle | |
| 6,814,074 B1 | 11/2004 | Nadjafizadeh et al. | |
| 6,817,361 B2 | 11/2004 | Berthon-Jones et al. | |
| 6,822,564 B2 | 11/2004 | Al-Ali | |
| 6,830,549 B2 | 12/2004 | Bui et al. | |
| 6,832,200 B2 | 12/2004 | Greeven et al. | |
| 6,896,660 B2 | 5/2005 | Jelliffe et al. | |
| 6,928,370 B2 | 8/2005 | Anuzis et al. | |
| 6,932,084 B2 | 8/2005 | Estes et al. | |
| 6,948,497 B2 | 9/2005 | Zdrojkowski et al. | |
| 6,985,762 B2 | 1/2006 | Brashears et al. | |
| 6,988,498 B2 | 1/2006 | Berthon-Jones et al. | |
| 7,040,315 B1 | 5/2006 | Stromberg | |
| 7,081,095 B2 | 7/2006 | Lynn et al. | |
| 7,153,263 B2 | 12/2006 | Carter et al. | |
| 7,161,484 B2 | 1/2007 | Tsoukalis | |
| 7,220,220 B2 | 5/2007 | Stubbs et al. | |
| 7,225,013 B2 | 5/2007 | Geva et al. | |
| 7,230,529 B2 | 6/2007 | Ketcherside et al. | |
| 7,297,119 B2 | 11/2007 | Westbrook et al. | |
| 7,355,512 B1 | 4/2008 | Al-Ali | |
| 7,370,650 B2 | 5/2008 | Nadjafizadeh et al. | |
| 7,398,115 B2 | 7/2008 | Lynn | |
| 7,539,537 B2 | 5/2009 | Hickle | |
| 7,640,055 B2 | 12/2009 | Geva et al. | |
| 7,647,185 B2 | 1/2010 | Tarassenko et al. | |
| 7,725,146 B2 | 5/2010 | Li et al. | |
| 7,758,503 B2 * | 7/2010 | Lynn et al. | 600/300 |
| 2001/0018557 A1 * | 8/2001 | Lynn et al. | 600/324 |
| 2001/0037067 A1 * | 11/2001 | Tchou et al. | 600/483 |
| 2002/0082488 A1 | 6/2002 | Al-Ali et al. | |
| 2002/0095090 A1 | 7/2002 | Caro et al. | |
| 2002/0117173 A1 | 8/2002 | Lynn et al. | |
| 2002/0138014 A1 | 9/2002 | Baura et al. | |
| 2002/0165462 A1 * | 11/2002 | Westbrook et al. | 600/529 |
| 2002/0190863 A1 | 12/2002 | Lynn | |
| 2004/0163648 A1 | 8/2004 | Burton | |
| 2005/0016536 A1 | 1/2005 | Rapoport et al. | |
| 2006/0149144 A1 | 7/2006 | Lynn | |
| 2006/0155206 A1 | 7/2006 | Lynn | |
| 2006/0155207 A1 | 7/2006 | Lynn et al. | |
| 2006/0161071 A1 | 7/2006 | Lynn et al. | |
| 2006/0189880 A1 | 8/2006 | Lynn et al. | |

| | | | |
|---|---|---|---|
| 2006/0235324 | A1 | 10/2006 | Lynn |
| 2007/0093721 | A1 | 4/2007 | Lynn et al. |
| 2007/0149860 | A1 | 6/2007 | Lynn et al. |
| 2008/0091088 | A1 | 4/2008 | Kiani |
| 2008/0200824 | A1 | 8/2008 | Kane et al. |
| 2008/0287756 | A1 | 11/2008 | Lynn |
| 2008/0300471 | A1 | 12/2008 | Al-Ali et al. |
| 2009/0177493 | A1 | 7/2009 | Narayan |
| 2010/0026510 | A1 | 2/2010 | Kiani et al. |
| 2010/0079292 | A1 | 4/2010 | Lynn et al. |
| 2010/0088346 | A1 | 4/2010 | Urness et al. |
| 2010/0113909 | A1 | 5/2010 | Batchelder et al. |
| 2010/0234705 | A1 | 9/2010 | Lynn |

FOREIGN PATENT DOCUMENTS

| | | |
|---|---|---|
| EP | 0459284 | 12/1991 |
| EP | 0651971 | 5/1995 |
| EP | 0700690 | 3/1996 |
| EP | 0709107 | 5/1996 |
| EP | 0714670 | 6/1996 |
| EP | 0722747 | 7/1996 |
| EP | 0759791 | 3/1997 |
| EP | 0788805 | 8/1997 |
| EP | 0875258 | 11/1998 |
| EP | 0934723 | 8/1999 |
| EP | 0968734 | 1/2000 |
| EP | 1004325 | 5/2000 |
| EP | 1172123 | 1/2002 |
| EP | 1488743 | 12/2004 |
| WO | WO 88/01149 | 2/1988 |
| WO | WO 90/09146 | 8/1990 |
| WO | WO 90/14121 | 11/1990 |
| WO | WO 92/11054 | 7/1992 |
| WO | WO 92/22244 | 12/1992 |
| WO | WO 94/06499 | 3/1994 |
| WO | WO 94/23780 | 10/1994 |
| WO | WO 95/32016 | 11/1995 |
| WO | WO 97/14462 | 4/1997 |
| WO | WO 97/28838 | 8/1997 |
| WO | WO 99/24099 | 5/1999 |
| WO | WO 99/45989 | 9/1999 |
| WO | WO 00/67827 | 11/2000 |
| WO | WO 2004/047621 | 6/2004 |
| WO | WO 2005/065757 | 7/2005 |

OTHER PUBLICATIONS

Aboyans, et al., "Sleep Apnoea Syndrome and the Extent of Atherosclerotic Lesions in Middle-Aged Men with Myocardial Infarction," International Angiology, Mar. 1999, vol. 18, No. 1, pp. 7073.

Abraham et al., "Sequential Cardiorespiratory Patterns in Septic Shock," Critical Care Medicine, Oct. 1983, vol. 11, No. 10, pp. 799-803.

Agilent Technologies, Agilent M1165/66/67/75/76/77A Component Monitoring System & Agilent M1205a V24 and V26 User's Reference Manual, vol. 2, Parameter Information, Part No. M1046-9101L, First Ed., Printed Nov. 2000.

Agilent Technologies, Agilent M1165/66/67/75/76/77A Component Monitoring System and Agilent M1205A V24 & V26, User's Reference Manual, vol. 1, System Information, Part No. M106-9101L, First Ed., Printed Nov. 2000.

Aittokallio et al., "Analysis of Inspiratory Flow Shapes in Patients with Partial Upper Airway Obstruction During Sleep," Chest, Jan. 2001, vol. 119, No. 1, pp. 37-44.

Alaris System, Brochure, "Medication Safety System Focused at the Point of Care," Cardinal Health, Alaris Products, pp. 8.

Alchanatis et al., "Left ventricular function in patients with obstnlctive sleep apnoea syndrome before and after treatment with nasal continuous positive airway pressure," Respiration, 2000, vol. 67, No. 4, p. 367, (Abstract).

Andreas et al., "Prevalence of Obstructive Sleep Apnoea in Patients with Coronary Artery Disease," Coronary Artery Disease, Jul. 1996, vol. 7, No. 7, pp. 541-545.

Attin et al. "An educational project to improve knowledge related to pulse oximetry," American Journal of Critical Care, 2002, vol. 11, No. 6, pp. 529-534.

Aubry et al., "The SaO.sub.2/t Diagram as a Useful Means to Express Nocturnal Hypoxemia," Chest, 1989, vol. 96, pp. 1341-1345.

Author Unknown, "Background of Oximetry Utilization for Sleep Apnea Diagnosis," Publication information unknown, Undated.

Author Unknown, "Chapter IV Oxygen Consumption During ADO," Introduction, pp. 40-46, Book Title Unknown, Date Unknown.

Author Unknown, "Chapter X Effects of a 6-minute Period of ADO," Introduction, pp. 108-113, Book Title Unknown, Date Unknown.

Author Unknown, "Excessive Daytime Sleepiness," News Bulletin, http://www.websciences.org/nsf/pressarchives/leadpressrelease_g.html, Jun. 3, 1997, Washington, DC, USA.

Author Unknown, "Sleep Apnea & Heart Problems," News Channel WTVC, Chattanooga, Tennessee, USA, Jun. 3, 1999, News Bulletin.

Author Unknown, "The Physiologic Parameters Defining the Oximetry Waveform Patterns in Sleep Apnea, "Undated, Publication Unknown.

Author Unknown, "The Ventilation Instability Detection Trial," Hospital Protocol, Early Discussion Draft, 4 pages, Facsimile dated Jul. 23, 2003, from SDC.

Author Unknown, 1998 "New Survey Reports More Than 168 Million American Adults Fail Sleep IQ Test," 132 Million Suffer Sleep Problems, Life Magazine, Feb. 1998.

Author Unknown, News Bulletin, "Lack of sleep America's top health problem, doctors say," Health Story Page, CNN, htto://cnn.com/HEALTH/9703/17/nfm/sleep.deprivation/index.html, Mar. 17, 1997.

Ayas et al., "Unrecognized Severe Postoperative Hypercapnia: A Case of Apneic Oxygenation," Case Report, Mayo Clinic Proceedings, 1998, vol. 73, pp. 51-54, Minneapolis, Minnesota, USA.

Badoual et al., "Sleep Apnoea Syndrome and Cardiac Failure," Arch Mal Coeur Vaiss., Mar. 2005, vol. 98, No. 3, pp. 198-202, [Article in French] (Abstract).

Bahammam, "Comparison of nasal prong pressure and thermistor measurements for detecting respiratory events during sleep," Respiration, Jul.-Aug. 2004, vol. 71, No. 4, pp. 385-390 (Abstract).

Baker et al., "Nellcor 04 Algorithm Summary," Copyright 1999 Mallinckrodt Inc., pp. 1-8.

Ball et al., "Diagnosis and Treatment of Sleep Apnea Within the Community," The Walla Walla Project, Arch Intern Med, vol. 157, Feb. 24, 1997, pp. 419-424.

Barach et al., "The Physiologic Action of Oxygen and Carbon Dioxide on the Coronary Circulation, as Shown by Blood Gas and Electrocardiographic Studies," The American Heart Journal, Received for publication Aug. 14, 1940, pp. 13-38.

Barker, "The Effects of Motion on the Performance of Pulse Oximeters in Volunteers" (Revised Publication), Anesthesiology, Lippincott-Raven Publishers, American Society of Anesthesiologists, Inc.(Revised Publication) 1997, vol. 86,pp. 101-108 (Both paper and Abstract).

Barnum et al., "Novel Pulse Oximetry Technology Capable of Reliable Bradycardia Monitoring in the Neonate," Respiratory Care, 1997, vol. 42, No. 11, p. 1072 (Abstract).

Bartolo et al., "An Arrhythmia Detector and Heart Rate Estimator for Overnight Polysomnography Studies," conditionally accepted for IEEE Transactions, 19 pages.

Bassetti, Sleep and Stroke, Seminars in Neurology, vol. 25, No. 1, Nov. 1, 2005, pp. 19-32.

Benumof, "Creation of Observational Unit May Decrease Sleep Apnea Risk," Letters to the Editor, Anesthesia Patient Safety Foundation Newsletter and posted on the Malpractice company's web site, The Doctors Company—Sleep Apnea and Narcotic Postoperative Pain . . . http://www.thedoctors.com/risk/bulletins/sleepapnea.asp.

Berg et al., "Continuous Intrathoracic Pressure Monitoring with a New Eiophageal Microchip Catheter in Sleep-Related Upper Airway Obstructions," The Journal of Otolaryngology, vol. 24, No. 3, 1993, pp. 160-164.

Bernet-Buettiker et al., "Evaluation of New Combined Transcutaneous Measurement of PCO2/Pulse Oximetry Oxygen Saturation Ear Sensor in Newborn Patients," Dec. 15, 2004, DOI: IO.1542/peds.2004-0946, Pediatrics Official Journal of the American Academy of Pediatrics, published online, pp. e-64-e68, Elk Grove Village, IL 60007, USA.

Berry et al., "Comparison of Respiratory Event Detection by a Polyvinylidene Fluoride Film Airflow Sensor and a Pneumotachograph in Sleep Apnea Patients," Chest, The Cardiopulmonary and Critical Care Journal, Chest, Sep. 2005, vol. 128(3), pp. 1331-1338.
Berry, "Positive Nasal Airway Pressure Eliminates Snoring as Well as Obstructive Sleep Apnea," Chest, vol. 85, No. 1, Jan. 1984, pp. 15-20.
Berthon-Jones et al., "Time Course of Change in Ventilatory Response to CO2 with Long-Tenn CPAP Therapy for Obstructive Sleep Apnea," American Review Respiratory Disease, 1987, vol. 135, pp. 144-147.
Berthon-Jones, "Feasibility of a Self-Setting CPAP Machine, Sleep," vol. 16, pp. S120-S123,1993.
Bixler et al., "Effects of age on sleep apnea in men: I. Prevalence and Severity," American Journal of Respiratory & Clinical Care Medicine, vol. 157, No. 1, pp. 144-148, Jan. 1998 (Abstract).
Blackshear et al., "Nocturnal Dyspnea and Atrial Fibrillation Preset Cheyne-Stokes Respirations in Patients With Congestive Heart Failure," Arch Intern Med., Jun. 26, 1995, vol. 155, pp. 1296-1302.
Blankfield et al., "Bilateral leg edema, obesity, pulmonary hypertenson, and obstructive sleep apnea," Arch Intern Med., Aug. 14, 2000, vol. 28,160(15), pp. 2357-2362 (Abstract).
Blankfield et al., "Bilateral leg edema, pulmonary hypertension, and obstructive sleep apnea: a cross-sectional study," Family Practice, Jun. 2002, vol. 51, No. 6, pp. 561-564 (Abstract).
Block et al., "Sleep Apnea, Hypopnea and Oxygen Desaturation in Normal Subjects, A Strong Male Predominance," The New England Journal of Medicine, vol. 300, Mar. 8, 1979, pp. 513-517.
Blumen et al., "Dilator muscles of the pharynx and their implication in the sleep apnea syndrome of obstructive type," Review of the literature., [Article in French], Ann Otolaryngol Chir Cervicofac, May 1998, p. 115 (Abstract).
Bock et al., "The Oxygen and Carbon Dioxide Dissociation Curves of Human Blood" (This is study No. 37 of a series of studies on the physiology and pathology of blood form the Harvard Medical School and allied Hospitals, a part of the expense of which has been defrayed by the Proctor Fund for the study of chronic disease, Journal of Biologic Chemistry, vol. 29, 1924, pp. 353-377.
Bohnhorst et al., "Major Reduction in Alarm Frequency With a New Pulse Oximeter," Intensive Care Medicine, 1998, vol. 24, No. 3, pp. 277-278 (Abstract).
Bordier et al., "Death during polysomnography of a patient with cheyn-stokes respiration, respiratory acidosis, and chronic heart failure," Chest, Nov. 2004, vol. 126, No. 5, pp. 1698-1700 (Abstract).
Botelho et al., "Adult Chiari Malformation and Sleep Apnoea," Published online May 21, 2005, Neurosurgeon Review, vol. 28, pp. 169-176, 2005.
Boushra, "Anaesthetic management of patients with sleep apnoea syndrome," Canadian Journal Anaesth, Jun. 1996, vol. 45, No. 6, pp. 599-616 (Abstract).
Bowton et al., "The Incidence and Effect on Outcome of Hypoxemia in Hospitalized Medical Patients," The American Journal of Medicine, vol. 97, Jul. 1994, pp. 38-46.
Bradley et al., "Daytime Hypercapnia in the Development of Nocturnal Hypoxemia in COPD," Chest, vol. 97, No. 2, Feb. 1990, pp. 308-312.
Brooks et al., "Adenoid size is related to severity but not the number of episodes of obstructive apnea in children," Journal of Pediatrics, vol. 132, No. 4, pp. 682-686, Apr. 1998 (Abstract).
Broughton et al., "Practice Parameters for the Use of Stimulants in the Treatment of Narcolepsy," ASDA Standards of Practice, Sleep, vol. 17, No. 4, pp. 348-351, American Sleep Disorders Association and Sleep Research Society 1994.
Brown et al., "Screening for obstructive sleep apnea in stroke patients: a cost-effectiveness analysis," Stroke, Jun. 2005, pp. 1291-1293, Epub May 12, 2005 (Abstract).
Brown, "Dephlogisticated air" revisited: oxygen treatment for central sleep apnea, 1997 American College of Chest Physician, Physician Information, No. 8, Rev. 01, Nov. 1997.
Buckle et al., "Polysomnography in Acutely Ill Intensive Care Unit Patients," Chest, Jul. 1992, vol. 102(1) p. 288(4), American College of Chest Physicians.

Burk et al., "Auto-CPAP in the Treatment of Obstructive Sleep Apnea: A New Approach," Sleep Research, 1992, vol. 21, p. 182, Abstract.
Cain, "Breaking Point of Two Breath Holds Separated by a Single Inspiration," Journal of Appl. Physiol., Jul. 1957, vol. 11(1), pp. 87-90.
Campos-Rodriguez et al., "Mortality in Obstructive Sleep Apnea-Hypopnea Patients Treated With Positive airway Pressure," Chest, The Cardiopulmonary and Critical Care Journal, 2005, vol. 128, pp. 624-633, Northbrook, Illinois, USA (plus Abstract).
Cannesson et al., "Relation between respiratory variations in pulse oximetry plethsmographic waveform amplitude and arterial pulse pressure in ventilated patients," Critical Care 2005, vol. 9, #5, pp. R562-R568, Available online http://ccforum.com/content/9/5/R562.
Chaoquat et al., "Association of Chronic Obstructive Pulmonary Disease and Sleep Apnea Syndrome," American Journal Respiratory Critical Care Medicine, 1995, vol. 151, pp. 82-86.
Cherniack et al., "Periodic Breathing During Sleep," pp. 158-190, New Jersey Medical School, Dean's Office, ID 9739727104, May 26, 1999, 14:23, No. 010, (first page missing).
Cherniack, "New mechanisms for the cardiovascular effects of sleep apnea," American Journal Medicine, Nov. 1, 2000, vol. 109, No. 7, pp. 592-594 (Abstract).
Cherniack, "Introduction to Session on the Pathophysiology of Breathing Control and Breathing: Awake and Asleep, Modeling and Control of Ventilation," Plenum Press, New York, USA, 1995, pp. 87-88.
Cherniack, "Oxygen Sensing: applications in humans, Highlighted Topic: Oxygen Sensing in Health and Disease," Journal Appl. Physiol., vol. 96, pp. 352-358, 2004, The American Physiological Society, htto://www.jap.org.
Christiansen et al., "Carbon Dioxide in Blood," pp. 266-271, Proceedings of the Physiological Society, This Journal, XLVII, p. ii, 1913, pp. 266-271.
Cilli et al., "Nocturnal Oxygen Desaturation in Coronary Artery Disease," JPN Heart Journal, Jan. 1999, pp. 23-28.
CNS Poly G, Printout Examples, CNS, Inc., Chanhassen, Minnesota, USA, Undated, Test Date Feb. 10, 1992.
Conte et al., "Acute cardiovascular diseases and respiratory sleep disorders," Minerva Cardioangiol, Jun. 1999, vol. 47(6), pp. 195-202 (Abstract).
Cooper et al., "Value of Nocturnal Oxygen Saturation as a Screening Test for Sleep Apnoea," Thorax, 1991, vol. 46, pp. 586-588.
Coppola et al., "Management of Obstructive Sleep Apnea Syndrome in the Home, The Role of Portable Sleep Apnea Recording," Chest, vol. 104, No. 1, Jul. 1993, pp. 19-24, Northbrook, IL, USA.
Coy, "Sleep Apnoea and Sympathetic Nervous System Activity: A Review," Journal Slep Res., 1996, No. 5, pp. 42-50, European Sleep Research Society.
Daley, "Beware of All Sedatives in Patients With Sleep Apnea," Anesthesia Patient Safety Foundation Newsletter and posted on the Malpractice company's web site, The Doctors Company—Sleep Apnea and Narcotic Postoperative Pain . . . http://www.thedoctors.com/risk/bulletins/sleepapnea.asp.
Decker et al., "Ambulatory Monitoring of Arterial Oxygen Saturation, Chest," vol. 95, No. 4, Apr. 1989, pp. 717-722, Northbrook, Illinois, USA.
Deegan et al., "Predictive Value of Clinical FeatUres for the Obstructive Sleep Apnoea Syndrome," European Respiratory Journal, vol. 9, pp. 117-124, 1996.
DeLeeuw, "On sleep and death: cardiovascular risk the obstructive sleep apnea syndrome," Neth Journal Medicine, May 1999, vol. 54, No. 5, pp. 188-190 (Abstract).
Dement, Chairman, National Commission on Sleep Disorders Research, "Wake Up America: A National Sleep Alert, vol. 1, Executive Summary and Executive Report, Report of the National Commission on Sleep Disorders Research," Submitted to the United States Congress and to the Secretary, u.s. department of Health and Human Services, Jan. 1993, pp. 1-76.
Demeter et al., "The relationship between gastroesophageal reflex disease and obstructive sleep apnea," Gastroenterology, Sep. 2004, vol. 39, No. 9, pp. 815-820 (Abstract).

Dempsey et al., "Sleep and Breathing State of the Art Review Sleep-Induced Breathing Instability," Sleep, vol. 19, No. 3, pp. 236-247, American Sleep Disorders Association and Sleep Research Society.

Den Herder et al., "Risks of general anaesthesia in people with obstructive sleep apnea," BMJ, vol. 329, Oct. 23, 2004, pp. 955-959, Downloaded from bmj.com.

Dhonneur et al., "Postoperative Obstructive Apnea," Anesth Analg., Sep. 1999, vol. 89, No. 3, pp. 762-767 (Abstract).

Doherty et al., "Long-term effects of nasal continuous positive airway pressure therapy on cardiovascular outcomes in sleep apnea syndrome," Chest, Jun. 2005, vol. 127, No. 6, pp. 2076-2084 (Abstract).

Douglass et al., "The Sleep Disorders Questionnaire I: Creation and Multivariate Structure of SDQ, Clinical Research," Sleep, vol. 17, No. 1, pp. 160-167, 1994 American Sleep Disorders Association and Sleep Research Society.

Douglass et al., "The Sleep Disorders Questionnaire. I: Creation and multivariate structure of SDO," Sleep, Mar. 1994, vol. 17, No. 2, pp. 160-167 (Abstract).

Dowdell et al., "Respiration Presenting as Sleep Apnea Syndrome, Clinical Polysomnographic Features," Am Rev Respir Dis, Apr. 1990, pp. 871-879.

Downs, "Has Oxygen Administration Delayed Appropriate Respiratory Care? Fallacies Regarding Oxygen Therapy," Respiratory Care, Jun. 2003, vol. 48, No. 6.

Downs, "Is Supplemental Oxygen Necessary," Journal of Cardiothoracic and Vascular Anesthesia, vol. 20, No. 2, Apr. 2006.

Dumas et al., "Clinical Evaluation of a Prototype Motion Artifact Resistant Pulse Oximeter in the Recovery Room," Anesth Analg 1996, vol. 83, pp. 269-272.

Dursunoglu et al., "Impact of obstructive sleep apnoea on left ventricular mass and global function," European Respiratory Journal, Aug. 2005, vol. 26, No. 2, pp. 283-288 (Abstract).

Dyken et al, "Obstructive Sleep Apnea Associated with Cerebral Hypoxemia and Death," Neurology, 2004, vol. 62, pp. 491-493.

Dziewas et al., "Capnography screening for sleep apnea in patients with acute stroke," Neurology Res. Jan. 2005, vol. 27, No. 1, pp. 83-87 (Abstract).

Dziewas et al., "Increased Prevalence of Sleep Apnea in Patients with Recurring Ischemic stroke Compared with First Stroke Victims," Journal Neurology, Nov. 2005, vol. 252, No. 11, pp. 1394-1398. Epub Jul. 20, 2005 (Abstract).

Edge City Hospital Sleep Disorders Center, "Sleep Summary of Patient," Houston, Texas, USA, pp. 1-3, Feb. 17, 1997.

Eihefnawy et al., "Stability Analysis of C02 Control of Ventilation," Journal of Internal Medicine, 0161-7567/90, pp. 498-503, Publisher: The American Physiological Society, 1990.

Elfadel et al., "Motion-Resistant Pulse Oximetry," Abstract Only, Journal of Clinical Monitoring, vol. II, No. 4, Jul. 1995, p. 262.

Epstein et al., "Cost-Effectiveness Analysis of Nocturnal Oximetry as a Method of Screening for Sleep Apnea-Hypopnea Syndrome," Jan. 1, 1998, Chest, vol. 113, p. 97-103.

Escourrou et al., "Heart failure and sleep respiratory disorders. Prevalence, physiopathology and treatment," [Article in French], Rev Mal Respir, Jun. 2000, vol. 17, Suppl3, pp. S31-S40 (Abstract).

Evans et al., "A Microcomputer System for Monitoring and Analysing Oxyhemolobin Saturation During Sleep," Computer Programs in Biomedicine, 1984, vol. 18, pp. 227-234.

Farhi et al., "Dynamics of Changes in Carbon Dioxide Stores," Anesthesiology, Nov.-Dec. 1960, vol. 21, pp. 604-614 (last page missing).

Farney et al., "Ear Oximetry to Detect Apnea and Differentiate Rapid Eye Movement (REM) and Non-REM (NREM) Sleep, Screening for the Sleep Apnea Syndrome," Chest, vol. 89, No. 4, Apr. 1986, pp. 533-539, Northbrook, IL, USA.

Farre et al., Importance of the Pulse Oximeter Averaging time When Measuring Oxygen Desaturation in Sleep Apnea, Sleep, Jun. 15, 1998, vol. 21, No. 4, pp. 386-390 Missing pages 386 and 390.

Feinsilver, "Current and Future Methodology for Monitoring Sleep," Sleep Disorders, Clinics in Chest Medicine, vol. 19, No. I, Mar. 1998, Published from the Division of Pulmonary Medicine, North Shore University Hospital, Manhasset, New York, NY, USA.

Ferber et al., "Portable Recording in the Assessment of Obstructive Sleep Apnea, ASDA Standards of Practice," American Sleep Disorders Association, 1610 14th Street, NW, Suite 300, Rochester, MN 55901-2200, USA.

Findley et al., "Cheyne-Stokes Breathing During Sleep in Patients With Left Ventricular Heart Failure," Southern Medical Journal, Jan. 1985, vol. 78(1), pp. 11-15.

Findley et al., "Sleep Apnea and Auto Crashes, What is the Doctor to do?," Chest, Aug. 1988, vol. 94(2), pp. 225-226.

Fisher, "Value of Pulse Oximetry Monitoring on the Ward is Questioned," Anesthesia Patient Safety Foundation Newsletter and posted on the Malpractice company's web site, The Doctors Company—Sleep Apnea and Narcotic Postoperative Pain . . . http://www.thedoctors.com/risk/bulletins/sleepapnea.asp.

Fiz et al., "Acoustic Analysis of Snoring Sound in Patients with Simple Snoring and Obstructive Sleep Apnoea," European Respiratory Journal, 1996, vol. 9, pp. 2365-2370, Printed in the United Kingdom.

Flemons et al., "Sleep Apnea and Cardiac Arrhythmias, Is There a Relationship?," American Review Respiratory Disease, vol. 148, pp. 618-621, 1993.

Fletcher et al., "Effect of Cardiac Output Reduction on Rate of Desaturation in Obstructive Apnea," Chest, 1991, vol. 99, pp. 452-456.

Fletcher et al., "Nocturnal Oxyhemoglobin Desaturation in COPD Patients with Arterial Oxygen Tensions Above 60 mm Hg," Chest, Oct. 1987, vol. 92, No. 4, pp. 604-608.

Fletcher et al., "Rate of Oxyhemolglobin Desaturation in Obstructive versus Nonobstructive Apnea," Am Rev Respi Dis., 1991, vol. 143, pp. 657-660.

Fletcher et al., "The Rate of Fall of Arterial Oxyhemoglobin Saturation in Obstructive Sleep Apnea," Chest, 1989, vol. 96, pp. 717-722.

Forster et al., "Time course of exchages between red cells and extracellular fluid during CQ uptake," Journal of Applied Physiology, vol. 38, No. 4, Apr. 2975, Printed in U.S.A.

Forster, "The Lung: Physiologic basis of Pulmonary Function Tests (Book)," 1986 Year Book medical Publishers, Inc., Chapter 3, I. Volume of Pulmonary Ventilation, pp. 32-64.

Franklin et al., "Developing strategies to prevent inhospital cardiac arrest: Analyzing responses of physicians and nurses in the hours before the event," Critical Care Medicine, 1994, pp. 244-247.

Franklin et al., "Reversal of Central Sleep Apnea with Oxygen," Chest, Jan. 1997, vol. 111(1), pp. 163-169 (Abstract).

Freid, "The rapid sequence induction revisited: obesity and sleep apnea syndrome," Anesthesiol Clin North America, Sep. 2005, vol. 23(3), pp. 551-564 (Abstract).

Frumin, "Apneic Oxygenation in Man," Anesthesiology, 1959, vol. 20, pp. 789-798.

Fu et al., "Supplemental Oxygen Impairs Detection of Hypoventilation by Pulse Oximetry," Chest, 2004, vol. 126, pp. 1552-1558.

Gagnadoux et al., "Home Unattended vs Hospital Telemonitored Polysomnography in Suspected Obstructive Sleep Apnea Syndrome: A Randomized Crossover Trial," Chest, 2002, vol. 121, pp. 753-758.

Gami et al., "Day-Night Pattern of Sudden Death in Obstructive Sleep Apnea," The New England Journal of Medicine, 2005, vol. 352(12), pp. 1206-1214.

Gangitano et al., Near Continuous Pulse Oximetry During Newborn ECLS, ASAI Journal, 1999, vol. 45, No. 1, p. 125 (Abstract).

Gaultier, C., "Upper airway muscles and physiopathology of obstructive sleep apnea syndrome," [Article in French], Neurophysiol Clin, Jun. 1994, vol. 24(3), pp. 195-206 (Abstract).

Gavin et al., "The effect of exercise modality on exercise-induced hypoxemia," Respiration Physiology, May 3, 1999, vol. 115, No. 3, pp. 317-323 (Abstract).

Gentil et al., "Enhancement of Postoperative Desaturation in Heavy Snorers," Anesth Analg, 1995, vol. 81, pp. 389-392.

George et al., "Identification on Qualification of Apneas by Computer-based Analysis of Oxygen Saturation," American Review of Respiratory Disease, 1988; 137; 1238-1240.

George, "Diagnostic Techniques in Obstructive Sleep Apnea," Progress in Cardiovascular Diseases, vol. 41, No. 5, Mar./Apr. 1999, pp. 355-366.

Glerant et al., "Intensive care and respiratory sleep disorders," [Article in French], Rev Mal Respir, Dec. 1999, vol. 16, No. 6, pp. 1091-104 (Abstract).

Gold et al., "Impact of Basic Research on Tomorrow's Medicine, The Pharyngeal Critical Pressure, The Whys and Hows of Using Nasal Continuous Positive Airway Pressure Diagnostically," Chest, vol. 110, No. 4, Oct. 1996, pp. 1077-1088, Northbrook, IL, USA.

Goldberger et al., "Components ofa New Research Resource for Complex Physiologic Signals, PhysioBank, PhysioToolkit, and PhysioNet, " American Heart Association Journals, Circulation, vol. 101, No. 23, pp. 1-9, 2000, Circulation, 2000:101:e215, http://circ.ahajournals.org/cgi/content/ful/101/23/e215.

Goldstein et al., Pulse Oximetry in Transport of Poorly-Perfused Babies, Abstract only, Pediatrics, 1998, vol. 102, No. 3, p. 818.

Goode, "Who needs a sleep test? The value of the history in the diagnosis of obstructive sleep apnea," Ear, Nose and Throat Journal, Sep. 1999, http://www.findarticles.com/p/articles/mi_m0BUM/is_9_78/ai_56229331/print.

Goodfriend et al., "Resistant Hypertension, Obesity, Sleep Apnea, and Aldosterone: Theory and Therapy, Hypertension," Journal of the American Heart Association, published online Jan. 19, 2004, Print ISSN: 0194-91 IX. Online ISSN: 1524-4563, pp. 518-524, Dallas, Texas, USA.

Grap, "Protocols for Practice, Applying Research at the Bedside," Critical Care Nurse, Feb. 1998, vol. 18, No. 1, pp. 94-99.

Greco et al., "Long-term Airway Space Changes after Mandibular Setback Using Bilateral Sagittal Split Osteomy," Internal Journal Oral Maxillofac. Surg., 1990, vol. 19, pp. 103-105.

Greco, "Cephalometric Analysis of Long-Term Airway Space Changes with Maxillary Osteotomies," Oral Surg Oral Med Oral Pathol, Nov. 1990, vol. 70, No. 5, pp. 552-554.

Griffiths et al., "A Video System for Investigating Breathing Disorders During Sleep," Thorad, 1991, vol. 46, pp. 136-140.

Grimm et al., "Outcome of patients with sleep apnea-associated severe bradyarrhythmias after continuous positive airway pressure therapy," American Journal Cardiology, Sep. 15, 2000, vol. 86, No. 6, pp. 688-692 (Abstract).

Grote et al., "Finger Plethysmography—A Method for Monitoring Finger Blood Flow During Sleep Disordered Breathing," Respiratory Physiology & Neurobiology, 2003, vol. 136, pp. 141-152.

Grunstein et al., "Treatment of Sleep Disordered Breathing, Position Statement," The Medical Journal of Australia, vol. 154, Mar. 4, 1991, pp. 355-359, Australia.

Gugger, "Comparison of ResMed AutoSet (version 3.03) with polysomnography in the diagnosis of the sleep apnoea/hypopnoea syndrome," European Respiratory Journal, Mar. 1997, vol. 10, No. 3, pp. 587-591 (Abstract).

Guilleminault et al., "A Cause of Excessive Daytime Sleepiness, The Upper Airway Resistance Syndrome," Chest, vol. 104, No. 3, Sep. 1993, pp. 781-787.

Guilleminault et al., "Maxillo-mandibular surgery for obstructive sleep apnoea," European Respiratory Journal, 1989, vol. 2, pp. 604-612.

Guilleminault et al., "Sleep Apnea Syndrome: Can It Induce Hemodynamic Changes?," Western Journal of Medicine, vol. 123, Jul. 1975, pp. 7-16.

Guilleminault et al., "Sleep-disordered breathing in children", Annals of Medicine, vol. 30, No. 4, pp. 350-356, Aug. 1998 (Abstract).

Guilleminault et al., "The Sleep Apnea Syndromes," Copyright 1976, Citation Annual Review of Medicine, vol. 27: 465-484 (Volume publication date Feb. 1976).

Guilleminault et al., "Unattended CPAP Titration: Toward a Smart Machine," May 20, Stanford University Sleep Research Center, 1 page.

Guilleminault, "Obstructive Sleep Apnea, The Clinical Syndrome and Historical Perspective," Medical Clinics of North America, vol. 69, No. 6, Nov. 1985, pp. 1187-1203, Stanford, California, USA.

Gupta et al., "Postoperative Complications in Patients with Obstructive Sleep Apnea Syndrome Undergoing Hip or Knee Replacement: A Case-Control Study," Mayo Clinic Proceedings, 2001, vol. 76, pp. 897-905, Rochester, MN, USA.

Gupta et al.," Perioperative cardiopulmonary evaluati and management: are we ignoring obstructive sleep apnea syndrome?," Chest, Dec. 1999, vol. 116, No. 6, p. 1843 (Abstract).

Gyulay et al., "A Comparison of Clinical Assessment and Home Oximetry in the Diagnosis of Obstructive Sleep Apnea," American Review of Respiratory Disease, 1993, vol. 147, pp. 50-53.

Gyulay et al., "Evaluation of a Microprocessor-Based Portable Home Monitoring System to Measure Breathing During Sleep," Sleep, vol. 10, No. 2, pp. 130-142, Raven Press, New York, USA, 1987, Association of Professional Sleep Societies.

Hanley et al., "Pathogenesis of Cheyne-Stokes Respiration in Patients with Congestive Heart Failure," Relationship to Arterial PC02, Chest, vol. 104, No. 4, Oct. 1993, pp. 1079-1084.

Hanly et al., "Increased Mortality Associated with Cheyne-Stokes Respiration in Patients with Congestive Heart Failure," American Journal Respiratory Critical Care Medicine, Jan. 1996, vol. 153, No. I, 272-6 (Abstract).

Hanly et al., "Respiration and Abnormal Sleep in Patients with Congestive Heart Failure", Chest, vol. 96, No. 3, Sep. 1989, pp. 480-488.

Hanly et al., "ST-Segment Depression During Sleep in Obstructive Sleep Apnea," The American Journal of Cardiology, vol. 71, Jun. 1, 1993, pp. 1341-1345.

Harbison et al.,"Cardiac rhythm disturbances in the obstructive sleep apnea syndrome: effects of nasal continuous positive airway pressure therapy," Chest, Sep. 2000, vol. 118, No. 3, pp. 591-(Abstract).

Hatta et al., "Prolonged upper airway instability in the parenteral use of benzodiazepine with levomepromazine," Journal Clin Psychopharmacol, Feb. 2000, vol. 20, No. 1, pp. 99-(Abstract).

He et al.,"Mortality and Apnea Index in Obstructive Sleep Apnea," Experience in 385 Male Patients, Clinical Investigations, Chest, vol. 94, No. I, Jul. 1988, pp. 9-14.

Health Devices, "Next-Generation Pulse Oximetry," Special Issue, Feb. 2003, vol. 32, No. 2, Plymouth Meeting, PA, USA.

Henderson, L. J., et al., Blood as a Physicochemical System. II, pp. 426-431, Paper.

Hillman et al., "Obstructive Sleep Apnoea and Anaesthesia," Sleep Medicine Reviews, 2004, vol. 8, pp. 459-472, Publisher: Elsevier.

Hoch et al., "Uberprufung der Fruherkennungsmethode MESAM and Biox 3700 zur Erfassung Schlafbezogener Atmmgmsergulationsstorungen bei jungen Mannern," Pneumologie, 1991; 45: 217-222 (and translation).

Hoffarth, et al., "Beuteilung Pulsoximetrisch Erfasster zklisheer . . . and translation (Hoffarth et al. Assessment of Cyclic and Phasic Oxygen Desaturations Measured via Pulsoxymetry in Nocturnal Diagnosis of Respiratory Regulation Disorders," Peumologie, May 1991, vol. 45, pp. 229-232.

Hoffman et al., "Multimodality Imaging of the Upper Airway: MRI, MR Spectroscopy, and Ultrafast X-ray CT," Sleep and respiration, 1990 Wiley-Liss, Inc., pp. 291-301.

Hoffmann et al., "Sleep apnea and hypertension," Minerva Med., Aug. 2004, vol. 95, No. 4, pp. 281-290 (Abstract).

Hoffstein et al., "Cardiac Arrhythmias, Snoring, and Sleep Apnea," Chest, 1994, vol. 106, pp. 466-471, Northbrook, IL, USA.

Hoffstein et al., "Snoring and Arousals: A Retrospective Analysis," Sleep, vol. 18, No. 10, pp. 866-882, 1995 American Sleep Disorders Association and Sleep Research Society.

Hoffstein, "Blood Pressure, Snoring, Obesity, and Nocturnal Hypoxaemia," The Lancet, vol. 344, Sep. 3, 1994, pp. 643-645.

Holmes et al., "Co-Oximetry Validation ofa New Pulse Oximeter in Sick Newborns," Respiratory Care, 1998, vol. 43, No. 10, pp. 860 (Abstract).

Howell et al. "Pulse oximetry: an audit of nursing and medical staff understanding", British Journal of Nursing, 2002, vol. 11, pp. 191-197.

Hung et al., "Association of Sleep Apnoea with Myocardial Interfarction in Men," The Lancet, vol. 336, DP. 261-264, Jul. 28, 1990, Abstract only, p. 261.

Isono et al., "Anatomy of pharynx in patients with obstructive sleep apnea and in normal subjects," Journal Appl Physiol, Apr. 1997, vol. 82, No. 4, pp. 1319-1326 (Abstract).

Isono et al., "Interaction of cross-sectional area, driving pressure, and airflow of passive velopharynx," Journal Appl Physiol, Sep. 1997, vol. 83, No. 3, pp. 851-859 (Abstract).

Isono et al., "Static mechanics of the velopharynx of patients with obstructive sleep apnea," Journal Appl Physiol, Jul. 1999, vol. 75, No. 1, pp. 148-154 (Abstract).

Jain et al., "Perioperative Treatment of Patients with Obstructive Sleep Apnea," Current Opinion Pulmonary Medicine, 2004, vol. 10, pp. 482-488.

Jarrell, "Preoperative diagnosis and postoperative management of adult patients with obstructive sleep apnea syndrome: a review of the literature," Journal Perianesth Nursing, Aug. 1999, vol. 14, No. 4, pp. 193-200 (Abstract).

Javaheri et al., "Occult Sleep-Disordered Breathing in Stable Congestive Heart Failure," Annuals Internal Medicine, Apr. 1995, vol. 122, No. 7, pp. 487-492 (Abstract).

Javaheri et al.,"Sleep Apnea in 81 Ambulatory Male Patients With Stable Heart Failure, Types and Their Prevalences, Consequences, and Presentations," Received Nov. 20, 1997; revision received Jan. 23, 1998, accepted Jan. 28, 1998, From the Sleep Disorders Laboratory, Department of Veterans Affairs Medical Center, and the Department of Medicine, University of Cincinatti, College of Medicine, Cincinnati, Ohio.

Javaheri, "Effects of continuous positive airway pressure on sleep apnea and ventricular irritability in patients with heart failure," Circulation, Feb. 1, 2000, vol. 101, No. 4, pp. 392-397 (Abstract).

Johnson et al., "Preoperative, Intraoperative, and postoperative management of patients with obstructive sleep apnea syndrome," Otolaryngol Clin North America, Dec. 1998, vol. 31, No. 6, pp. 1025-1030 (Abstract).

Jones et al., "The Estimation of Carbon Dioxide Pressure of Mixed Venous Blood During Exercise," Clinical Science (1967), vol. 32, pp. 311-327.

Juhasz et al., "Unattended Continuous Positive Airway Pressure Titration, Clinical Relevance and Cardiorespiratory Hazards of the Method", American Journal Respiratory Critical Care Medical, vol. 154, pp. 359-365, 1996.

Kabeli, "Obstructive Sleep apnea and Modifications in Sedation, Critical Care Nursing Clinics of North America," vol. 17, 2005, pp. 269-277, ccnursing.theclinics.com, Publisher: Elsevier Saunders.

Kalra et al.,"Obstructive Sleep Apnea in Extremely Overweight Adolescents Undergoing Bariatric Surgery," Obesity Research, vol. 13, No. 7, Jul. 2005, pp. 1175-1179.

Kanagala et al., "Obstructive Sleep Apnea and the Recurrence of Atrial Fibrillation, Circulation," May 27, 2003, pp. 2589-2594, American Heart Association, Inc.

Kaplan et al.,"Home Pulse Oximetry as a Screening Test for Sleep-Disordered Breathing," Chest, vol. 103, pp. 322S, Northbrook, IL, USA.

Kaplan, "Beginner's Atlas of Overnight Oximetry," Apr. 10, 1995, Mayo Clinic, Jacksonville, Florida, USA, Copyright 1986, PROFOX Associates, Inc.

Kapur et al., "The medical cost of undiagnosed sleep apnea," Sleep, Sep. 1999, vol. 22, No. 6, pp. 749-755 (Abstract).

Kapur et al.,"Association of hypothyroidism and obstructive sleep apnea," American Journal of Respiratory & Critical Care Medicine, vol. 158, No. 5 Pt. 1, pp. 1379-1383, Nov. 1998 (Abstract).

Katchen et al., "Evaluation of the Sleepy Crewmember: USAFSAM Experience and a Suggested Clinical Approach," Aviation, Space and Environrrental Medicine, Mar. 1989, pp. 263-267.

Kaw et al., "Unrecognized Sleep Apnea in the Surgical Patient, Implications for the Perioperative Setting," Chest, 2006, vol. 129, pp. 198-205.

Kawai et al., "Nocturnal hypoxia index: A new pulse oximetry index of nocturnal hypoventilation in neuromuscular disorders," Clinical Neurology, vol. 35, pp. 1003-1007, 1995 (Abstract).

Keyl et al., "Spektralanalyse von Arterieller Sauerstoff-sattigung and RR-Intervallen bei Patienten mit obstrukitver Schlafapnoe," Wein Med Wschr, 1995, vol. 145, pp. 515-516.

Kimmel et al., "Sleep Apnea syndrome in Chronic renal Disease," The American Journal of Medicine, Mar. 1989, vol. 86, pp. 308-314.

King et al., "A model of obstructive sleep apnea in normal humans. Role of the upper airway," American Journal Respiratory Critical Care Medicine, Jun. 2000, vol. 161, No. 6, pp. 1979-1984 (Abstract).

Kirby et al., "Computer Quantitation of Saturation Impairment Time as an Index of Oxygenation During Sleep," Com Meth, vol. 1992, pp. 107-115.

Kirby et al., "Neural network prediction of obstructive sleep apnea from clinical criteria," Chest, Aug. 1999, vol. 116, No. 2, pp. 409-415 (Abstract).

Kirby et al., "Section II. Systems and programs, Computer quantitation of saturation impairment time as an index of oxygenation during sleep," Computer Methods and Programs in Biomedicine, vol. 38, 1992, pp. 107-115.

Klocke et al., "Breath holding after breathing of oxygen," Journal Appl. Physiol., 1959, vol. 14, No. 5, pp. 689-693.

Koehler et al., "Heart Block in Patients with Obstructive Sleep Apnoea: Pathogenetic Factors and Effects of Treatment," European Respiratory Journal, 1998, vol. 11, pp. 434-439, Printed in United Kingdom.

Koehler et al., "Nocturnal Myocardial Ischemia and Cardiac Arrhythmia in Patients with Sleep Apnea with and Without Coronary Heart Disease," Journal of Molecular Medicine, 1991, vol. 69, pp. 474-482.

Kolobow et al., "Intratracheal Pulmonary Ventilation (ITPV); Control of Positive End-Expiratory Pressure at the Level of the Carina Through the Use of a Novel ITPV Catheter Design," Anesth Analg, 1994, vol. 78, pp. 455-461.

Koopmann et al., "Surgical Management of Obstructive Sleep Apnea," Otolaryngologic Clinics of North America, Aug. 1990, vol. 23, No. 4, pp. 787-808.

Krachman et al., "Comparison of oxygen therapy with nasal continuous positive airway pressure on Cheyne-Stokes respiration during sleep in congestive heart failure," Chest, Dec. 1999, vol. 116, No. 6, pp. 1550-1557 (Abstract).

Kribbs et al., "Effects of One Night without Nasal CPAP Treatment on Sleep and Sleepiness in Patients with Obstructive Sleep Apnea," American Review Respiratory Disease, vol. 147, pp. 1162-1168, 1993.

Kribbs et al., "Objective Management of Patterns of Nasal CPAP Use by Patients with Obstructive Sleep Apnea," American Review Respiratory Disease, vol. 147, pp. 887-895, 1993.

Krieger et al., "Breathing During Sleep in Normal Middle-Aged Subjects," Sleep, vol. 13, No. 2, pp. 143-154, Raven Press, Ltd. New York, NY, USA, 1990 Association of Professional Sleep Societies.

Krieger et al., "Dangerous Hypoxaemia During Continuous Positive Airway Pressure Treatment of Obstructive Sleep Apnoea," The Lancet, Dec. 17, 1983, pp. 1429-1430.

Krieger et al., "Left Ventricular Ejection Fraction in Obstructive Sleep Apnea, Effects of Long-term Treatment with Nasal Continuous Positive Airway Pressure," Chest, vol. 100, No. 4, Oct. 1991, pp. 917-921.

Kuna et al., "Pathophysiology of upper airway closure during sleep," JAMA, Sep. 11, 1991, vol. 266, No. 10, pp. 1384-1389 (Abstract).

Kyzer et al., "Obstructive Sleep Apnea in the obese," World Journal Surg, Sep. 1988, vol. 22, No. 9, pp. 998-1001 (Abstract).

Lafontaine et al., "Pulse Oximetry: Accuracy of Methods of Interpreting Graphic Summaries," Pediatric Pulmonology, vol. 21, 1996, pp. 121-131.

Lanfranchi et al., "Prognostic value of nocturnal Cheyne-Stokes respiration in chronic heart failure," Circulation, Mar. 23, 1999, vol. 99, No. 11, pp. 1435-1440, Italy (Abstract).

Lanfranchi, "The assessment of breathing during sleep: a curiosity or clinical necessity?," Italian Heart Journal, May 2000, vol. 1, No. 5 Suppl., pp. 641-654 (Abstract).

Lawrence, "Treatment for Sleep Apnea shows promise in reducing deaths from congestive heart failure: Nation-wide study to determine long-term benefits," London Health Sciences Centre, Jul. 3, 1999, News Bulletin.

Lertzman et al., [Letters-Correspondence], "Sleep Apnea a Risk Factor for Poor Driving," Canadian Medical Association Journal, Oct. 15, 1995, vol. 153. No. 8, p. 1063.

Letters, "Obstructive Sleep Apnoea," BMJ, 1997, pp. 315-367 (Aug. 9); http://bmj.com/Shneerson et al. (7104).

Lichstein et al., "Occult sleep apnea in a recruited sample of older adults with insomnia," Journal of Consulting & Clinical Psychology, vol. 67, No. 3, pp. 405-410, Jun. 1999 (Abstract).

Little et al., "Predictors of nocturnal oxygen desaturation in patients with COPD," Respir Med., Mar. 1999, vol. 93, No. 3, pp. 202-207, United Kingdom (Abstract).

Lofsky, "Sleep Apnea and Narcotic Postoperative Pain Medication: A Morbidity and Mortality Risk," APSF Newsletter Summer 2002, pp. 24-25.

Longobardo et al., "Sleep Apnea Considered as a Control System Instability," Elsevier Biomedical Press, 1982, 0034-5687/82/0000-0000.

Longobardo et al., "Sleep Apnea Considered as a Control System Instability," Sep. 1982, Respiratory Physiology 50: 311-333.

Lowton, "Pulse oximeters for the detection of hypoxaemia," Professional Nurse, Feb. 1999, vol. 14, No. 5, pp. 343-347 (Abstract).

Lugaresi et al., "Breathing During sleep in Man in Normal and Pathological Conditions, Proceedings of the Symposium on Regulation of Respiration during Sleep and Anesthesia held at the Faculte de Medecine Saint-Antoine," Paris, France, Jul. 14-16, 1977, 1978 Plenum Press, New York, USA, pp. 35-45.

Lynn et al., "Diagnostic Evaluation of OSA Utilizing Analysis of Frequency and Spatial Relationships of Clustered, Sequential Oximetry Waveform Events," Vth World Congress on Sleep Apnea, Marburg, Gennany, Sep. 17-20, 1997.

Lynn, "Cluster Analysis: A New Technology for the Evaluation of Oximetry and Airflow Waveforms in Obstructive Sleep Apnea," Accepted after revision on Dec. 20, 1997, 17 total pages.

Lynn, "Interpretive Oximetry: Future Directions for Diagnostic Applications of the SP02 Time-Series," Anesth Analg, 2002, vol. 94, pp. S84-S88.

Lynn, "Piercing the Panacea of Pulse Oximetry;" The Sleep and Breathing Research Institute, Columbus, Ohio, US.

Lynn, "PROFOX Associates, Inc., Version 12S (12 hours Sp02)," Demonstration disk for Dr. Lawrence Lynn, Columbus, Ohio, Copyright 1986 PROFOX Associates, Inc., Version 12S, Nov. 1992, p. 1.

Lyznicki, "Sleepiness, Driving and Motor Vehicle Crashes," JAMA, Jun. 17, 1998, vol. 279, No. 23, pp. 1908-1913.

MacKenzie, "The haemodynamics of human septic shock," Anaesthesia, 2001, vol. 56, pp. 130-144.

Magalang et al., "Prediction of the Apnea-Hypopnea Index From Overnight Pulse Oximetry," Chest the Cardiopulmonary and Critical Care Journal, 2003; vol. 124; pp. 1694-1701, Northbrook, IL, USA.

Manley, "Cerebral oxygenation during hemorrhagic shock: perils of hyperventilation and the therapeutic potential of hypoventilation," J Trauma, 2000, vol. 48, pp. 1025-1032.

Marin et al., "Obstructive Sleep Apnea and Acute Myocardial Infarction: Clinical Implications of the Association," Sleep, vol. 21, No. 8, 1998, pp. 809-815.

Marin et al., "Long-Term Cardiovascular Outcomes in Men with Obstructive sleep apnoea-hypopnoea with or without treatment with continuous positive airway pressure: an observational study," The Lancet, Mar. 19-25, 2005, vol. 365(9464), pp. 1046-1053.

Mayer, et al., "Peripheral Neuropathy in Sleep Apnea, a Tissue Marker of the Severity of Nocturnal Desaturation," American Journal Respiratory Critical Care Medicine, vol. 159, pp. 213-219, 1999, Internet address: www.atsiournals.org.

McDannold et al.,"Night-to-Night variability in Optimal CPAP Pressures Using Auto CPAP Titration in a Single Patient," Sleep Research No. 23, 1994, p. 453 (Abstract).

McEvoy et al., "Ventilatory responses to sustained eucapnic hypoxia in healthy males during wakefulness and NREM sleep," Sleep, vol. 20, No. II, Nov. 1997, pp. 1008-1011 (Abstract).

McGregor et al., "Perfonnance of Pulse Oximeter Technologies in a Pediatric Sleep Lab Setting," OF-901-191, dated Nov. 2, 2001, Abstract.

McNicholas et al., "Diagnostic Criteria for the Sleep Apnoea Syndrome: Time for Consensus?," European Respiratory Journal, vol. 9, pp. 634-635, 1996, United Kingdom.

McQuillan et al., "Confidential inquiry into quality of care before admission to intensive care," BMJ, vol. 316, Jun. 20, 1998, www.bmj.com, pp. 1853-1858.

Mehra et al., "Association of Nocturnal Arrhythmias with Sleep-Disordered Breathing: The Sleep Heart Health Study," AJRCCM Articles in Press, Published Jan. 19, 2006, as doi: 10.1164/rccm.200509-14420C, Copyright 2006 by the American Thoracic Society.

Mehta et al.," Obstructive sleep apnea syndrome: anesthetic implications in the cardiac surgical patient," Journal Cardiothorac Vase Anesth, Aug. 2000, vol. 14, No. 4, pp. 449-453 (Abstract).

Mendelson et al., "Effects of Hemodialysis on Sleep Apnea Syndrome in End-Stage Renal Disease," Clinical Nephrology, vol. 33, No. 5, 1990, pp. 247-251.

Middlekoop et al.,"The Value of Nocturnal Motor Activity Monitoring as a Screening Tool for Obstructive Sleep Apnoea," Letter to the Editor, Journal Sleep Res., 1996, vol. 5, pp. 66-67.

Miles et al., "Development and Application of Automatic Nasal CPAP Calibration Procedures for Use in the Unsupervised Home Environment," Sleep, vol. 16, pp. S11S-S1 19,1993 American Sleep Disorders Association and Sleep Research Society.

Miles, "Optimization of Nasal-CPAP Airflow Pressure by Use of Home Oximetry Recordings, " Clinical Monitoring Center, Palo Alto, California, USA, Sleep Research, p. 568, 1987, Abstract.

Millard, "Inductive plethysmography components analysis and improved noninvasive postoperative apnoea monitoring," Physiol Meas, May 1999, vol. 20, No. 2, pp. 175-186, United Kingdom (Abstract).

Mitler et al., "Narcolepsy and its Treatment With Stimulants," ASDA Standards of Practice, Sleep, vol. 17, No. 4, pp. 352-371, 1994, American Sleep Disorders Association and Sleep Research Society.

Miyamura et al., "CO2 Dissociation Curves of Oxygenerated Whole Blood Obtained at Rest and in Exercise," European Journal Applied Physiology, vol. 39, pp. 37-45, 1978, European Journal of Applied Physiology and Occupation Physiology.

Moller et al., "Hypoxaemia is reduced by pulse oximetry monitoring in the operating theatre and in the recovery room," British Journal of Anaesthesia, 1992, vol. 68, pp. 146-150.

Moller et al., "Randomized evaluation of pulse oximetry in 20,802 patients: I. Design, demography, pulse oximetry failure rate, and overall complication rate," Anesthesiology, 1993, vol. 78, pp. 436-444.

Moller et al., "Randomized evaluation of pulse oximetry in 20,802 patients: II. Perioperative events and postoperative complications," Anesthesiology, 1993, vol. 78, pp. 445-453.

Morelot-Panzini et al., "Simplified Method to Measure Respiratory-Related Changes in Arterial Pulse Pressure in Patients Receiving Mechanical Ventilation", Chest 2003, vol. 124, pp. 665-670, Northbrook, IL, USA.

Muller et al., "Mechanism of Hemoglobin Desaturation During Rapid-Eye-Movement Sleep in Nonnal Subjects and in Patients with Cystic Fibrosis," American Review of Respiratory Disease, vol. 121, 1980, pp. 463-469.

Murray et al. "Making the most of pulse oximetry", Contemporary Pediatrics, 1995, vol. 12, pp. 45-62.

Myatt et al., "Snoring—a simple surgical solution," Clin. Otolaryngol., 1996, vol. 21, pp. 419-424, Publisher: Blackwell Science Ltd.

Narkiewicz et al., "Altered Cardiovascular Variability in Obstructive Sleep Apnea," Copyright 1998, American Heart Association, Inc., Iowa City, Iowa, USA, pp. 1071-1077, Published Sep. 15, 1998.

Naughton et al., "Sleep Apnea in Congestive Heart Failure," Clinics in Chest Medicine, vol. 19, No. 1, Mar. 1998, pp. 99-113.

Naughton, "Cycling Sleep Apnea, The Balance of Compensated and Decompensated Breathing," American Journal of Respiratory and Critical Care Medicine, vol. 168, 2003, Editorials, pp. 624-625.

Netzer et al., "Overnight Pulse Oximetry for Sleep-Disordered Breathing in Adults," A Review, Chest, vol. 120, #2, Aug. 2001, pp. 625-633, Northbrook, IL, USA.

Neuman, "Pulse oximetry: physical principles, technical realization and present limitations", Adv Exp Med Biol, 1987, vol. 220, pp. 135-144.

Neumann et al., "Nocturnal oxygen desaturation in diabetic patients with severe autonomic neuropathy," Diabetes Research and Clinical Practice, Publisher: Elsevier Science Ireland Ltd, vol. 28, 1995, pp. 97-102.

Nobili et al., "Morning increase of whole blood viscosity in obstructive sleep apnea syndrome," Clinical Hemorheol Microcirc, 2000, vol. 22, No. I, pp. 21-27 (Abstract).

Noda et al., "Circadian Rhytlun of Autonomic Activity in Patients with Obstructive Sleep Apnea Syndrome," Clinical Cardiology, vol. 21, pp. 271-276,1998, Japan.

Noda et al., "Daytime sleepiness and automobile accidents in patients with obstructive sleep apnea syndrome," Psychiatry & Clinical Neurosciences, vol. 52, No. 2, pp. 221-222, Apr. 1988 (Abstract).

O'Donovan et al. "Acid-base disturbances in cardiogenic pulmonary edema", Nephron, 1991, vol. 57, pp. 416-420.

Ogan et al.,"Anesthetic safety always an issue with obstructive sleep apnea," Journal Clin Monit Comput, Jan. 1998, vol. 14, No. I, pp. 69-70 (Abstract).

Ogretmenoglu et al., "Body fat composition: a predictive factor for obstructive sleep apnea," Laryngoscope, Aug. 2005, vol. 115, No. 8, pp. 1493-1498 (Abstract).

Ohga et al., "Increased Levels of Circulating ICAM-1, VCAM-1, and L-selectin in obstructive sleep apnea syndrome," Address for reprint requests and other correspondence: T. Nagase, Dept. of Geriatric Medicine, Faculty of Medicine, Univ. of Tokyo, 7-3-1, Hongo, Bunkyo-Ku, Tokyo 113, Japan, Received Nov. 13, 1998, accepted in final form Mar. 9, 1999.

Olson et al., "Chapter 10, A Biomechanical View of Upper Airway Function," pp. 359-389, 1988, Publisher, Marcel Dekker, Inc., New York-Basel, Book: Respiratory Function of the Upper Airway.

Olson et al., "Prediction of Sleep-disordered breathing by unattended overnight oximetry," Journal Sleep Res., 1999, vol. 8, pp. 51-55, European Sleep Research Society.

Ostermeier et al., "Three sudden postoperative respiratory arrests associated with epidural opioids in patients with sleep apnea," Anasth Analg., Aug. 1997, vol. 85, No. 2, pp. 452-460.

Owen et al., "Overnight Pulse Oximetry in Snoring and Non-Snoring Children," Clinical Otolaryngology, 1995, vol. 20, pp. 402-406, Blackwell Science Ltd.

Owen et al.,"Overnight Pulse Oximetry in Nonnal Children and in Children Undergoing Adenotonsillecomy," Clinical Otolaryngology, 1996 vol. 21, pp. 59-65, Blackwell Science Ltd.

Oxican, "AirSep Corporation, 800/874-0202, Oxiscan Sample Report/Explanation and the Delta Sleep Apnea Index," OxiScan Sample Report, vol. 1, Rev. 01, Nov. 1997.

Pae et al., "Intermittent hypoxia damages cerebellar cortex and deep nuclei," Neurosci Lett., Feb. 28, 2005, vol. 375, No. 2, pp. 123-128.

Partinen et al., "Daytime Sleepiness and Vascular Morbidity at Seven-Year Follow-up in Obstructive Sleep Apnea Patients," Chest, vol. 97, No. 1, Jan. 1990, pp. 27-32.

Patil et al., "Application of an Artificial Intelligence Program to Therapy of High Risk Surgical Patients," New Horizons, vol. 4, No. 4, pp. 541-550.

Payne, "Apnoeic Oxygenation in Anaesthetised Man," Acta Anaesth. Scandinav., 1962, vol. 6, pp. 129-142.

Peker et al., "An independent association between obstructive sleep apnoea and coronary artery disease," European Respiratory Journal, 1999, vol. 14, No. 1, pp. 179-184 (Abstract).

Peker et al., "Reduced hospitalization with cardiovascular and pulmonary disease in obstructive sleep apnea patients on nasal CPAP treatment," Sleep, 1997, vol. 20, No. 8, pp. 45-53 (Abstract).

Peled et al., "Nocturnal ischemic events in patients with obstructive sleep apnea syndrome and ischemic heart disease: effects of continuous positive air pressure treatment," Journal American Coll Cardiology, Nov. 1999, vol. 15, p. 34 (Abstract).

Pelttary et al.,"Little Effect of Ordinary Antihypertensive Therapy on Nocturnal High Blood Pressure in Patients with Sleep Disordered Breathing," American Journal of Hypertension, 1998, vol. 11, No. 3, Part 1, pp. 272-279.

Penzel et al., "Systematic Comparison of Different Algorithms for Apnoea Detection Based on Electrocardiogram Recordings," Medical & Biological Engineering and Computing, 2002, vol. 40, pp. 402-407.

Pepin et al., "Does Oximetry contribute to the Detection of Apneic Events? Mathematical. Processing of the SaO.sub.2 Signal," Chest, May 1991; 99: 1151-1157.

Peppard et al., "Prospective Study of the Association Between Sleep-Disordered Breathing and Hypertension," May 11, 2000, vol. 342, No. 19, pp. 1378-1384.

Peters et al., "Studies of the Carbon Dioxide Absorptipn Curve of Human Blood, Book: The Journal of Biological Chemistry," pp. 709-716, Received for publication, Feb. 7, 1923.

Peters et al.,"The Carbon Dioxide Absorption Curve and Carbon Dioxide Tension of the Blood of Normal Resting Individuals, Book: Carbon Dioxide Absorption Curve," pp. 489-547, Received for publication, Dec. 2, 1920 (missing pp. 490, 491, 538-541).

Phillips et al., "Catching up on Sleep, The National Sleep Disorders Research Plan," Editorial, Chest, vol. 110, No. 5, Nov. 1996, pp. 1132-1133.

Phillips et al., "Obstructive Sleep Apnoea: Diagnosis and Management," Nursing Standard, vol. II, No. 17, pp. 43-46, 1997.

Phillipson, "Sleep Apnea—A Major Public Health Problem, Editorials," The New England Journal of Medicine, Editorials, vol. 328, No. 17, pp. 1271-1273, Apr. 29, 1993.

Plastiras, "Sleep disorders create need for more sleep labs," Capital District Business Review, Mar. 9, 1998.

Poets et al., "Arterial oxygen saturation and breathing movements during the first year of life," Journal Developmental Physiology, Jun. 1991, vol. 15, No. 6, pp. 341-345 (Abstract).

Poets et al., "Oxygen saturation and breathing patterns in infancy. 2: Preterm infants at discharge from special care," Arch Dis Child, May 1991, vol. 66, No. 5, pp. 574-578 (Abstract).

Poets et al., "Patterns of oxygenation during periodic breathing in preterm infants", Early Human Development, Jul. 1991, vol. 26, No. 1, pp. 1-12 (Abstract).

Poets et al.," Home monitoring of transcutaneous oxygen tension in the early detection of hypoxaemia in infants and young children," Arch Dis Child, Jun. 1991, vol. 66, No. 6, pp. 676-682 (Abstract).

Poets, "Apparent life-threatening events and sudden infant death on a monitor," Paediatr Respiratory Review, 2004, Suppl. A, pp. S383-S386 (Abstract).

Pradhan et al., "Screening for Obstructive Sleep Apnea in Patients Presenting for Snoring Surgery," Laryngoscope, vol. 106, Nov. 1996, pp. 1393-1397.

Principe-Rodriguez et al., "Sleep symptoms and clinical markers of illness in patients with heart failure," Sleep Breath., Sep. 2005, vol. 9, No. 3, pp. 127-133 (Abstract).

Quinn et al., "The Differentiation of Snoring Mechanisms Using Sound Analysis," Clinical Otolaryngol., 1996, vol. 21, pp. 119-123, Publisher: Blackwell Science Ltd.

Randerath et al., "Autoadjusting CPAP Therapy Based on Imp Compliance and Acceptance", American Journal Respiratory Critical Care Medicine, vol. 163, pp. 652-657, 2001, Internet address: www.atsjiournals.org.

Rapoport et al., "Reversal of the "Pickwickian Syndrome" by Long-Term Use of Nocturnal Nasal-Airway Pressure," The New England Journal of Medicine, Oct. 7, 1982, vol. 307, No. 15, pp. 931-933.

Rapoport, et al., "CO2 Homeostasis During Periodic Breathing: Predictions From a Computer Model," The American Journal of Applied Physiological, 1993, vol. 75, Issue 5, pp. 2302-2309.

Rauscher et al., "Computerized Detection of Respiratory Events During Sleep from Rapid Increases in Oxyhemoglobin Saturation," Lung, 1991, vol. 169, pp. 335-342.

Rauscher et al., "Quantification of sleep-disordered breathing by computerized analysis of oximetry, heart rate, and snoring," Eur Respir J., Jun. 1991, vol. 4, pp. 655-659.

Redline et al., "Hypopnea, a Floating Metric: Implications for Prevalence," Morbidity Estimates, and Case Finding, Sleep, vol. 20, No. 12, pp. 1209-1217.

Redline et al., "Recognition and Consequences of Obstructive Sleep Apnea Hypopnea Syndrome, Sleep Disorders," Clinics in Chest Medicine, vol. 19, No. I, Mar. 1998, Cleveland, Ohio, USA (Article and Abstract).

Reite et al., "The Use of Polysomnography in the Evaluation of Insomnia, An American Sleep Disorders Association Review," Sleep, vol. 18, No. I, 1995, pp. 58-70, American Sleep Disorders Association and Sleep Research Society 1995.

Remmers et al., "Nasal Airway Positive Pressure in Patients with Occlusive Sleep Apnea, Methods and Feasibility," American Review Respiratory Disorders, Dec. 1984, vol. 130, No. 6, pp. 1152-1155.

Rennotte, "Epidural opioids and respiratory arrests," Anesth Analg., Aug. 1997, vol. 85, No. 2, pp. 452-460 (Abstract).

Resta et al., "Sleep-related breathing disorders in acute respiratory failure assisted by non-invasive ventilatory treatment: utility of portable polysomnographic system," Respir Medicine, Feb. 2000, vol. 94, No. 2, pp. 128-134 (Abstract).

Riley et al., "Maxillofacial Surgery and Nasal CPAP, A Comparison of Treatment for Obstructive Sleep Apnea Syndrome," Chest, vol. 98, No. 6, Dec. 1990, pp. 1421-1425.

Riley et al., "Maxillofacial Surgery and Obstructive Sleep Apnea Syndrome," Otolaryngologic Clinics of North America, vol. 23, No. 4, Aug. 1990, pp. 809-824.

Riley et al., "Maxillofacial Surgery and Obstructive Sleep Apnea: A Review of 80 Patients," Otolaryngology-Head and Neck Surgery, vol. 101, No. 3, Sep. 1989, pp. 353-361.

Rosenberg et al., "Ventilatory Pattern and Associated Episodic Hypoxaemia in the Late Postoperative Period in the General Surgical Ward," Anaesthesia, 1999, vol. 54, pp. 323-328, Publisher: Blackwell Science Ltd.

Roux et al., "Sleep-related Breathing Disorders and Cardiovascular Disease," The American Journal of Medicine, Apr. 1, 2000, vol. 108, pp. 396-400.

Ruchala, Chapter 13, "Applications of Pulse Oximetry, Book: Design of Pulse Oximeters," pp. 214-236.

Ruhle et al., "Monitoring at Home, Lung," 1990, Suppl, pp. 927-932, Lung, Springer-Verlag, New York, Inc. 1990.

Rundell et al., "Polysomnography Methods and Interpretations, Sleep Apnea," Otolaryngologic Clinics of North America, vol. 23, No. 4, Aug. 1990, pp. 583-592.

Rusch et al., "Signal Processing Methods for Pulse Oximetry," Computers in Biology & Medicine, vol. 26, No. 2, pp. 143-159, Mar. 1996 (Abstract).

Ryan et al., "Mechanical Properties of the Velopharynx in Obese Patients with Obstructive Sleep Apnea," American Journal Respiratory Critical Care Medicine, 1996, vol. 154, pp. 806-812.

Ryan et al., "Periodicity of Obstructive Sleep Apnea in Patients With and Without Heart Failure," Chest 2005; 127, pp. 536-542.

Saarelainen et al., "Effect of Nasal CPAP Treatment on Plasma Volume, Aldosterone and 24-h Blood Pressure in Obstructive Sleep Apnoea," Journal Sleep Research, 1996, vol. 5, pp. 181-185.

Sadeh et al., "The Role of Actigraphy in the Evaluation of Sleep Disorders," An American Sleep Disorders Association and Sleep Research Society, Sleep, vol. 18, No. 4, pp. 288-302.

Sadrmoori, "Evaluation of Self Adjusting Nasal CPAP (DPAP) in the Treatment of Adult Obstructive Sleep Apnea," Sleep Research, 1994, No. 23, p. 386 (Abstract).

Saito et al., "Sleep Apnea in Patients with Acute Myocardial Infarction," Critical Care Medicine, vol. 19, No. 7, pp. 938-941, Printed in USA, Copyright 1991 by Williams and Wilkins.

Sajkov et al., "Daytime Pulmonary Hemodynamics in Patients with Obstructive Sleep Apnea without Lung Disease," American Journal Respiratory Critical Care Medicine, 1999, vol. 159, pp. 1518-1526.

Salmi et al., "Evaluation of Automatic Analysis of SCSB, Airflow and Oxygen Saturation Signals in Patients with Sleep Related Apneas," Chest, 1989, vol. 96, pp. 255-261.

Sanders et al., "Obstructive Sleep Apnea Treated by Independently Adjusted Inspiratory and Expiratory Positive Airway Pressures via Nasal Mask," Chest, 1990: 98: 317-24.

Sanders et al., "Obstructive Sleep Apnea Treated by Independently Adjusted Inspiratory and Expiratory Positive Airway Pressures via Nasal Mask," Physiologic and Clinical Implications, Chest, vol. 98, No. 2, Aug. 1990, pp. 317-324.

Sanders, "Nasal CPAO Effect on Patterns of Sleep Apnea," Chest, vol. 86, No. 6, Dec. 1984, pp. 839-844.

Sangal et al., "P300 Latency: Abnormal in Sleep Apnea with Somnolence and Idiopathic Hypersomnia, but Normal in Narcolepsy," Clinical Electroencephalography, 1995, vol. 26, No. 3, pp. 146-153, Troy, Michigan, USA.

Sanna, et al., "Apport de la Polysomnographie a la mise au point des maladies atteints d'une bronchopneumopathie chronique obstructive (BPCO)," Travail Original, Rev. Med. Brux., vol. 12, pp. 315-320,1991, Belgium.

Sanner et al., "Sleep-related respiration disorders: their relevance in intensive care medicine," [Article in German] Dtsch Med Wochenschr, Mar. 1999, vol. 12, p. 124 (Abstract).

Sarodia et al., "Prevalence of obstructive sleep apnea in patients admitted to the intensive care unit with cardiovascular events," Sleep Research, 1996, vol. 25, pp. 356.

Schafer et al., "Cardiovascular morbidity in patients with obstructive sleep apnea in relation to the severity of respiratory disorder," Dtsch Med Wochenschr, 1998, vol. 123, No. 39, pp. 1127-1133 (Abstract).

Schafer, et al., "Pulmonary Haemodynamics in Obstructive Sleep Apnoea: Time Course and Associated Factors," European Respiratory Journal, 1998, vol. 12, pp. 679-684, Printed in United Kingdom.

Schagatay et al., "Diving Response and Apneic Time in Humans," Undersea Hyper Med., 1998, vol. 25, No. 1, pp. 13-19, Copyright 1988 Underseas and Hyperbaric Medical Society, Inc.

Scharf et al., "Cyclic Alternating Pattern Sequences in Non-Apneic Snorers With and Without Nasal Dilation," ENT-Ear, Nose & Throat Journal, Sep. 1996, vol. 75, No. 9, pp. 617-619.

Scharf, et al., "Cardiovascular Effects of Periodic Occlusions of the Upper Airways in Dogs," American Review of Respiratory Disease, pp. 321-329.

Scheers, N. J., et al., Sudden Infant Death With External Airways Covered, Case-Comparison Study of 206 Deaths in the United States, Arch Pediatric Adolescent Medicine, 1998, vol. 152, pp. 540-547.

Schein, R. M. et al., Clinical antecedents to in-hospital cardiopulmonary arrest, Chest 1990; pp. 1388-1392, Copyright 1990, Downloaded from www.chestjournal.org at Grant Medical Center on Jul. 1, 2009.

Schmidt-Notwara, et al., "Oral Appliances for the Treatment of Snoring and Obstructive Sleep Apnea: A Review, An American Sleep Disorders Association Review," Sleep, vol. 18, No. 6, pp. 501-510, 1995, American Sleep Disorders Association and Sleep Research Society.

Schnader, "Increase of Pulmonary Artery Occlusion Pressure During Upper Airway Obstruction in Sleep Apnea, Case Reports," Critical Care Medicine, 1996, vol. 24, No. 2, pp. 354-358.

Schnapp et al., "Pulse Oximetry Uses and Abuses," Critical Care, Chest, vol. 98, No. 5, Nov. 1990, pp. 1244-1250.

Schneider et al., "Neural and local effects of hypoxia on cardiovascular responses to obstructive apnea," Journal Appl Physiol., Mar. 2000, vol. 88, No. 3, pp. 1093-1092 (Abstract).

Schoenberg et al., "Making ICU Alarms Meaningful: A Comparison of Traditional vs. Trend Based Algorithms," AMIA 1999, Annual Symposium (Abstract).

Schwab et al., "Upper Airway and Soft Tissue Structural Changes Induced by CPAP in Normal Subjects," American Journal Respiratory Critical Care Medicine, 1996, vol. 154, pp. 1110-1116.

Senn et al., "Monitoring Carbon Dioxide Tension and Arterial Oxygen Saturation by a Single Earlobe Sensor in Patients With Critical Illness or Sleep Apnea," Chest 2005, vol. 128, pp. 1291-1296.

Series et al., "Influence of Continuous Positive Airways Pressure on Sleep Apnea-Related Desaturation in Sleep Apnea Patients," Lung, 1992, vol. 170, pp. 281-290.

Series et al., "Prospective Evaluation of Nocturnal Oximetry for Detection of Sleep-Related Breathing Disturbances in Patients With Chronic Heart Failure," Chest 2005, vol. 127, pp. 1507-1514.

Series et al., "Utility of Nocturnal Home Oximetry for Case Finding in Patients with Suspected Sleep apnea Hypopnea Syndrome," Sep. 15, 1993, Annals of Internal Medicine, col. 119, p. 449-453.

Severinghaus et al., "Recent Developments in Pulse Oximetry," Anesthesiology, 1992, vol. 76, pp. 1018-1038.

Shamir et al., "Pulse oximetry plethsymographic waveform during changes in blood volume," British Journal of Anaesthesia, vol. 82(2), pp. 178-181, 1999, Great Britain.

Shepard, "Gas Exchange and Hemodynamics During Sleep," Medical Clinics of North America, vol. 69, No. 6, Nov. 1985, pp. 1243-1265.

Shephard et al., "Relationship of Ventricular Ectopy to Oxyhemoglobin Desaturation in Patients with Obstructive Sleep Apnea," Chest, vol. 88, No. 3, Sep. 1985, pp. 335-340, Northbrook, IL, USA.

Shephard et al., "Uvulopalatopharyngoplasty for Treatment of Obstructive Sleep Apnea," Mayo Clinic Proceedings, 1990, vol. 65, pp. 1260-1267.

Sher et al., "The Efficacy of Surgical Modifications of the Upper Airway in Adults With Obstructive Sleep Apnea Syndrome, An American Sleep Disorders Association Review," Sleep, Nov. 1995, vol. 19, No. 2, pp. 156-177.
Shinohara et al., "Visceral Fat Accumulation as an Important Risk Factor for Obstructive Sleep Apnoea Syndrome in Obese Subjects," Journal of Internal Medicine, 1997, vol. 241, pp. 11-18.
Shoemaker et al., "Incidence, Physiologic Description, Compensatory Mechanisms, and Therapeutic Implications of Monitored Events," Critical Care Medicine, Dec. 1989, vol. 17, No. 12, pp. 1277-1285.
Shoemaker et al., "Multicenter study of noninvasive monitoring systems as alternatives to invasive monitoring of acutely ill emergency patients," Chest, 1998, vol. 114, pp. 1643-1652.
Shoemaker et al., "Noninvasive Physiologic Monitoring of High-Risk Surgical Patients," Archives of Surgery, vol. 131, No. 7, Jul. 1996, pp. 732-737.
Shoemaker et al., "Prediction of Outcome and Severity of Illness by Analysis of the Frequency Distributions of Cardiorespiratory Variables," Critical Care Medicine, vol. 5, No. 2, Mar.-Apr. 1977, pp. 82-88.
Shoemaker et al., "Sequence of Physiologic Patterns in Surgical Septic Shock," Critical Care Medicine, Dec. 21, 1993, vol. 12, p. 1876-1889.
Shoemaker, "Cardiorespiratory Patterns in Complicated and Uncomplicated Septic Shock: Physiologic Alterations and Their Therapeutic Implications," Ann. Surg., Jul. 1971, vol. 174, No. 1, pp. 119-125.
Shoemaker, "Early Physiologic Patterns in Acurate Illness and Accidents: Toward a Concept of Circulatory Dysfunction and Shock Based on Invasive and Noninvasive Hemodynamic Monitoring," New Horizons, Nov. 1996, vol. 4, No. 4, pp. 395-412.
Shoemaker, "Temporal Physiologic Patterns of Shock and Circulatory Dysfunction Based on Early Descriptions by Invasive and Noninvasive Monitoring," New Horizons, vol. 4, No. 2, May 1996, pp. 300-318.
Shoemaker, W.C., "Oxygen Transport and Oxygen Metabolism in Shock and Critical Illness, Invasive and Noninvasive Monitoring of Circulatory Dysfunction and Shock," Critical Care Clinics, vol. 12, No. 4, Oct. 1996, pp. 939-969.
Siggaard-Andersen et al., "The Bohr effect and the Haldane effect," Scand J Clin Lab Invest, 1973, vol. 31, pp. 1-8.
Silverberg et al., "Essential and Secondary Hypertension and Sleep-Disordered Breathing: A Unifying Hypothesis," Journal of Human Hypertension, 1996, vol. 10, pp. 353-363.
Silverberg et al., "Sleep apnoea and hypertension. Active approach to detection of obstructive sleep apnoea is imperative," BMJ, Jul. 2000, vol. 22, pp. 321 (Abstract).
Silverberg, "The Joint National Committee on Prevention, Detection, Evaluation, and Treatment of High Blood Pressure and Obstructive Sleep Apnea: Let Their Silence Not Be Matched by the Silence of the Ordinary Physician," Arch Intern Med., Jun. 8, 1998, vol. 158, pp. 1272-1273.
Simmons et al., "The role of the central nervous system in septic shock. II. Hemodynamic, respiratory and metabolic effects of intracisternal or intraventricular endotoxin", Annals of Surgery, 1968, vol. 167, pp. 158-167.
Sin et al., "Effects of continuous positive airway pressure on cardiovascular outcomes in heart failure patients with and without Cheyne-Stokes respiration," Circulation, Jul. 2000, vol. 102, No. 1, pp. 61-66 (Abstract).
Sinex, "Pulse oximetry: principles and limitations," American Journal of Emergency Medicine, 1999, vol. 17, pp. 59-67.
Skjodt et al., "Screening for hypothyroidism in sleep apnea," American Journal of Respiratory & Critical Care Medicine, vol. 160, No. 2, pp. 732-735, Aug. 1999 (Abstract).
Slutsky et al., "Quantification of Oxygen Saturation During Episodic Hypoxemia," American Review of Respiratory Disease, 1980; 121:893-895.
Smith et al., "Hypoxemia During Sleep in Duchenne Muscular Dystrophy," American Review Respiratory Disorders, 1988, vol. 137, pp. 884-888.
Smyth et al., "Apneic Oxygenation Associated with Patient-Controlled Analgesia," Journal of Clinical Anesthesia, 1998, vol. 10, pp. 499-501.
Soto, "Cardiovascular manifestations of obstructive sleep apnea. Effects of the treatment," Rev Med Chil., [Article in Spanish], Sep. 1998, vol. 126, No. 9, pp. 1112-1116 (Abstract).
Soubani, "Noninvasive monitoring of oxygen and carbon dioxide," Am Journal of Emergency Medicine, 2001, vol. 19, pp. 141-146.
Spector, R., "Low-tech Screening for high-risk breathing disorder," http://healthlink.stanford.edu/healthlink/news2/lowtech.thml, Copyright 1996 Stanford University Medical Center News Bureau.
Staniforth et al., "Nocturnal desaturation in Patients with Stable Heart Failure," Heart, Apr. 1998, pp. 394-399.
Staniforth et al., "Nocturnal desaturation in patients with stable heart failure," Heart, Apr. 1998, vol. 79, No. 4, pp. 394-399 (Abstract).
Stebbens, V. A., "Oxygen saturation and breathing patterns in infancy. 1: Full term infants in the second month of life," Arch Dis Child, May 1991, vol. 66, No. 5, pp. 569-573 (Abstract).
Stegman et al., "Asymptomatic bradyarrhythmias as a marker for sleep apnea: appropriate recognition and treatment may reduce the need for pacemaker therapy," Pacing Clin Electrophysiol, Jun. 1996, vol. 19, No. 6, pp. 899-904 (Abstract).
Stradling et al., "Automatic Nasal Continuous Positive Airway Pressure Titration in the Laboratory: Patient Outcomes," Thorax, 1997, vol. 52, pp. 72-75.
Stradling et al., "Predictors and Prevalence of Obstructive Sleep Apnoea and Snoring in 1001 Middle Aged Men," Thorax, 1991, vol. 46, pp. 85-90.
Stradling et al., "Relation between systemic hypertension and sleep hypoxaemia or snoring: analysis in 748 men drawn from general practice," BMJ, vol. 300, Jan. 13, 1990, pp. 75-78.
Strohl et al., "Oxygen Saturation During Breath Holding and During Apneas in Sleep," Chest, Feb. 1984, vol. 85, No. 1, pp. 181-186.
Strohl et al., "Physiologic Basis of Therapy for Sleep Apnea, State of Art: Physiologic Basis of Therapy for Sleep Apnea," Am. Rev. Respir. Dis., 1986, vol. 134, pp. 791-802.
Strohl, Kingman P., "Consequences of Sleep-Disordered Breathing," Respiratory Care, Apr. 1998, vol. 43, No. 4, pp. 277-282.
Sullivan et al., "PCA Update, Unexpected Deaths of Patients Receiving Patient-Controlled Analgesia," Nov. 2001.
Sullivan et al., "Reversal of Obstructive Sleep Apnoea by Continuous Positive Airway Pressure applied through the Nares", The Lancet, Apr. 18, 1981, pp. 862, 865.
Svanborg et al., "A Limited Diagnostic Investigation for Obstructive Sleep Apnea Syndrome: Oximetry and Static Charge Sensitive Bed," Chest, 1990, vol. 98, pp. 1341-1345.
Svatikova et al., "Plasma brain natriuretic peptide in obstructive sleep apnea," American Journal Cardiology, Aug. 15, 2004, vol. 94, No. 4, pp. 529-532 (Abstract).
Szaboova et al., "Obstructive Sleep Apnea as a Cause of Dysrhythmia in Sudden Cardiac Death," Bratisl Lek Listy, Jul.-Aug. 1997, vol. 98, No. 7-8, pp. 448-453 (Abstract).
Tan et al., "Evaluation of Obstructive Sleep Apnea in Singapore Using Computerized Polygraphic Monitoring," Annals Academy of Medicine, Mar. 1991, vol. 20 No. 2, pp. 196-200.
Tanchaiswad, W., "Is Sudden Unexplained Nocturnal Death a Breathing Disorder?" Review Article, Psychiatry and Clinical Neurosciences, 1995, vol. 49, pp. 111-114.
Tang et al. "Peripheral neural modulation of endotoxin-induced hyperventilation," Critical Care Medicine, 1998, vol. 26, pp. 1558-1563.
Tanigawa et al., "Screening for sleep-disordered breathing at workplaces," Ind. Health, Jan. 2005, vol. 43, No. I, pp. 53-57 (Abstract).
Tatevossian et al., "Noninvasive Hemodynamic Monitoring for Early Warning of Adult Respiratory Distress Syndrome in Trauma Patients," Journal of Critical Care, Dec. 2000, vol. 15, No. 4, pp. 151-159.
Tatevossian et al., "Transcutaneous oxygen and C02 as early warning of tissue hypoxia and hemodynamic shock in critically ill emergency patients," Crit Care Med, Jul. 2000, vol. 28(7), pp. 2248-2253.

Teramoto et al., "Does the altered cardiovascular variability associated with obstructive sleep apnea contribute to development of cardiovascular disease in patients with obstructive sleep apnea syndrome?" Circulation, Dec. 21, 1999, vol. 100, No. 25, pp. e136-e137 (Abstract).

Teschler et al., "Automated Continuous Positive Airway Pressure Titration for Obstructive Sleep Apnea Syndrome," American Journal Respiratory Critical Care Medicine, 1996, vol. 154, pp. 734-740.

Teschler et al., "Influence of Moderate Alcohol Consumption on Obstructive Sleep Apnoea with and without AutoSet™ Nasal CPAP Therapy," European Respiratory Journal, 1996, vol. 9, pp. 2371-2377, Printed in United Kingdom.

The American Sleep Disorders Association Accreditation Committee, Standards for Accreditation of Sleep Disorders Centers, American Sleep Disorders Association, Rochester, MN, Mar. 1997, Revised Edition, pp. 1-17 (p. 16 missing).

Thorpy et al., "ASDA Standards of Practice, Practice Parameters for the Use of Portable Recording in the Assessment of Obstructive Sleep Apnea, Standards of Practice Committee of the American Sleep Disorders Associate," Sleep, 1994, vol. 17, No. 4, pp. 372-377.

Thorpy et al., "Practice Parameters for the Treatment of Obstructive Sleep Apnea in Adults: The Efficacy of Surgical Modifications of the Upper Airway, An American Sleep Disorders Association Review," Sleep, 1996, vol. 19, No. 2, pp. 152-155.

Thorpy et al., "Practice Parameters for the Treatment of Snoring and Obstructive Sleep Apnea with Oral Appliances, An American Sleep Disorders Association and Sleep Research Society," Sleep, 1995, vol. 18, No. 6, pp. 511-513.

Thorpy et al., "Practice Parameters for the Use of Actigraphy in the Clinical Assessment of Sleep Disorders, An American Sleep Disorders Association Report," Sleep, 1995, vol. 18, No. 4, pp. 285-287.

Thorpy et al., "Practice Parameters for the Use of Laser-assisted Uvulopalatoplasty, An American Sleep Disorders Association and Sleep Research Society," Sleep, 1994, vol. 17, No. 8, pp. 744-748.

Thorpy et al., "Practice Parameters for the Use of Polysomnography in the Evaluation of Insomnia, An American Sleep Disorders Association Report," Sleep, 1995, vol. 18, No. 1, pp. 55-57.

Thorpy, M., "The Clinical Use of the Multiple Sleep Latency Test, Report From the American sleep Disorders Association," Sleep, 1992, vol. 15, No. 3, pp. 268-276.

Timms et al., "Oxygen Saturation by Oximetry: Analysis by Microcomputer," Journal of Polysomographic Technology, Spring 1988, pp. 13-21.

Timms et al., and Profox Associates, Inc., Profox for the Bedside, Version 8SP Nov. 1992, Programs for Oximetry [IBM], User's Manual, Nov. 1992, 20 total pages.

Tkacova et al., "Effects of continuous positive airway pressure on obstructive sleep apnea and left ventricular afterload in patients with heart failure," Circulation, 1998, vol. 98, No. 21, pp. 2269-2275 (Abstract).

Tkacova, R., et al., Continuous positive airway pressure improves nocturnal barareflex sensitivity of patients with heart failure and obstructive sleep apnea., Journal Hypertension, Sep. 2000, vol. 18, No. 9, pp. 1257-1262 (Abstract).

Tobert et al., "Laboratory Medicine and Pathology, New Directions for Pulse Oximetry in Sleep Disorders," Mayo Clinic Proceedings, 1995, vol. 70, pp. 591, Rochester, Minnesota, USA.

Tobin et al., "Breathing Abnormalities During Sleep," Arch Intern Med, Jun. 1983, vol. 143, pp. 1221-1228.

Trang et al., "[B20] [Poster: 904] Masimo SetR Pulse Oximetry Improves Detection of Sleep Apnea-Related Hypoxemia," Nov. 2, 2001, C:/Masimo/Biblio, p. 1 of 1.

Tremel et al., "High prevalence and persistence of sleep apnoea in patients referred for acute left ventricular failure and medically treated over 2 months," European Heart Journal, Aug. 1999, vol. 20, No. 16, pp. 120-129.

Trinder et al., "Pathiophysiological interactions of ventilation, arousals, and blood pressure oscillations during Cheyne-Stokes respiration in patients with heart failure," American Journal Respiratory Critical Care Medicine, Sep. 2000, vol. 162, No. 3 Pt. 1, pp. 808-813 (Abstract).

Trupp et al., "Prevalence of sleep disordered breathing in a heart failure program," Congestive Heart Failure, Sep.-Oct. 2004, vol. 10, No. 5, pp. 217-220 (Abstract).

Trupp, R. J., "The heart of sleep: sleep-disordered breathing and heart failure," Journal Cardiovascular Nursing, Nov.-Dec. 2004, vol. 19, No. 6 Suppl, S67-74 (Abstract).

Ullmer et al., "Cheyne-stokes respiration or obstructive sleep apnoea: patterns of desaturation," Respiration, 2000, vol. 67, No. 2, p. 203 (Abstract).

VanBoxem et al., "Prevalence and severity of sleep disordered breathing in a group of morbidly obese patients," Netherlands Journal of Medicine, May 1999, vol. 54, No. 5, pp. 202-206 (Abstract).

Vanslyke et al., "Studies of Gas and Electrolyte Equilibria in Blood," Journal Biol. Chern., Oct. 1928, vol. 79, No. 2, pp. 781-798.

Verbraecken et al., "Chronic CO2 Drive in Patients with Obstructive Sleep Apnea and Effect of CPAP," Respiration Physiology, 1995, vol. 101, pp. 279-287.

Vgontzas et al., "Obesity Without Sleep Apnea is Associated with Daytime Sleepiness," Arch Intern Med, Jun. 22, 1998, vol. 158, pp. 1333-1337.

Vidhani et al., "Obstructive sleep apnoea syndrome: is this an overlooked cause of desaturation in the immediate postoperative period?" British Journal Anaesth, Apr. 1997, vol. 78, No. 4, pp. 442-443 (Abstract only).

Visser, B.F., "Pulmonary Diffusion of Carbon Dioxide," Med. Biol., Oct. 1960, vol. 5(1), pp. 155-166.

Waldhorn, R., "Surgical Treatment of Obstructive Sleep Apnea, Is Mandibular Surgery an Advance?" Chest, Dec. 1990, vol. 98(6), pp. 1315-1316.

Walker et al., "Uvulopalatopharyngoplasty Versus Laser-Assisted Uvulopalatoplasty for the Treatment of Obstructive Sleep Apnea," Laryngoscope, Jan. 1997, vol. 107, pp. 76-82.

Weber et al., "Low-Perfusion Resistant Pulse Oximetry," Journal of Clinical Monitoring, Jul. 1995, vol. 11, No. 4, p. 284 (Abstract).

Weiss et al., "Cardiovascular Morbidity in Obstructive Sleep Apnea, Progress in Cardiovascular Diseases," vol. 41, No. 5, Mar./Apr. 1999, pp. 367-376.

Wessendorft et al., "Sleep-disordered breathing among patients with first-ever stroke," Journal Neurology, Jan. 2000, vol. 247, No. 1, pp. 41-47 (Abstract only).

West et al., "Dynamic in Vivo Response Characteristics of Three Oximeters: Hewlett-Packard 4720IA, Biox IIII, and Nellcor N-100," Sleep, vol. 10, No. 3, 1987, pp. 263-271.

Westesson et al., "Morbidity after temporomandibular joint arthrography is lower than after removal of lower third molars," Oral Surgery Oral Medical Oral Pathol, 1990, vol. 70, pp. 2-4.

Wheatley et al., "Mechanical properties of the upper airway," Curr Opin Pulm Medicine, Nov. 1998, vol. 4, No. 6, pp. 363-369 (Abstract).

White et al., "Assessment of Accuracy and Analysis Time of a Novel Device to Monitor Sleep and Breathing in the Home," Sleep, vol. 18, No. 2, Feb. 1995, pp. 115-126.

White, David P., "Pathophysiology of Obstructive Sleep Apnoea, Sleep-Related Breathing Disorder-2," Thorax, 1995, vol. 50, pp. 797-804.

Whitelaw et al., "Clinical Usefulness of Home Oximetry Compared with Polysomnography Assessment of Sleep Apnea," American Journal Respiratory Critical Care Medicine, 2005, vol. 171, pp. 188-193, Internet address: www.atsjournals.org.

Whitman et al., "Comparison of the New Masimo SET V3 Technology with a Conventional Pulse Oximeter during Polysomnography," Sleep, 2001, vol. 24, pp. A412 (730.R).

Wiater et al., "Polysomnographic Standards for Infants and Children," Somnologie, vol. 4, pp. 39-42, 2000, Berlin—Wien.

Wieczorek et al., "Obstructive Sleep Apnea Uncovered After High Spiral Anesthesia: A Case Report, Cardiothoracic Anesthesia, Respiration and Airway," Canadian Journal of Anesthesia, 2005, vol. 52, No. 7, pp. 761-764.

Wilhoit et al., "Comparison of Indices Used to Detect Hypoventilation during Sleep," Respiration, 1985, vol. 47, pp. 237-242.

Wilkins et al., Egan's Fundamentals of Respiratory Care, Analysis and Monitoring of Gas Exchange, Book, Eighth Edition, Chapter 16, Section III, Capnography/Capnometry During Mechanical Ventilation, pp. 383-389.

Wilkinson, et al., "Effect of venous ozygenation on arterial desaturation rate during repetitive apneas in lambs," Respiration Physiology, 1995, vol. 101, pp. 321-331.

Williams et al., "Clinical Value of Polysomnography," The Lancet, May 2, 1992, vol. 339, p. 1113.

Williams et al., "Screening for Sleep Apnea Using Pulse Oximetry and a Clinical Score," Chest, Sep. 1991, vol. 100(3), pp. 631-635.

Wright et al., "Health effects of obstructive sleep apnoea and the effectiveness of continuous positive airways pressure: a systematic review of the research evidence," BMJ, Mar. 22, 1997, vol. 314, pp. 851-860.

Wright et al., "Letters, Obstructive Sleep Apnoea," Authors' reply, bmj.com, Jun. 26, 2001.

Wynne et al., "Disordered Breathing and Oxygen Desaturation During Sleep in Patients with Chronic Obstructive Lung Disease (COLD)," The American Journal of Medicine, Apr. 1979, vol. 66, pp. 573-579.

Yamakage et al., "Changes in respiratory pattern and arterial blood gases during sedation with propofol or midazolam in spinal anesthesia," Journal Clinical Anesth, Aug. 1999, vol. 11, No. 5, pp. 375-379 (Abstract).

Yantis, M. A., "Decreasing surgical risks for patients with obstructive sleep apnea," AORN Journal, Jul. 1998, vol. 68, No. 1, pp. 50-55 (Abstract).

Younes et al., "Chemical Control Stability in Patients with Obstructive Sleep Apnea," American Journal Respiratory Critical Care Medicine, 2001, vol. 163, pp. 1181-1190.

Young et al., "The Gender Bias in Sleep Apnea Diagnosis, Are Women Missed Because They Have Different Symptoms?" Original Investigations, Arch Intern Medicine, Nov. 25, 1996, vol. 156, pp. 2445-2451.

Zafar et al., "Choice of Oximeter Affects Apnea-Hypopnea Index," Chest, Jan. 2005, vol. 127(1), pp. 80-88, Clinical Investigations, www.chestjournal.org.

Zamarron et al., "Oximetry Spectral Analysis in the Diagnosis of Obstructive Sleep Apnoea," Clinical Science, 1999, vol. 97, pp. 467-473, Printed in Great Britain.

Zoccali et al., "Nocturnal Hypoxemia, Night-Day Arterial Pressure Changes and Left Ventricular Geometry in Dialysis Patients," Kidney International, vol. 53, 1998, pp. 1078-1084.

Zou et al., "Obstructive Apneic Events Induce Alpha-Receptor Mediated Digital Vasoconstriction," Sleep, 2004, vol. 27, No. 3, pp. 485-489.

Zucconi et al., "An unattended device for sleep-related breathing disorders: validation study in suspected obstructive sleep apnoea syndrome," European Respiratory Journal, 1996, vol. 9, pp. 1251-1256, Printed in United Kingdom.

Restriction Requirement for U.S. Appl. No. 11/455,488, mailed Sep. 16, 2010.

Restriction Requirement for U.S. Appl. No. 11/431,686, mailed Sep. 30, 2010.

Alattar et al., "Opioid-associated central sleep apnea: a case series," Sleep and Breathing, 2009, vol. 13(2), pp. 201-206.

Alian et al., "Evaluation of Rapid Response Team Flag-Alert Parameters," date unknown, 5 pages.

Al-Shawwa et al., "Defining Common Outcome Metrics Used in Obstructive Sleep Apnea," Sleep Medicine, 2008, vol. 12, pp. 449-461.

Anderson et al., "Data logging technology in ambulatory medical instrumentation," Physiological Measurement, vol. 22, 2001, R1-R13.

Antic et al., "PHOX2B mutation-confirmed congenital central hypoventilation syndrome: presentation in adulthood," Am. J. Respir Crit. Care Med., 2006, vol. 174(8), pp. 923-927.

Augusto, "Temporal Reasoning for Decision Support in Medicine," Artificial Intelligence in Medicine, 2005, vol. 33(1), pp. 1-24.

Barker, "Motion-resistant pulse oximetry: a comparison of new and old models," Anesth. Analg., 2002, vol. 95(4), pp. 967-972.

Bell, Monitor alarm fatigue, American Journal of Critical Care, 2010, vol. 19(1), pp. 38.

Bellomo et al. "Prospective controlled trial of effect of medical emergency team on postoperative morbidity and mortality rates," Crit. Care Med., 2004, vol. 32(4), pp. 916-921.

Berry et al., "Triazolam in Patients with Obstructive Sleep Apnea," American Journal of Respiratory and Critical Care Medicine, 1995, vol. 151, pp. 450-454.

Berwick et al., "IHI Replies to 'The 100,000 lives campaign: a scientific and policy review'," Jt. Comm. J. Qual. Patient. Saf., 2006, vol. 32, pp. 628-633.

Blair, "Hypocapnia and gram-negative bacteremic shock," Am. J. Surg., 1970, vol. 119(4), pp. 433-439.

Blair, "Acid-base balance in bacteremic shock," Archives of Internal Medicine, 1971, vol. 127, pp. 731-739.

Blanc et al., "Computerized Photo-plethysmography of the finger," Canadian Journal of Anaesthesia, 1993, vol. 40(3), pp. 271-278.

Bossink et al., "Prediction of Mortality in Febrile Medical Patients: How Useful Are Systemic Inflammatory Response Syndrome and Sepsis Criteria?" Chest, 1998, vol. 113, pp. 1533-1541.

Bouillon et al., "Opioid-induced respiratory depression is associated with increased tidal vol. variability," European Journal of Anaesthesiology, 2003, vol. 20(2), pp. 127-133.

Busquets et al., "Decreased Plasma Levels of Orexin-A in Sleep Apnea," Respiration, 2004, vol. 71, pp. 575-579.

Cacho et al., "Capnography is superior to pulse oximetry for the detection of respiratory depression during colonoscopy," Rev. Esp. Enferm. Dig., 2010, vol. 102(2), pp. 86-89.

Caruso et al., "On the modeling of drug induced respiratory depression in the non-steady-state," 30th Annual International Conference of the IEEE, Engineering in Medicine and Biology Society, 2008, pp. 5564-5568.

Casey et al., "Sleep-Related Hypoventilation/ Hypoxemic Syndromes," Chest, 2007, vol. 131, pp. 1936-1948.

Catley et al., "Pronounced, Episodic Oxygen Desaturation in the Postoperative Period: Its Association with Ventilatory Pattern and Analgesic Regimen," Anesthesiology, 1985, vol. 63, pp. 20-28.

Catling et al., "Respiratory effects of analgesia after cholecystectomy: comparison of continuous and intermittent papaveretum," British Medical Journal, 1980, vol. 281(6238), pp. 478-480.

Chan et al., "Rapid Response Teams: A Systematic Review and Meta-analysis," Archives of Internal Medicine, 2010, vol. 70(1), pp. 18-26.

Chan et al., "Hospital-wide Code Rates and Mortality Before and After Implementation of a Rapid Response Team," JAMA, 2008, vol. 300(21), pp. 2506-2513.

Chugh et al., "A Community-Based Evaluation of Sudden Death Associated with Therapeutic Levels of Methadone," Am. J. Med., 2008, vol. 121(1), pp. 66-71.

Davis et al., "Radio telemetry in patient monitoring," Anesthesiology, 1961, vol. 22, pp. 1010-1013.

Dempsey et al., "Pathophysiology of sleep apnea," Physiological Reviews, 2010, vol. 90(1), 47-112.

Devita et al., "Findings of the first consensus conference on medical emergency teams," Crit. Care Med., 2006, vol. 34, pp. 2463-2478.

Devita et al., "Use of Medical Emergency Team Response to Reduce Hospotal Cardiopulomonary Arrests," Qual. Saf. Health Care, 2004, vol. 13, pp. 251-254.

Dojat et al., "Scenario Recognition for Temporal Reasoning in Medical Domains," Artifical Intelligence in Medicine, 1998, vol. 14, pp. 139-155.

Duckitt et al., "Worthing physiological scoring system: derivation and validation of a physiological early-warning system for medical admissions. An observational, population-based single-centre study," British Journal of Anaesthesia, 2007, vol. 98(6), pp. 769-774.

Eckert et la., "Central Sleep Apnea: Pathophysiology and Treatment," Chest, 2007, vol. 131, pp. 595-607.

Eckert et al., "Pathophysiology of Adult Obstructive Sleep Apnea," Proc. Am. Thorac. Soc., 2008, vol. 5, pp. 144-153.

Edworthy et al., "Fewer but better auditory alarms will improve patient safety," Qual. Saf. Health Care., 2005, vol. 14(3), pp. 212-215.

Esbenshade et al., "Respiratory failure after endotoxin infusion in sheep: Lung mechanics and lung fluid balance," Journal of Applied Physiology, 1982, vol. 53(4), pp. 967-976.

Farney et al., "Sleep-Disordered Breathing Associated with Long-Term Opioid Therapy," Chest, 2003, vol. 123, pp. 632-639.

Finck et al., "Pharmacokinetics of Morphine; Effects of Hypercarbia on Serum and Brain Morphine Concentrations in the Dog," Anesthesiology, 1977, vol. 47(5), pp. 407-410.

Fletcher et al., "Pulmonary Edema Develops after Recurrent Obstructive Apneas," American Journal of Respiratory and Critical Care Medicine, 1999, vol. 160, pp. 1688-1696.

Freeman, "Neurogenic Orthostatic Hypotension," The New England Journal of Medicine, 2008, vol. 358, pp. 615-624.

Gami et al., "Obstructive sleep apnea, obesity, and the risk of incident atrial fibrillation," Journal of the American College of Cardiology, 2007, vol. 49(5), pp. 565-571.

Gillard et al., "Operating characteristics of the Finapress system to predict elevated left ventricular filing pressure," Clin. Cardiol., 2006, vol. 29(3), pp. 107-111.

Giuliano et al., "New-generation pulse oximetry in the care of critically ill patients," Am. J. Crit. Care, 2005, vol. 14(1), pp. 26-37.

Giuliano, "Physiological Monitoring for Critically Ill Patients: Testing a Predictive Model for the Early Detection of Sepsis," American Journal of Critical Care, 2007, vol. 16, pp. 122-130.

Goldhill et al., "A physiologically-based early warning score for ward patients: the association between score and outcome," Anaesthesia, 2005, vol. 60, pp. 547-553.

Graham et al., "Monitor alarm fatigue: standardizing use of physiological monitors and decreasing nuisance alarms," Am. J. Crit. Care., 2010, vol. 19(1), pp. 28-34.

Greer, "The temporal evolution of acute respiratory distress syndrome following shock," European Journal of Anaesthesiology, 2010, vol. 27(3), pp. 226-232.

Guo et al., "Early recognition of myxedematous respiratory failure in the elderly," American Journal of Emergency Medicine, 2009, vol. 27(2), pp. 212-215.

Guyenet, "The 2008 Carl Ludwig Lecture: retrotrapezoid nucleus, CO2, homeostasis, and breathing automaticity," J. Appl. Physiol., 2008, vol. 105, pp. 404-416.

Hajiha et al., "Opioid receptor mechanisms at the hypoglossal motor pool and effects on tongue muscle activity in vivo," The Journal of Physiology, 2009, vol. 587(11), pp. 2677-2692.

Hallowell et al., "Potentially life-threatening sleep apnea is unrecognized without aggressive evaluation," The American Journal of Surgery, 2007, vol. 193, pp. 364-367.

Harris et al., "Manifestations of Sepsis," Arch. Intern. Med., 1987, vol. 147, pp. 1895-1906.

Heitman et al., "Validation of Nasal Pressure for the Identification of Apneas/Hypopneas during Sleep," American Journal of Respiratory and Critical Care Medicine, 2002, vol. 166, pp. 386-391.

"High Resolution Pulse Oximetry (HRPO) Case Report," Patient Safety, Inc., Nov. 23, 2008, 7 pages.

Hillman et al., "The upper airway during anaesthesia," British Journal of Anaesthesia, 2003, vol. 91(1), pp. 31-39.

Hillman et al., "Sleep, anesthesia, and the upper airway," Seminars in Anesthesia, Perioperative Medicine and Pain, 2007, vol. 26, pp. 65-72.

Hinshaw, "Sepsis/septic shock: participation of the microcirculation: an abbreviated review," Critical Care Medicine, 1996, vol. 24(6), pp. 1072-1078.

Hospital Inpatients (Treatment or Unplanned Surgery), flowchart, date unknown, 2 pages.

Hravnak et al., "Defining the Incidence of Cardiorespiratory Instability in Patients in Step-Down Units Using an Electronic Integrated Monitoring System," Arch Intern Med., 2008, vol. 168(12), pp. 1300-1308.

Hutchison et al., "Capnography and Respiratory Depression," American Journal of Nursing, 2008, vol. 108(2), pp. 35-39.

Hwang et al., "Association of Sleep-Disordered Breathing With Postoperative Complications," Chest, 2008, vol. 133, pp. 1128-1134.

Imholz et al., "Continuous non-invasive blood pressure monitoring: reliability of Finapres device during the Valsalva manoeuvre," Cardiovascular Research, 1988, vol. 22, pp. 390-397.

Imholz et al., "Non-Invasive continuous finger blood pressure measurement during orthostatic stress compared to intra-arterial pressure," Cardiovascular Research, 1990, vol. 24, pp. 214-221.

Iscimen et al., "Risk factors for the development of acute lung injury in patients with septic shock: an observational cohort study," Crit. Care Med., 2008, vol. 36(5), pp. 1518-1522.

Ismail et al., "Integrated monitoring and analysis for early warning of patient deterioration," British Journal of Anaesthesia, 2007, vol. 98(1), pp. 149-152.

Isono, "Obstructive Sleep Apnea of Obese Adults," Anesthesiology, 2009, vol. 110, pp. 908-921.

Jabre et al., "Capnography monitoring in nonintubated patients with respiratory distress," Am. J. Emerg. Med., 2009, vol. 27(9), pp. 1056-1059.

Jacques et al., "Signs of critical conditions and emergency responses (SOCCER): A model for predicting adverse events in the inpatient setting," Resuscitation, 2006, vol. 69, pp. 175-183.

Jobin et al., "Predictive value of automated oxygen saturation analysis for the diagnosis and treatment of obstructive sleep apnoea in a home-based setting," Thorax, 2007, vol. 62, pp. 422-427.

Johnston et al., "Repetitive hypoxia rapidly depresses cardio-respiratory responses during active sleep but not quiet sleep in the newborn lamb," The Journal of Physiology, 1999, vol. 519, pp. 571-579.

Kaplan et al., "Uncovering System Errors Using a Rapid Response Team: Cross-Coverage Caught in the Crossfire," The Journal of Trauma, Injury, Infection and Critical Care, 2009, vol. 67(1), pp. 173-179.

Kato et al., "Incomplete Arousal Processes in Infants Who Were Victims of Sudden Death," American Journal of Respiratory and Critical Care Medicine, 2003, vol. 168, pp. 1298-1303.

Kause et al., A comparison of antecedents to cardiac arrests, deaths, and emergency intensive care admissions in Australia and New Zealand, and the United Kingdom—the Academia study, Resuscitation, 2004, vol. 62(3), pp. 275-282.

Kelleher, "Pulse oximetry," J. Clin. Monit., 1989, vol. 5(1), pp. 37-62.

Khoo et al., "Obstructive Sleep Apnea Presenting as Recurrent Cardiopulmonary Arrest," Sleep and Breathing, 2009, vol. 13, pp. 89-92.

Landrigan et al., "Temporal Trends in Rates of Patient Harm Resulting from Medical Care," The New England Journal of Medicine, 2010, vol. 363, pp. 2124-2134.

Lang et al., "Sustained hypermetabolic sepsis in rats: characterization of the model," Journal of Surgical Research, 1983, vol. 35(3), pp. 201-210.

Lanone, "Diaphragmatic fatigue during sepsis and septic shock," Intensive Care Medicine, 2005, vol. 31(12), pp. 1611-1617.

Le Jemtel et al., "Seek and Treat Obstructive Sleep Apnea in Heart Failure," Journal of the American College of Cardiology, 2007, vol. 49(15), pp. 1632-1633.

Lightdale et al., "Microstream Capnography Improves Patient Monitoring During Moderate Sedation: A Randomized, Controlled Trial," Pediatrics, 2006, vol. 117(6), pp. 1170-1178.

Littleton et al., "The pickwickian syndrome-obesity hypoventilation syndrome," Clinics in Chest Medicine, 2009, vol. 30(3), pp. 467-478.

Litvak et al., "Rethinking Rapid Response Teams," JAMA, 2010, vol. 304(12), pp. 1375-1376.

MacLean et al., "Patterns of septic shock in man: A detailed study of 56 patients," Annals of Surgery, 1967, vol. 166, pp. 543-562.

Maddox et al., "Clinical Experience with Patient-Controlled Analgesia Using Continuous Respiratory Monitoring and a Smart Infusion System," Am. J. Health-Syst. Pharm., 2006, vol. 63, pp. 157-164.

Manzke et al., "5-HT Receptors Avert Opioid-induced Breathing Depression without Loss of Analgesia," Science, 2003, vol. 301, pp. 226-229.

Marini, "Arterial base deficit in pulmonary embolism is an index of severity and diagnostic delay," Intern. Emerg. Med., 2010, vol. 5(3), pp. 235-243.

Matsuoka et al., "Pulmonary embolism during laparoscopic cholecystectomy detected by sudden decrease in end-tidal carbon dioxide pressure," Masui, 2001, vol. 50(1), pp. 42-45 (abstract only).

McGaughey et al., "Outreach and Early Warning Systems (EWS) for the prevention of intensive care admission and death of critically ill adult patients on general hospital wards," Cochrane Database Syst Rev., 2007, vol. 3.

McGillicuddy et al., "Evaluation of end-tidal carbon dioxide role in predicting elevated SOFA scores and lactic acidosis," Intern. Emerg. Med., 2009, vol. 4(1), pp. 41-44.

McKinney, "Alarm fatigue sets off bells, Mass. incident highlights need for protocols check," Modern Healthcare, 2010, vol. 40(15), pp. 14.

Michaelson et al., "Validations of a Portable Home Sleep Study With Twelve-Lead Polysomnography: Comparisons and Insights Into a Variable Gold Standard," Annals of Otology, Rhinology & Laryngology, 2006, vol. 115(11), pp. 802-809.

Mikkelsen, "Serum lactate is associated with mortality in severe sepsis independent of organ failure and shock," Crit. Care Med., 2009, vol. 37(5), pp. 1670-1677.

Mildh et al., "The concentration-effect relationship of the respiratory depressant effects of alfentanil and fentanyl," Anesthesia Analgesia, 2001, vol. 93(4), pp. 939-946.

Moldenhauer et al., "Clinical triggers: an alternative to a rapid response team," 2009, vol. 35(3), pp. 164-174.

Mora et al., "Sedative and ventilatory effects of midazolam infusion: effect of flumazenil reversal," Can. J. Anaesth., 1995, vol. 42(8), 677-684.

Moses, "The correlation and level of agreement between end-tidal and blood gas pCO2 in children with respiratory distress: a retrospective analysis," BMC Pediatrics, 2009, vol. 9(20), 6 pages.

Nakano et al., "A New Oximetry Algorithm for Screening of Sleep-Disordered Breathing," Therapeutic Research, 2005, vol. 26(5), pp. 1-7.

Newman-Toker et al., "Diagnostic Errors- the Next Frontier for Patient Safety," The Journal of the American Medical Association, 2009, vol. 301(10), pp. 1060-1062.

Nigro et al., "Validation of the WristOx 3100 oximeter for the diagnosis of sleep apnea/ hypopnea syndrome," Sleep Breath, 2008, 10 pages.

Ochroch et al., "The impact of continuous pulse oximetry monitoring on intensive care unit admissions from a postsurgical care floor," Anesth Analg, 2006, vol. 102(3), pp. 868-875.

Overdyk et al., "Continuous Oximetry/ Capnometry Monitoring Reveals Frequent Desaturation and Bradypnea During Patient-Controlled Analgesia," Anesthesia & Analgesia, 2007, vol. 105(2), pp. 412-418.

Palsson, "Changes in central hemodynamics during experimental septic shock in conscious rats," Circulatory Shock, 1987, vol. 22(1), pp. 65-72.

Pass, "Cardiopulmonary response of the rat to gram-negative bacteremia," Am. J. Physiol., 1984, vol. 246, H344-350.

Patil et al., "Neuromechanical control of upper airway patency during sleep," Journal of Applied Physiology, 2007, vol. 102, pp. 547-556.

Pedersen et al., "Pulse oximetry for perioperative monitoring," Cochrane Database of Systematic Reviews, 2009, vol. 7(4), CD002013.

Peppard et al., "The impact of obesity on oxygen desaturation during sleep-disordered breathing," Am. J. Respir. Crit. Care Med., 2009, vol. 180(8), pp. 788-793.

"Photoplethysmograph," Wikipedia, available at http://en.wikipedia.org/wiki/Photoplethysmography, printed on Dec. 8, 2010, 4 pages.

Qadeer et al., "Capnographic Monitoring of Respiratory Activity Improves Safety of Sedation for Endoscopic Cholangiopancreatography and Ultrasonography," Gastroenterology, 2009, vol. 136, pp. 1568-1576.

Redline et al., "The Scoring of Respiratory Events in Sleep: Reliability and Validity," Journal of Clinical Sleep Medicine, 2007, vol. 3(2), pp. 169-200.

Remmers et al., "Pathogenesis of Upper Airway Occlusion During Sleep," Journal of Applied Physiology, 1978, vol. 44(6), pp. 931-938.

Rothschild et al., "A Controlled Trial of a Rapid Response System in an Academic Medical Center," The Joint Commission Journal on Quality and Patient Safety, 2008, vol. 34(7), pp. 417-425.

Sakurai et al., " Low Plasma Orexin-A Levels Were Improved by Continuous Positive Airway Pressure Treatment in Patients with Severe Obstructive Sleep Apnea-Hypopnea Syndrome," Chest, 2005, vol. 127, pp. 731-737.

Saper et al., "The Sleep Switch: Hypothalamic Control of Sleep and Wakefulness," Trends in Neurosciences, 2001, vol. 24(12), pp. 726-731.

Seifer et al., "Mointoring Devices for Falls and Syncope," Clinics in Geriatric Medicine, 2002, vol. 18, pp. 295-306.

Seiker et al., "Carbon dioxide intoxication: the clinical syndrome, its etiology and management with particular reference to the use of mechanical respirators," Medicine, 1956, vol. 35(4), pp. 389-423.

Shelley, "Photoplethysmography: Beyond the Calculation of Arterial Oxygen Saturation and Heart Rate," The International Anesthesia Research Society, 2010, 30 pages.

Simmons et al., "Hyperventilation and respiratory alkalosis as signs of gram-negative bacteremia," JAMA, 1960, vol. 174(18), pp. 2196-2199.

Smith et al., "Hospital-wide physiological surveillance—a new approach to the early identification and management of the sick patient," Resuscitation, 2006, vol. 71, pp. 19-28.

Smith et al., "Review and preformance evaluation of aggregate weighted 'track and trigger' systems," Resuscitation, 2008, vol. 77, pp. 170-179.

Stead et al., "Computational Technology for Effective Health Care: Immediate Steps and Strategic Directions," National Research Council of the National Academies, 2009, 113 pages.

Stock et al., "The PaCO2 rate of rise in anesthetized patients with airway obstruction," J. Clin. Anesth., 1989, vol. 1(5), pp. 328-332.

Taenzer et al., "Impact of pulse oximetry surveillance on rescue events and intensive care unit transfer: a before-and-after concurrence study," Anesthesiology, 2010, vol. 112(2), pp. 282-287.

Tarassenko et al., "Integrated monitoring and analysis for early warning of patient deterioration," British Journal of Anaesthesia, 2006,vol. 97, pp. 64-68.

Tee et al., "Bench-to-bedside review: The MET syndrome—the challenges of researching and adopting medical emergency teams," Critical Care, 2008, vol. 12(1), 6 pages.

"The Doctors Advocate," The Doctors Company, Third Quarter 2010, 8 pages.

Tibballs et al., "Reduction of paediatric in-patient cardiac arrest and death with a medical emergency team: preliminary results," Arch. Dis. Child., 2005, vol. 90, pp. 1148-1152.

Valipour et al., "Some factors affecting cerebral tissue saturation during obstructive sleep apnoea," European Respiratory Journal, 2002, vol. 20, pp. 444-450.

Vandercar et al., "Sleep apnea syndromes: a potential contraindication for patient-controlled analgesia," Anesthesiology, 1991, vol. 74(3), pp. 623-624.

Van Lieshout et al., "Physical manoeuvres for combating orthostatic dizziness in autonomic failure," The Lancet, 1992, vol. 339, pp. 897-898.

Vazquez et al., "Automated Analysis of Digital Oximetry in the Diagnosis of Obstructive Sleep Apnoea," Thorax, 2000, vol. 55, pp. 302-307.

Ventetuolo et al., "Sepsis: A Clinical Update," Clinical Journal of the American Society of Nephrology, 2008, vol. 3, pp. 571-577.

Walker et al., "Chronic Opioid Use is a Risk Factor for the Development of Central Sleep Apnea and Ataxic Breathing," Journal of Clinical Sleep Medicine, 2007, vol. 3(5), pp. 455-462.

Wang et al., "Influence of Obstructive Sleep Apnea on Mortality in Patients with Heart Failure," Journal of the American College of Cardiology, 2007, vol. 49(15), pp. 1625-1631.

Watkinson et al., "A randomised controlled trial of the effect of continuous electronic physiological monitoring on the adverse event rate in high risk medical and surgical patients," Anaesthesia, 2006, vol. 61(11), pp. 1031-1039.

White, "Opioid-induced suppression of genioglossal muscle activity: is it clinically important?" J. Physiol., 2009, vol. 587, pp. 3421-3422.

Wiedemann et al.,The effect of sedation on pulmonary function Anaesthesist, 1995, vol. 44 Suppl 3, pp. S588-S593 (Abstract only).

Winters et al., "Rapid Response Systems: A systemic review," Crit. Care Med., 2007, vol. 35, pp. 1238-1243.

Winters et al., "Rapid response teams: Walk, don't run," JAMA, 2006, vol. 296, pp. 1645-1647.

Witting et al., "The sensitivity of room-air pulse oximetry in the detection of hypercapnia," Am. J. Emerg. Med., 2005, vol. 23(4), pp. 497-500.

Wittwer et al., "Role of Morphine's Metabolites in Analgesia: Concepts and Controversies," The AAPS Journal, 2006, vol. 8(2), Article 39, E348-E352.

Yegneswaran, "The importance of screening for obstructive sleep apnea before surgery," Letter to the Editor, Sleep Medicine, 2008, 1 page.

Younes, "Contributions of Upper Airway Mechanics and Control Mechanisms to Severity of Obstructive apnea," Am. J. Respir. Crit. Care Med., 2003, vol. 168, pp. 645-658.

Younes, "Role of Arousals in the Pathogenesis of Obstructive Sleep Apnea," American Journal of Respiratory and Critical Care Medicine, 2004, vol. 169, pp. 623-633.

Zhang et al., "Activation of opioid mu receptors in caudal medullary raphe region inhibits the ventilatory response to hypercapnia in anesthetized rats," Anesthesiology, 2007, vol. 107(2), pp. 288-297.

Official Action for U.S. Appl. No. 11/455,488, mailed Dec. 28, 2010.

Official Action for U.S. Appl. No. 11/431,686, mailed Jan. 21, 2011.

Official Action for U.S. Appl. No. 11/280,653, mailed Mar. 31, 2010.

Official Action for U.S. Appl. No. 11/280,653, mailed Dec. 1, 2010.

Official Action for U.S. Appl. No. 11/280,653, mailed Jun. 13, 2011 8 pages.

Notice of Allowance for U.S. Appl. No. 11/455,488, mailed Aug. 22, 2011 8 pages.

Official Action for U.S. Appl. No. 11/431,686, mailed Oct. 12, 2011 11 pages.

Notice of Allowance for U.S. Appl. No. 11/455,488, mailed Nov. 29, 2011 8 pages.

* cited by examiner

→ Inflection Point | Slope$^N$ - Slope$^{N-1}$ | > Selected Deviaton
⇒ Polarity Change

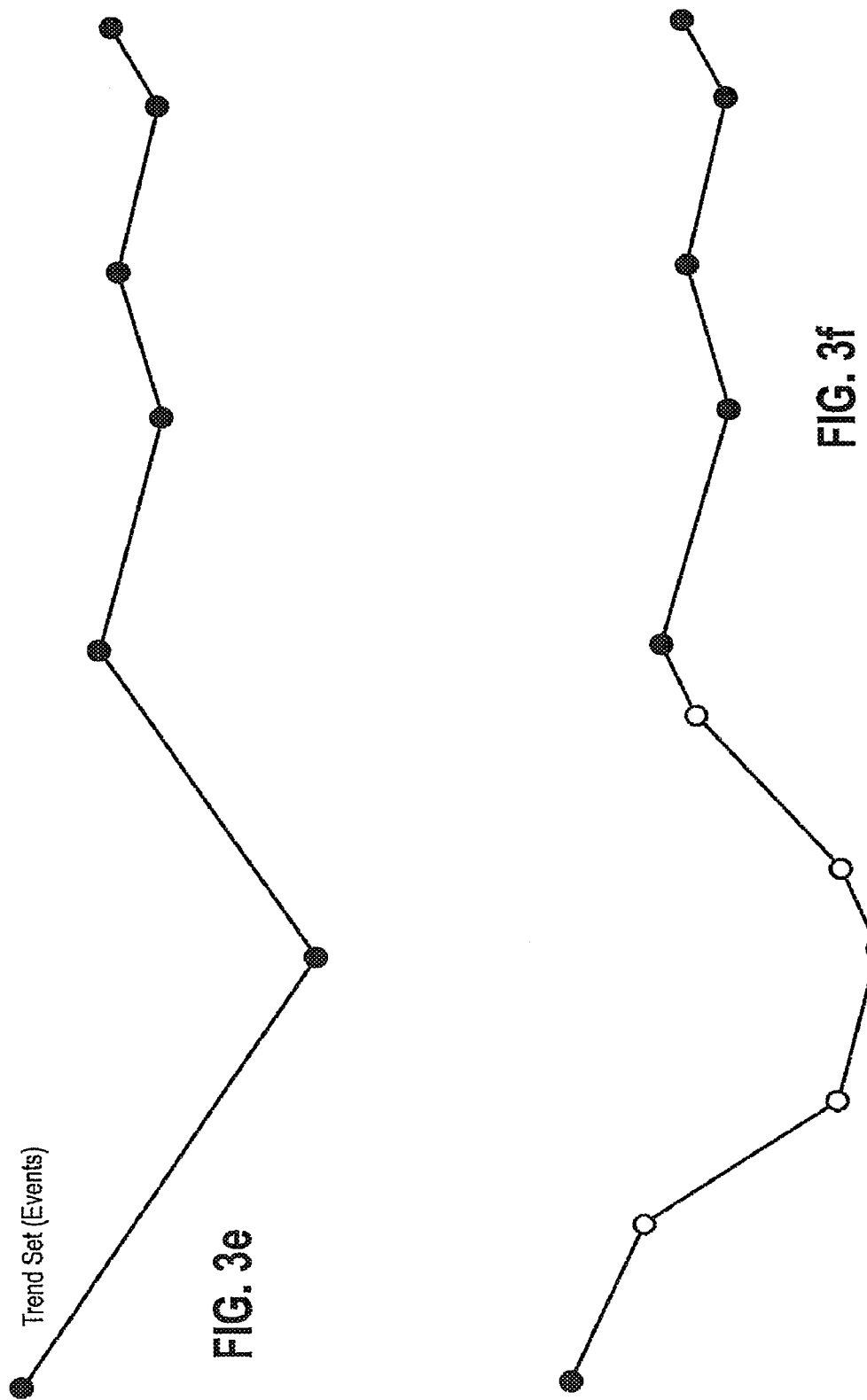

MICROPROCESSOR SYSTEM FOR THE ANALYSIS OF PHYSIOLOGIC DATASETS

APPLICATIONS INCORPORATED BY REFERENCE

This application is a continuation application of and claims priority to U.S. patent application Ser. No. 10/150,842, filed May 17, 2002, entitled "MICROPROCESSOR SYSTEM FOR THE ANALYSIS OF PHYSIOLOGIC AND FINANCIAL DATASETS". This application claims priority from U.S. Provisional Application No. 60/291,691 filed on May 17, 2001, claims priority from U.S. Provisional Application No. 60/291,687 filed on May 17, 2001, and is a continuation-in-part of U.S. patent application Ser. No. 09/628,655 filed Jul. 28, 2000 (now U.S. Pat. No. 6,609,016), which is a continuation-in-part of U.S. patent application Ser. No. 09/115,226 filed Jul. 14, 1998 (now U.S. Pat. No. 6,223,064), which is a continuation-in-part of U.S. patent application Ser. No. 08/789,460 filed Jan. 27, 1997 (now U.S. Pat. No. 5,891,023).

BACKGROUND

1. Field of the Invention

The present disclosure relates to an object-based system for the organization, analysis, and recognition of complex timed processes and the analysis and integration of time-series outputs of data sets and particularly physiologic data sets, and to the evaluation of the financial and physiologic datasets and the determination of relationships between them.

2. Background

The analysis of time-series data is widely used to characterize the behavior of a system. The following four general categories of approaches are commonly applied to achieve characterization of such a system and these provide a general background for the present disclosure. The approaches are illustrative both in their conceptualization, application, and limitations.

The first such approach represents a form of mathematical reductionism of the complexity through the application of a cascade of rules based on an anticipated relationship between the time-series output and a given set of system mechanisms. In this approach the operative mechanisms, data set characteristics, and intruding artifact are a priori defined to the best extent possible. Then a set of rules is applied to characterize and analyze the data set based on predicted relationships between the data set and the systems being characterized. Such systems often include cascading branches of decision-based algorithms, the complexity of which increase greatly in the presence of multiple interactive mechanisms. The reductionism approach is severely limited by the uncertainty and complexity, which rapidly emerges when a cascade of rules is applied to a highly interactive data set, when the signal to noise ratio is low, and/or when multiple data sets generated by complex and dynamically interactive systems are evaluated. These methods become inordinately more cumbersome as the complexity and number of time-series increases. In addition the subtlety of the interactive and dynamic relationships along and between datasets and the variations associated with the technique or tools of data collection often makes the cascading rules very difficult to a priori define.

The failure of simplification the analysis through mathematical reductionism to adequately characterize the complex systems generating such data sets, led to the perception that this failure resulted from specific limitations of a particular data format (usually the time domain format). In other words, the time-series was perceived to contain sufficient information to characterize the system but, it was thought, that the recognition of this information required reformatting into a different mathematical representation, which emphasized other hidden components which were specific for certain important system characteristics. This approach is exemplified by frequency processing methods, which reformat the time-series into frequency components, such as its sine components or wavelets, with the hope that patterns of specific frequency relationships within the system will emerge to be recognized. While often uncovering considerable useful information, this approach remains quite limited when applied to highly complex and interactive systems, because many complex relationships are poorly characterized by their frequency components, and it is often difficult to relate an output derived from frequency-based primitives to specific mechanisms operative within the system. In other words, the advantages associated with mathematically defined linkages between system mechanisms and the rules based analysis provided by reductionism is reduced by the data reformatting process for the purpose of frequency based signal processing as, for example, is provided by Fourier or wavelet transforms.

A third approach seeks to identify the patterns or relationships by repetitively reprocessing the time-series with a set of general comparative rules or by statistical processing. As with the data reformatting approach, the utility of this method in isolation (as embodied in neural network based analysis), is severely limited by dissociation of the output from the complex and interactive operative mechanisms, which define the output. With such processing, the relevant scope and characterization of the relationships of the output to the actual behavior of the dynamic interactions of the system is often quite limited. This limits the applicability of such processing in environments wherein the characterization of behavior of the system as a function by the output may be as important as the actual output values themselves.

A fourth approach has been to apply chaotic processing to the time-series. Again, like conventional signal processing, this method is applied with the expectation that some predictive pattern will emerge to be recognized. This technique shares several of the limitations noted for both frequency and statistical based data reformatting. In addition, as will be discussed, the application of this type of processing to physiologic signals is limited by redundant and interactive higher control which greatly limits the progression of the system to a state of uncontrolled chaotic behavior. Such systems operate in environments of substantial interactive control until the development of a severe disease state, a point at which the diagnostic information provided by processing often has less adjective utility relevant timely intervention.

The human physiologic system derives a large array of time-series outputs, which have substantial relevance when monitored over a finite time interval. The human can be considered the prototypic complex interactive system. These interactions and the mechanisms defining them have been the subject of intense research for over one hundred years and most of this work has been performed in the time domain. For this reason any approach toward the characterization of such a system needs to consider the value of engaging the body of knowledge, which relates to these mechanisms. This has been one of the reasons that reductionism has predominated in the analysis of physiologic signals. U.S. Pat. No. 5,765,563 to Vander Schaff, U.S. Pat. No. 5,803,066 to Rapoport, and U.S. Pat. No. 6,138,675 to Berthon-Jones show such simple cascade decision systems for processing physiologic signals. U.S. Pat. No. 5,751,911 to Goldman shows a real-time waveform analysis system, which utilizes neural networks to per-form various stages of the analysis. U.S. Pat. No. 6,144,877 to Depetrillo shows a processor-based method for determining statistical information for time-series data and for detecting a biological condition of a biological system from the statistical information. U.S. Pat. Nos. 5,782,240 and 5,730,144 to Katz show a system that applies chaos analyzers, which generate a time-series, vector representation of each monitored function and apply chaotic processing to identify certain events. All of these systems are deficient in that they are not able to adequately organize, order and analyze the true state of dynamic interaction operative in the generation of these signals.

Critical illness is one example of a dynamic timed process, which is poorly characterized by the above-noted conventional methods. When human physiologic stability is under threat, it is maintained by a complex array of interactive physiologic systems, which control the critical time dependent process of oxygen delivery to the organism. Each system (e.g. respiratory, cardiac or vascular) has multiple biochemical and/or mechanical controls, which operate together in a predictable manner to optimize oxygen delivery under conditions of threat. For example an increased oxygen requirement during infection causes the patient to increase oxygen delivery by lowering lung carbon dioxide through hyperventilation and the fall in carbon dioxide then causes the hemoglobin molecule to increase its affinity for oxygen thereby further enhancing oxygen delivery. In addition to the basic control of a single system, other systems interact with the originally affected system to produce a predictable pattern of response. For example, in the presence of infection, the cardiac system interacts with the respiratory system such that both the stroke volume and heart rate increase. In addition, the vascular system may respond with a reduction in arterial tone and an increase in venous tone, thereby both reducing impedance to the flow of oxygen to the tissues and shifting more blood into the arterial compartment.

Each system generally also has a plurality of predicable compensation responses to adjust for pathologic alteration or injury to the system and these responses interact between systems. For example the development of infectious injury to the lung will result in an increase in volume of ventilated gas to compensate for the loss of functional surface area. This increase in ventilation can then induce a synergistic increase in both stroke volume and heart rate.

Finally, a pathologic process altering one system will generally also induce an alteration in one or more other systems and these processes are all time dependent. Sub acute or acute life threatening conditions such as sepsis, pulmonary embolism, or hemorrhage generally affect the systems in cascades or predictable sequences which may have a time course range from as little as 20 seconds or more than 72 hours. For example, the brief development of airway collapse induces a fall in oxygen saturation, which then causes a compensatory hyperventilation response, which causes a rise in heart rate over as little as 20-30 seconds. An infection, on the other hand, has a more prolonged time course inducing a rise in respiration rate, a rise in heart rate, and then a progressive fall in oxygen saturation, a fall in respiration rate, and a finally a terminal fall in heart rate often over a course of 48-72 hours.

It can be seen therefore that each disease process engaging the organism causes the induction of a complex and interactive time-series of pathophysiologic perturbation and compensation. At the onset of the disease (such as early in the course of infection) the degree of physiologic change may be very slight and limited to one or two variables. As a disease progresses both the magnitude of perturbation and the number of systems involved increases. In addition to inducing a predictable range of perturbation, a particular disease process generally produces a specific range of progression and pattern of evolution as a function of injury, compensation, and system interaction. Furthermore, this multi-system complexity, which can be induced by initial pathologic involvement of a single system, is greatly magnified when a plurality of pathologic processes is present.

Despite the fact that these conditions represent some of the most important adversities affecting human beings, these pathologic processes are poorly characterized by even the most sophisticated of conventional monitors, which greatly oversimplify the processing and outputs. Perhaps this is due to the fact that this interactive complexity overwhelmed the developers of substantially all of the conventional physiologic signal-processing methods in the same way that it overwhelms the physicians and nurses at the bedside everyday. Hospital critical care patient monitors have generally been applied as warning devices upon threshold breach of specific critical parameters with the focus on the balance between timely warning of a potentially life threatening threshold breach and the mitigation of false alarms. However, during the pivotal time, early in the process of the evolution of critical illness, the compensatory responses limit the change in primary critical variables so that the user, monitoring these parameters in isolation, is often given a false sense of security. For this reason it cannot be enough to recognize and warn of the occurrence of a respiratory arrest, or hypotension, or hypoxia, or of a particular type of cardiac arrhythmia. To truly engage and characterize the processes present, a patient monitor must have capability to properly analyze, organize, and output in a quickly and easily understood format the true interactive state of critical illness. As discussed below, it is one of the purposes of the present disclosure to provide such a monitor.

SUMMARY OF DISCLOSED EMBODIMENTS

The present disclosure provides a system and method, which provide comprehensive organization and analysis of interactive complexity along and between pluralities of time-series. One embodiment of the present disclosure includes an objects-based method of iterative relational processing of time-series fragments or their derivatives along and between corresponding time-series. The system then applies an iterative comparison process of those fragments along and between a plurality time-series. In this way, the relationship of a wide range of characteristics of substantially any dynamic occurrence in one time-series can be compared to the same or other characteristics of substantially any dynamic occurrence along another portion of the same time-series or any of the processed corresponding time-series.

According to the present disclosure, a first time-series is processed to render a time-series first level derived from sequential time-series segments of the first series. The time-series first level is stored in a relational database, object database or object-relational database. The first time-series level is processed to render a second time-series level derived from the sequential time-series component of the first time-series level and these are stored in the relational database, object database or object-relational database. Additional levels are then derived as desired. The compositions of sequential time-series, which make up the first and second levels, are determined by the definitions selected for the respective segments from which each level is derived. Each time-series fragment is represented as a time-series object, and each more complex time-series object inherits the more basic characteristics of time-series objects from which they are derived.

The time course of sub acute and acute critical illness to point of death is highly variable and can range from 24-72 hours with toxic shock, to as little as 30 seconds with neonatal apnea. The present inventors recognized that, regardless of its time course, such a pathological occurrence will have a particular "conformation", which according to the present disclosure can be represented spatially by an object based processing system and method as a particular object or time-series of objects, as a function of the specific progression of the interactive components for the purpose of both processing, and animation. The present inventors also recognized that the development of such a processing system would be capable of organizing and analyzing the inordinate degree of dynamic complexity associated with the output from the biologic systems through the automatic incorporation of these time-series outputs into a highly organized relational, layered, object-based data structure. Finally, the inventors further recognized that because of the potentially rapid time course of these illnesses and the irreversible endpoint, that patient care monitors must provide a quickly and easily understood output, which gives the medical personnel a simplified and succinct analysis of these complex relationships that accurately reflects the interactive complexity faced by the patient's physiologic systems.

It has been suggested that the development of periodicity in a human physiologic system represents a simplification of that system. This concept is based on the perception that human interactive physiologic systems operate in an environment of chaos and that a partial loss of control simplifies the relationships, allowing simpler periodic relationships to emerge. However, there is considerable reason to believe that this is not the case. Patients entering an environment of lower partial pressure of oxygen, as at altitude, will develop periodicity of ventilation. This does not indicate a general simplification of the system but rather, one proposed operative mechanism for the emergence of this new pattern is that the pattern reflects the uncovering of a preexisting dynamic relationship between two controllers, which now, together determine ventilation in this new environment. At sea level the controller responding to oxygen was subordinate to the controller responding to carbon dioxide so that the periodicity was absent. This simple illustration serves to demonstrate the critical linkage between patient outputs and higher control and the criticality of comprehensively comparing dynamic relationships along and between signals to achieve a true picture of the operative physiology. While periodicities are, at times, clearly pathologic, their development in biologic systems, rather than a manifestation of simplification of physiological behavior, than the engagement of new, often represents the engagement of more rudimentary layers of protection of a particular organ function or range built into the control system. This illustration further demonstrates that a given physiologic signal, when monitored in isolation, may appear to exhibit totally unpredictable and chaotic behavior, but when considered in mathematical or graphical relation (as in phase space) to a plurality of corresponding interactive signals, and to the interactive control mechanisms of those corresponding signals, the behavior of the original, chaotic appearing, signal often becomes much more explicable.

In an example, consider a timed plot of oxygen saturation (SPO2) under heavy sedation during sleep. This state is often associated with a loss of the maintenance of a narrow control range of ventilation during sleep and with the loss of stability of the airway so that a plot of the oxygen saturation, in the presence of such deep sedation, shows a highly variable pattern, which often appears grossly unpredictable, with sustained falls in oxygen saturation intermixed with rapid falls and often seemingly random rapid corrections. However, there are definable limits or ranges of the signal, and generally definable patterns, which are definable within the background of a now highly variable SPO2 signal. It may be temping to define this behavior statistically or by a chaotic processor in the hope of defining some emerging patterns as a function of the mathematical behavior of that signal. However, when analyzed with the partial pressure of $CO_2$, the minute ventilation, and a plot of EEG activity the oxygen saturation values are seen as a subordinate signal to the airflow which is now being controlled by a dysfunctional control process, which process is being salvaged by a more coarse and rudimentary survival response mechanism. The apparently chaotic behavior is now seen as driven by a complex but predictable sequence of a plurality of dynamic interactive relationships between corresponding signals and the forces impacting them. Therefore, in the presence of a pathophysiologic process, the behavior and ranges of any given signal are optimally defined by the dynamic patterns of the interactive behavior of corresponding signals and their respective dynamic ranges.

A biologic system actually exploits the chaotic output of simple nonlinear relationships by defining control ranges, which are affected by variations in corresponding signals. This produces a great degree in diversity of dynamic physiologic response, which is beneficial in that it may favor survival of a particular subgroup, in the presence of a certain type of pathophysiologic threat. The present inventors noted that, while this diversity imparts greater complexity, this complexity can be ordered by the application of an iterative microprocessor system, which defines a given signal as a function of a range "dynamic normality". According to one embodiment of the present disclosure, each signal is defined as a function of its own dynamic range (and in relation to a predicted control range) and as a function of contemporaneously relevant relationships of the dynamic ranges of other corresponding signals (with respect to their respective control ranges).

In one embodiment, the present disclosure comprises a system and method for organizing and analyzing multiple time-series of parameters generated by a patient (as during critical illness) and outputting this analysis in readily understandable format. The preferred system is capable of simultaneously processing dynamic time-series of physiologic relationships in real time at multiple levels along each parameter and across multiple levels of different parameters. The present embodiments provide this level of interactive analysis specifically to match the complexity occurring during a pathologic occurrence. More specifically the present embodiments provide an analysis system and method, which analyses the true dynamic state of a biologic system and the interactive primary and compensatory perturbations defining that state. During health, the output of physiologic systems are maintained within tight variances. As will be discussed, using the signal processing system of the present the extent to which the signals are held within these tight variances are characterized as a function of their dynamic ranges of variance and the signals are further characterized as a function of their dynamic relationships along the time-series within a given signal and between a plurality of additional corresponding signals. As will be learned by the following disclosure, the optimal monitor of the human physiologic state during critical illness must be capable of analyzing time-series relationships along and between a plurality signals with the similar degree of analytic complexity as is operative in the biologic systems controlling the interactive responses which are inducing those signals, and capable of outputting an indication based on the analysis in a readily understandable format.

In the preferred embodiment this is provided as a dynamic format such as a two-dimensional or three-dimensional object animation, the configuration of which is related to the analysis output. The configurations of the animation changes with the analysis output, as this output changes over time in relation to changes in the patient's physiologic state. The animation thereby provides a succinct and dynamic summary rendering which organizes the complexity of the interactive components of the output so that they can be more readily understood and used at the bedside and for the purpose of patient management and education of medical staff relevant the application of time-series analysis in the assessment of disease. According to one embodiment of the present disclosure, the process proceeds by the following sequence;

Organize the multiple data streams defining the input into a hierarchy of time-series objects in an objects based data structure.

Analyze and compare of the objects along and across time-series,

Organize and summarize (and/or simplify) the output.

Animate and present the summarized output.

Take action based on the output.

Analyze and compare the new objects derived subsequent the action.

Adjust the action.

Repeat the cycle.

Calculate the expense and recourse utilization related to said output.

Using the above system, according to the present disclosure, a plurality of time-series of physiologic signals (including timed laboratory data) of a given physiologic process (such as sepsis) can have a particular conformational representation in three-dimensional space (as is shown in FIGS. 2a and 2b). This spatial representation comprises a summary of the relational data components, as analyzed, to diagnose a specific pathophysiologic process, to determine its progression, to define its severity, to monitor the response to treatment, and to simplify the representative output for the health care worker.

Two exemplary pathophysiologic processes (airway instability and sepsis) will be discussed below. Further, exemplary patient monitoring systems and methods for processing, organizing, analyzing, rendering and animating output, and taking action (including additional testing or treatment based on said determining) in accordance with present embodiments will be disclosed.

A major factor in the development of respiratory failure is airway instability, which results in air-way collapse during sedation, stroke, narcotics, or stupor. As illustrated in FIGS. 5a and 5b, such collapse occurs in dynamic cycles called apnea clusters affecting a range of physiologic signals. These apnea clusters are an example of a process, which, perhaps due to the dynamic interactive complexity of the time-series, is not recognized by conventional hospital processors. Yet subgroups of patients in the hospital may be at risk from this disorder. Patients with otherwise relatively stable airways may have instability induced by sedation or narcotics and it is desirable for this instability to be recognized in real time in the hospital so that the dose can be adjusted or the drug withheld upon the recognition of this development. Conventional patient monitors are neither configured to provide interpretive recognition of the cluster patterns indicative of airway and ventilation instability nor configured to provide interpretative recognition of the relationship between apnea clusters. In fact, such monitors often apply averaging algorithms, which attenuate the clusters. For these reasons thousands of patients each day enter and leave hospital-monitored units with unrecognized ventilation and airway instability.

This failure of conventional hospital based central patient monitors such as Agilent CMS, or the GE-Marquette Solar 8000, to automatically detect, and quantify obstructive sleep apnea or the cluster patterns indicative of airway instability can be seen as a major health care deficiency associated with a failure to address a long and unsatisfied need. Because sleep apnea is so common, the consequence of the failure of conventional hospital monitors to routinely recognize apnea clusters means that the diagnosis was missed in perhaps hundreds of thousands of patients who unknowingly have this disorder and who have been monitored in the hospital over the past decade. Many of these patients will never be diagnosed in their lifetime and will needlessly suffer with the complications of the disorder. For these patients, the diagnostic opportunity was missed and the health implications and risk of complications associated with undiagnosed airway instability and sleep apnea will persist in this group throughout the rest of their life simply because it was not recognized that simple modifications and programming of these devices could allow automatic recognition of this common disorder. A second group of patients may have a complication in the hospital due to the failure to timely recognize obstructive sleep or airway instability. Also an important opportunity to enhance the value of a conventional critical care monitor, to increase the efficiency of the diagnosis of obstructive sleep apnea, and to increase the revenue for the critical care monitoring companies marketing has been lost. Further an opportunity to increase hospital and/or physician revenue has been missed.

To understand the criticality of recognizing airway instability in real-time it is important to consider the significance of the combined effect that oxygen therapy and narcotics or sedation may have in the patient care environment in the hospital. For example, in the management of a post-operative obese patient after upper abdominal surgery, the patient may be at particular risk for increased airway instability in association with narcotic therapy in the 1st and 2nd post-operative day due to sleep deprivation, airway edema, and sedation. Indeed, many of these patients have significant sleep apnea prior to admission to the hospital which is unknown to the surgeon or the anesthesiologist due to the subtlety of symptoms. These patients, even with severe sleep apnea, are relatively safe at home because of an arousal response; however, in the hospital, narcotics and sedatives often remove this "safety net". The administration of post-operative narcotics can significantly increase airway instability and, therefore, place the patient at substantial risk. Many of these patients are placed on electrocardiographic monitoring but the alarms are generally set at high and low limits. Hypoxemia induced by airway instability generally does not produce marked levels of tachycardia; therefore, airway instability is poorly identified by simple electrocardiographic monitoring without the identification of specific clusters of the pulse rate. In addition, simple oximetry evaluation is also a poor method to identify airway instability. Conventional hospital oximeters often have averaging intervals, which attenuate the dynamic desaturations. Even when the clustered desaturations occur they are often thought to represent false alarms because they are brief when desaturations are recognized as potentially real this often results in the simple and often misguided addition of nasal oxygen. However, nasal oxygen may prolong the apneas and potentially increase functional airway instability. From a monitoring perspective, the addition of oxygen therapy can be seen to potentially hide the presence of significant airway instability by attenuation of the level of desaturation and reduction in the effectiveness of the oximeter as a monitoring tool in the diagnosis of this disorder.

Oxygen and sedatives can be seen as an undesirable combination in patients with severely unstable airways since the sedatives increase the apneas and the oxygen hides them from the oximeter. For all these reasons, as will be shown, according to the present disclosure, it is desirable to monitor for the specific cluster patterns, which are present during the administration of narcotics, or sedatives in patients with increased risk of airway instability.

The central drive to breathe, which is suppressed by sedatives or narcotics, basically controls two critical muscle groups: the upper airway "dilator muscles" and the diaphragm "pump muscles". The tone of both these muscle groups must be coordinated. A fall in tone from the brain controller to the airway dilators results in upper airway collapse. Alternatively, a fall in tone to the pump muscles causes hypoventilation.

There are two major factors which contribute to respiratory arrest in the presence of narcotic administration and sedation. The first and most traditionally considered potential effect of narcotics or sedation is the suppression of the drive to pump muscles. In this situation, airway instability may be less important than the reduced stimulation of the pump muscles, such as the diaphragm and chest wall, resulting in inadequate tidal volume and associated fall in minute ventilation and a progressive rise in carbon dioxide levels. The rise in carbon dioxide levels causes further suppression of the arousal response, therefore, potentially causing respiratory arrest. This first cause of respiratory arrest associated with sedation or narcotics has been the primary focus of previous efforts to monitor patients postoperatively for the purpose of minimization of respiratory arrests. Both oximetry and tidal CO2 monitoring have been used to attempt to identify and prevent this development. However, in the presence of oxygen administration, oximetry is a poor indicator of ventilation. In addition, patients may have a combined cause of ventilation failure induce by the presence of both upper airway instability and decreased diaphragm output. In particular, the rise in CO2 may increase instability of the respiratory control system in the brain and, therefore potentially increase the potential for upper airway instability.

The second factor causing respiratory arrest due to narcotics or sedatives relates to depression of drive to upper airway dilator muscles causing a reduction in upper airway tone. This reduction in airway tone results in dynamic airway instability and precipitates cluster cycles of airway collapse and recovery associated with the arousal response as the patient engages in a recurrent and cyclic process of arousal based rescue from each airway collapse. If, despite the development of significant cluster of airway collapse, the narcotic administration or sedation is continued, this can lead to further prolongation of the apneas and eventual respiratory arrest. There is, therefore, a dynamic interaction between suppression of respiratory drive, which results in hypoventilation and suppression of respiratory drive, which results in upper airway instability. At any given time, a patient may have a greater degree of upper airway instability or a greater degree of hypoventilation. The relative combination of these two events will determine the output of the monitor, with the former producing a simple trending rise (as with end tidal CO2) or fall (as with minute ventilation or oxygen saturation) and the latter producing a cluster output pattern.

Unfortunately, this has been one of the major limitations of carbon dioxide monitoring. The patients with significant upper airway obstruction are also the same patients who develop significant hypoventilation. The upper airway obstruction may result in drop out of the nasal carbon dioxide signal due to both the upper airway obstruction on one hand, or be due to conversion from nasal to oral breathing during a recovery from the upper airway obstruction on the other hand. Although breath by breath monitoring may show evidence of apnea, conversion from nasal to oral breathing can reduce the ability of the CO2 monitor to identity even severe hypoventilation in association with upper airway obstruction, especially if the signal is averaged or sampled at a low rate. For this reason, conventional tidal CO2 monitoring when applied with conventional monitors may be least effective when applied to patients at greatest risk (i.e., those patients with combined upper airway instability and hypoventilation).

As described in U.S. Pat. No. 6,223,064, the underlying cyclic physiologic process, which drives the perpetuation of a cluster of airway closures, can be exploited to recognize upper airway instability in real time. The underlying cyclic process, which defines the behavior of the unstable upper airway, is associated with precipitous chances in ventilation and attendant precipitous changes in monitored parameters, which reflect and/or are induced by such ventilation changes. For example, cycling episodes of airway collapse and recovery produces sequential precipitous changes in waveform output defining analogous cluster waveforms in the oximetry pulse tracing, the airflow amplitude tracing, the oximetry SPO2 tracing, the chest wall impedance tracing and the EKG pulse rate or R to R interval tracing.

The use of central hospital monitors generally connected to a plurality (often 5 or more) of patients through telemetry is a standard practice in hospitals. While the identification of sleep apnea in the hospital is relatively common, at the present time, this requires the application of additional monitors. The present inventors are not aware of any of the central patient monitors (such as those in wide use which utilize central telemetry), which provide the above functionality. This is inefficient, requires additional patient connections, is not automatic, and is often unavailable. According to another aspect of the present disclosure, the afore-referenced conventional hospital monitors are converted and programmed to provide a measurement and count of airflow attenuation and/ or oxygen desaturation and to compare that output with the chest wall impedance to routinely identify the presence of obstructive sleep apnea and to produce an overnight summary and formatted output for over reading for the physician which meets the standard of the billing code in that it includes airflow, oximetry, chest impedance, and EKG or body position. This can use conventional apnea recognition algorithms (as are well known in the art), the apnea recognition system of U.S. Pat. No. 6,223,064, or another system for recognizing sleep apnea.

The prior art does not teach or anticipate the conversion of these central hospital monitors to provide these functionalities despite the major advantage for national heath care, which can be immediately gained. However, the present inventors discovered and recognized that the addition of such functionality to central hospital monitors would quickly result in a profound advantage in efficiency, patient care, reduced cost, patient safety, and potentially enhances physician and hospital revenue thereby improving the method of doing the business of diagnosing and treating sleep apnea. The business of diagnosis of sleep apnea has long required additional equipment and would be greatly enhanced by the conversion and programming of central hospital monitors to provide this functionality. Moreover, the method of using the processor of a central hospital monitor to automatically detect obstructive sleep apnea and provide processor based interpretive indication of obstructive output and to output a summary suitable for interpretation to make a diagnosis of obstructive sleep apnea can result in the automatic diagnosis of sleep apnea for hundreds of thousands of patients who are presently completely unaware of the presence of this disorder, and greatly improves the conventional method of doing the business of diagnosing sleep apnea. This also allows the patient monitoring companies, which manufacture the central hospital monitors to enter the sleep apnea diagnostic market and to exploit that entry by providing telemetry connection of positive pressure devices to the primary processor or secondary processor of the carried telemetry unit so that positive pressure can be adjusted by the patient monitor. This is an important method of doing the business of treating sleep apnea since it provides the hospital monitoring company with the potential for proprietary connectivity between the patient monitors and/or the associated telemetry unit to the positive pressure devices thereby providing a favorable mechanism for doing the business of selling positive pressure devices through enhancement of market entry and the increase in the number of recognized cases.

According one aspect of the present disclosure, the recognition of sequential precipitous changes can be achieved by analyzing the spatial and/or temporal relationships between at least a portion of a waveform induced by at least a first apnea and at least a portion of a waveform induced by at least a second apnea. This can include the recognition of a cluster, which can compromise a high count of apneas with specified identifying features which occur within a short time interval along said waveform (such as 3 or more apneas within about 5-10 minutes) and/or can include the identification of a waveform pattern defined by a closely spaced apnea waveform or waveform clusters. Further, the recognition can include the identification of a spatial and/or temporal relationship defined by waveform clusters, which are generated by closely spaced sequential apneas due to cycling upper airway collapse and recovery. Using the above discoveries, typical standard hospital monitors can be improved to provide automatic recognition of apnea clusters indicative of upper airway instability and to provide an automatic visual or audible indication of the presence of such clusters and further to provide a visual or audible output and severity of this disorder thereby rendering the timely recognition and diagnosis of upper airway instability and obstructive sleep apnea as routine and automatic in the hospital as the diagnosis of other common diseases such as hypertension.

FIG. 5a illustrates the reentry process driving the propagation of apnea clusters. The physiologic basis for these clusters has been previously described in U.S. Pat. Nos. 5,891,023 and 6,223,064 (the disclosure of each of which is incorporated by reference as if completely disclosed herein). This cycle is present when the airway is unstable but the patient is capable of arousal. In this situation, in the sleeping or sedated patient, upon collapse of the airway, the patient rescues herself and precipitously opens the airway to recover by hypoventilation. However, if the airway instability remains after the arousal and rescue is over, the airway collapses again, only to be rescued again thereby producing a cluster of closely spaced apneas with distinct spatial, frequency and temporal waveform relationships between and within apneas wherein the physiologic process reenters again and again to produce a clustered output. According to the present disclosure, an apnea cluster is comprised of a plurality (two or more) of closely spaced apneas or hypopneas but the use of 3 or more apneas is preferred. The present invention includes recognition of apnea clusters in SPO2, pulse, chest wall impedance, blood pressure, airflow (including but not limited to exhaled carbon dioxide and air temperature), systolic time intervals, and electrocardiograph tracings including pulse rate and R to R interval plots and timed plots of ST segment position and chest wall and/or abdominal movements. For all of these waveforms the basic underlying cluster pattern is similar and the same basic core cluster pattern recognition system and method, according to the present disclosure, can be applied to recognize them.

The present disclosure further includes a system for defining the physiologic status of a patient during critical illness based on the comparison of a first parameter along a first monitored time interval defining a first timed data set to at least one other parameter along a second time interval, defining a second timed data set. The second time interval corresponds to the first time interval and can actually be the first time interval or another time interval. The second time interval corresponds to the effected physiologic output of the second parameter as inclined by the output of the first parameter during the first time interval. For example the first time interval can be a five to fifteen minute segment of timed airflow and the time interval can be a slightly delayed five to fifteen minute segment of timed oxygen saturation derived from the airflow which defined the dataset of the first time interval.

According another aspect of the present disclosure, the microprocessor identifies changes in the second parameter that are unexpected in relationship to the changes in the first parameter. For example, when the microprocessor identifies a pattern indicative of a progressive rise in minute ventilation associated with a progressive fall in oxygen saturation, a textual warning can be provided indicating physiologic divergence of the oxygen saturation and minute ventilation. For example, the term "divergent oxygen saturation" can be provided on the patient monitor indicating that an unexpected change in oxygen saturation has occurred in association with the ventilation output. The occurrence of such divergence is not necessarily a life threatening condition but can be an early warning of significant life threatening conditions such as pulmonary embolism or sepsis. If the patient has an attached apparatus which allows the actual minute ventilation to be quantitatively measured rather than trended then, divergence can be identified even when the oxygen saturation does not fall as defined by plotting the timed output of ventilation indexing oximetry as by formulas discussed in the U.S. patent applications (of one of the present inventors) entitled Medical Microprocessor System and Method for providing, a Ventilation Indexed Value 60/201,735 and Microprocessor system for the simplified diagnosis of sleep apnea Ser. No. 09/115,226 (the disclosure of each of which is incorporated herein by reference as if completely disclosed herein). Upon the identification of divergence, the time-series of other parameters, such as the temperature, white blood cell count and other lab tests, can be included to identify the most likely process causing the divergence.

One of the reasons that the identification of pathophysiologic divergence is important is that such identification provides earlier warning of disease. In addition, if the patient progresses to develop significantly low levels of a given parameter, such as oxygen saturation or pulse, it is useful to be able to go back and identify whether or not the patient experienced divergence of these parameters earlier since this can help identify whether it is a primary cardiac or pulmonary process which is evolving and indeed the time course of the physiologic process is provided by both diagnostic and therapeutic. Consider, for example, a patient experiencing significant drop in oxygen saturation and cardiac arrest. One purpose of the present disclosure is to provide an output indicative of whether or not this patient experienced a cardiac arrhythmia which precipitated the arrest or whether some antecedent pulmonary process occurred which caused the drop in oxygen saturation which then ultimately resulted in the cardiac arrhythmia and arrest. If the patient is being monitored by chest wall impedance, oximetry and EKG, all three parameters can be monitored for evidence of pathophysiologic divergence. If, according to the present disclosure, the processor identifies divergence of the oxygen saturation in association with a significant rise in minute ventilation, then consideration for bedside examination, chest x-ray, arterial blood gas measurement can all be carried out so that the relationship between cardiac and pulmonary compensation in this patient can be identified early rather than waiting until a threshold breach occurs in one single parameter. Since, with the use of conventional monitors, threshold breach of an alarm can be severely delayed or prevented by an active compensatory mechanism, such as hyperventilation, one advantage of the present disclosure is that the processor can provide warning as much as 4 to 8 hours earlier by identifying pathophysiologic divergence rather than waiting for the development of a threshold breach.

Another example of the value of monitor-based automatic divergence recognition, according to the present disclosure is provided by a patient who has experienced a very mild breach of the alarm threshold in association with significant physiologic divergence, such as a patient whose baseline oxygen saturation is 95% in association with a given baseline amplitude and frequency of minute ventilation as identified by the impedance monitor. For this patient, the fall in oxygen saturation over a period of two hours from 95% to 89% might be perceived by the nurse or house officer as representing only a mild change which warrants the addition of simple oxygen treatment by nasal cannula but no further investigation. However, if this same change is associated with marked physiologic divergence wherein the patient has experienced significant increase in the amplitude and frequency of the chest impedance, the microprocessor identification of significant pathophysiologic divergence can give the nurse or house officer cause to consider further performance of a blood gas, chest x-ray or further investigation of this otherwise modest fall in the oxygen saturation parameter.

It is noted that excessive sedation is unlikely to produce physiologic divergence since sedation generally results in a fall in minute ventilation, which will be associated with a fall in oxygen saturation if the patient is not receiving nasal oxygen. The lack of pathophysiologic divergence in association with a significant fall in oxygen saturation can provide diagnostic clues to the house officer.

In a preferred embodiment, the processor system can automatically output an indication of pathophysiologic divergence relating to timed data sets derived from sensors which measure oxygen saturation, ventilation, heart rate, plethesmographic pulse, and/or blood pressure to provide automatic comparisons of linked parameters in real time, as will be discussed. The indication can be provided in a two or three-dimensional graphical format in which the corresponding parameters are presented in summary graphical format such as a timed two-dimensional or three-dimensional animation. This allows the nurse or physician to immediately recognize pathophysiologic divergence.

According to another aspect of the disclosure, the comparison of signals can be used to define a mathematical relationship range between two parameters and the degree of variance from that range. This approach has substantial advantages over the simple comparison of a given signal with itself along a time-series to determine variability with respect to that signal (as is described in Griffin U.S. Pat. No. 6,216,032, the disclosure of which is incorporated by reference as if completely disclosed herein), which has been shown to correlate loosely with a diseased or aged physiologic system. The signal variability processing method of the prior art, which has been widely used with pulse rate, lacks specificity since variance in a given signal may have many causes. According to the present disclosure a plurality of signals are tracked to determine if the variability is present in all of the signals, to define the relationship between the signals with respect to that variability, and to determine if a particular signal (such as for example airflow) is the primary (first) signal to vary with other signals tracking the primary signal. For example, airway instability, sepsis, stroke, and congestive heart failure are all associated with a high degree of heart rate variability and this can be determined in relation to a baseline or by other known methods, however in the preferred embodiment the general variability of a plurality of signals is determined and these are matched to determine if a particular signal has a greater variability than the other signals, and more importantly the dynamic relationship between the signals is determined to identify the conformation of that variability. In this respect, for example, the pulse in sepsis in a neonate may show a high degree of variability by confirming that this variability is associated with a general multi-parameter conformation as shown in FIGS. 2a and 2b (and will be discussed in more detail) rather than a conformation of rapidly expanding and contracting parameters, as is typical of airway instability. In this way, the etiology of the pulse variability is much better identified. Variability is therefore defined in relation to which parameters are changing, whether they are changing together in a particular category of conformation indicative of a specific disease process, and the extent to which they follow anticipated subordinate behavior is identified. According to another aspect of the present disclosure, the time-series of the parameter "relationship variance" and the time-series of the "relationship variability" are analyzed as part of the cylindrical data matrix.

Early in the state of sepsis, airflow and heart rate variability begin to develop. However early the oxygen saturation is closely linked to the airflow tracking the airflow and showing little variance near the top of its range. As septic shock evolves, variability increases and the tight relationship between airflow and oxygen saturation begins to breakdown. In one embodiment, this relationship is analyzed, as time-series of the calculated variance of the airflow, variance of the heart rate, and variance of the oxygen saturation, along with the streaming time-series of objects of the original measured values. Timed calculated variability thereby comprising components of a cylindrical data matrix of objects analyzed according to the methods described herein for time-series analysis. Furthermore a time-series of the variance from a given relationship and the variability of that variance is derived and added to the data matrix. In an example, an index of the magnitude value of airflow in relation to the magnitude value of oxygen saturation and/heart rate is calculated for each data point (after adjusting for the delay) and a time-series of this index is derived. Then a time-series of the calculated variability of the index is derived and added to the data matrix. The slope or trend of the index of "airflow" and oxygen saturation will rise significantly as septic shock evolves and this can be correlated with the slope of the variability of the index. In comparison with septic shock in airway instability, time-series of these parameters shows a high degree of variability generally but a relatively low degree of variance of the indexed parameters associated with that variability (since despite their precipitous dynamic behavior, these parameters generally move together maintaining the basic relationships of physiologic subordinance). In addition to heart rate, a time-series of the plethesmographic pulse (as amplitude, ascending slope, area under the curve, etc.) variability and variance (as with continuous blood pressure or airflow) can be derived and incorporated with the data matrix for analysis and comparison to determine variability and variance relationships as well as to define the general collective conformation of the dynamic relationships of all of these parameters.

According to another aspect of the disclosure, the analysis of subsequent portions of a time-series can automatically be adjusted based on the output of the analysis of preceding portions of a time-series. In an example, with timed waveforms, such as SPO2, in clinical medicine, there are two situations: one in which motion is present wherein it is critical to mitigate the effect of motion on the waveform and a second situation in which motion is not present, wherein it would be optimal not to apply motion algorithms so that true accurate waveform can be reflected without smoothing. The application of motion algorithms on a continuous basis results in significant smoothing of the entire waveform even when motion is not present, thereby attenuating the optimal fidelity of the waveform and potentially hiding important short term precipitous changes. For example, the application of these algorithms results in modification of the slope of the desaturation and the slope of resaturation and affects the relative relationship between the desaturation and resaturation slopes. One embodiment of the present disclosure includes a conventional system and method for detecting motion. The system and can include the motion detection method, which are utilized by Masimo Incorporated or Nellcor Puritan Bennett Incorporated and are well known in the art. According to the present disclosure, the signal is processed in one of two ways. If motion is detected the signal is processed through a motion mitigation algorithm such as the Masimo SET, as is known in the art. Subsequently, this signal is processed with cluster analysis technology for the recognition of airway instability. The cluster analysis technology is adjusted to account for the effect of averaging on the slopes and the potential for averaging to attenuate mild desaturations. In the second instance, when no motion is detected, the output is processed with a shorter averaging interval of about 1 to 2 seconds. This produces optimal fidelity of the waveform. This waveform is then processed for evidence of airway instability using cluster recognition.

According to one aspect of the disclosure, a microprocessor system is provided for the recognition of specific dynamic patterns of interaction between a plurality of corresponding and related time-series, the system comprising a processor the processor programmed to: process a first time-series to produce a lower-level time-series of sequential time-series fragments derived from the first time-series, process the lower-level time-series to produce a higher-level time-series comprised of sequential time-series fragments from the lower-level time-series, process a second time-series, the second time-series being related to the first time-series, produce a second lower-level time-series of sequential time-series fragments derived from the second time-series, and identify a dynamic pattern of interaction between the first time-series and the second time-series. The system can be further programmed to process the lower-level time-series of the second time-series to: produce a higher-level time-series derived from sequential time-series fragments of the second lower-level time-series. The system can be programmed to process a third time-series, the third time-series being related to at least one of the first and the second time-series, to produce a third lower-level time-series of sequential time-series fragments derived from said third time-series. The system can be programmed to process the higher-level time-series to produce a complex-level time-series derived from sequential time-series fragments of said higher-level time-series. The time-series fragments of the first and second time-series can be stored in a relational database, the fragments of the higher-level time-series can comprise objects, the objects inheriting the characteristics of the objects of the lower-level time-series from which they are derived. The first and second time-series can comprise datasets of physiologic data points and the system can comprise a patient monitoring system wherein the dynamic pattern of interaction comprises pathophysiologic divergence.

In one presently preferred embodiment, the system comprises, a monitor having a plurality of sensors for positioning adjacent a patient and a processor programmed to: produce a first timed waveform based on a first physiologic parameter of the patient, produce a second timed waveform based on a second physiologic parameter which is generally subordinate to the first physiologic parameter so that the second parameter normally changes in response to changes in the first parameter, and identify pathophysiologic divergence of at least one of the first and second physiologic parameters in relationship to the other physiologic parameter. The system can be further programmed to output an indication of said divergence, calculate an index of said divergence and/or provide an indication based on said index. The first parameter can, for example, comprise an indication of the magnitude of timed ventilation of a patient which can, for example, be the amplitude and/or frequency of the variation in chest wall impedance and/or the amplitude and/or frequency of the variation in nasal pressure and/or the amplitude and frequency of the variation of at least one of the tidal carbon dioxide and/or the volume of ventilation or other measurable indicator. The second parameter can, for example, comprise a measure of oxygen saturation and can be pulse oximetry value or other measurable indicator of arterial oxygenation such as a continuous or intermittent measurement of partial pressure of oxygen.

Another aspect of the disclosure further includes a method of monitoring a patient comprising: monitoring a patient to produce a first timed waveform of a first physiologic parameter and a second timed waveform of a second physiologic parameter, the second physiologic parameter being physiologically subordinate to the first physiologic parameter, identifying a pattern indicative of divergence of at least one of said waveforms in relation to a physiologically expected pattern of the one of the other of said waveforms and outputting an indication of said divergence. The first timed waveform can be, for example defined by a time interval of greater than about 5-20 minutes. The first and second time-series can, for example, be physiologic time-series derived from airflow and pulse oximetry. The processor can comprise a primary processor, and the system can include a secondary processor and at least one of a diagnostic and treatment device, the primary processor being connectable to the secondary processor, the secondary processor being programmed to control at least one of the diagnostic and treatment device, the secondary processor being programmed to respond to the output of said primary processor. The primary processor can be programmed to adjust the said program of said secondary processor. The treatment device can be, for example, an airflow delivery system controlled by a secondary processor, the secondary processor being programmed to recognize hypopneas, the primary processor adjusting the program of said secondary processor based on the identifying. In another embodiment the treatment device can be an automatic defibrillator. The secondary processor can be mounted with at least one of the treatment and diagnostic device, the primary processor being detachable from the connection with the secondary processor. In one embodiment, the primary processor is a hospital patient monitor capable of monitoring and analyzing a plurality of different patient related signals, which include electrocardiographic signals. In an embodiment the primary processor is a polysomnography monitor capable of monitoring a plurality of different signals including encephalographic signals.

It is the purpose of the present disclosure to provide a monitor capable of organizing the complexity of the actual operative dynamic interactions of all of the signals both with respect to the absolute values, the degree of relative variation, and rate of variation along and across multiple levels of the processed output and, more specifically, along and across multiple levels of multiple signals.

It is further the purpose of the present disclosure to organize the interactive complexity defining the physiologic outputs generated by the affected physiologic systems, to recognize specific types and ranges of interactive pathophysiologic time-series occurrences, and to analyze the components and evolution of such occurrences, thereby providing a timely output which reflects the true interactive, multi-system process impacting the patient or to take automatic action base on the result of said analysis.

It is the purpose of the present disclosure to provide an iterative processing system and method which analyzes both waveforms and timed laboratory data and outputs the dynamic evolution of the interactive states of perturbation and compensation of physiologic systems in real-time to thereby provide a device which actually monitors and recognizes the true physiologic state of the patient.

It is the purpose of the present disclosure to provide an iterative object oriented waveform processing system, which can characterize, organize, and compare multiple signal levels across a plurality of signals by dividing each waveform level of each signal into objects for discretionary comparison within a relational database, object database or object-relational database It is the purpose of the present disclosure to provide a diagnostic system, which can convert conventional hospital-based central telemetry and hardwired monitoring systems to provide automatic processor based recognition of sleep apnea and airway instability and which can output the data sets in a summary format so that this can be over read by the physician so that sleep apnea can be automatically and routinely detected in a manner similar to that of other common diseases such as hypertension and diabetes.

It is the purpose of the present disclosure to provide a diagnostic system, which can convert conventional hospital-based central telemetry and hardwired monitoring systems to provide processor based recognition of sleep apnea and airway instability through the recognition of patterns of closely spaced apneas and/or hypopneas both in real time and in overnight interpretive format.

It is the purpose of the present disclosure to provide a system, which identifies, maps, and links waveform clusters of apneas from simultaneously derived timed signals of multiple parameters including chest wall impedance, pulse, airflow, exhaled carbon dioxide, systolic time intervals, oxygen saturation, EKG-ST segment level, and other parameters to enhance the real-time and overnight diagnosis of sleep apnea.

It is further the purpose of the present disclosure to provide timely, real-time indication such as a warning or alarm of the presence of apnea and/or hypopnea clusters so that nurses can be aware of the presence of a potentially dangerous instability of the upper airway during titration of sedatives and/or narcotics.

It is further the purpose of the present disclosure to provide a system for the recognition of airway instability for combined cluster mapping of a timed dataset of nasal oral pressure with tidal CO2 to identify clusters of conversion from nasal to oral breathing and to optimally recognize clusters indicative of airway instability in association with tidal CO2 measurement indicative of hypoventilation.

It is further the purpose of the present disclosure to identify pathophysiologic divergence of a plurality of physiologically linked parameters along a timed waveform over an extended period of time to provide earlier warning or to provide reinforcement of the significance of a specific threshold breach.

Another purpose of the present disclosure to identify an anomalous trend of a first respiratory output in relation to a second respiratory output wherein said first output is normally dependent on said second output to identify divergence of said first respiratory output in relationship to the expected trend of said first respiratory output based on the trend of said second output.

A further purpose of the present disclosure is to plot the prolonged slope of a first respiratory output in relationship to the prolonged slope of a second respiratory output and to identify divergence of said first respiratory output in relation to the slope said second respiratory output.

It is further the purpose of the present disclosure to provide a system, which automatically triggers testing (and comparison of the output) of a secondary intermittently testing monitor based on the recognition of an adverse trend of the timed dataset output of at least one continuously tested primary monitor.

Another purpose of the present disclosure is to provide recognition of lower airway obstruction (as with bronchospasm or chronic obstructive pulmonary disease) by exploiting the occurrence of the forced exhalation during the hyperventilation phase of recovery intervals after and/or between intermittent upper airway obstruction to identify obstructive flow patterns within the forced exhalation tracing and thereby identify lower airway obstruction superimposed on clustered upper airway obstruction.

It is another aspect of the present disclosure to provide a system that automatically customizes treatment algorithms or diagnostic algorithms based on the analysis of waveforms of the monitored parameters.

A further aspect of the present disclosure is to provide a method of doing business through linking a time-series of expense and billing data to a time-series of patient related outputs and exogenous actions applied to the patient so that the expense of each aspect of the patients care can be correlated with both the procedures and medications administered as well as the patient output both with respect to dynamic patterns of interaction and specific laboratory values or comparative results.

BRIEF DESCRIPTION OF THE DRAWINGS

FIG. 3e shows a time-series of trend parameters calculated to provide the trend (or polarity) analysis in accordance with present embodiments.

FIG. 3f shows one wave pattern of FIG. 3d, which can be derived from the utilization of user-defined object boundaries in accordance with present embodiments.

DETAILED DESCRIPTION

Figure 1A:
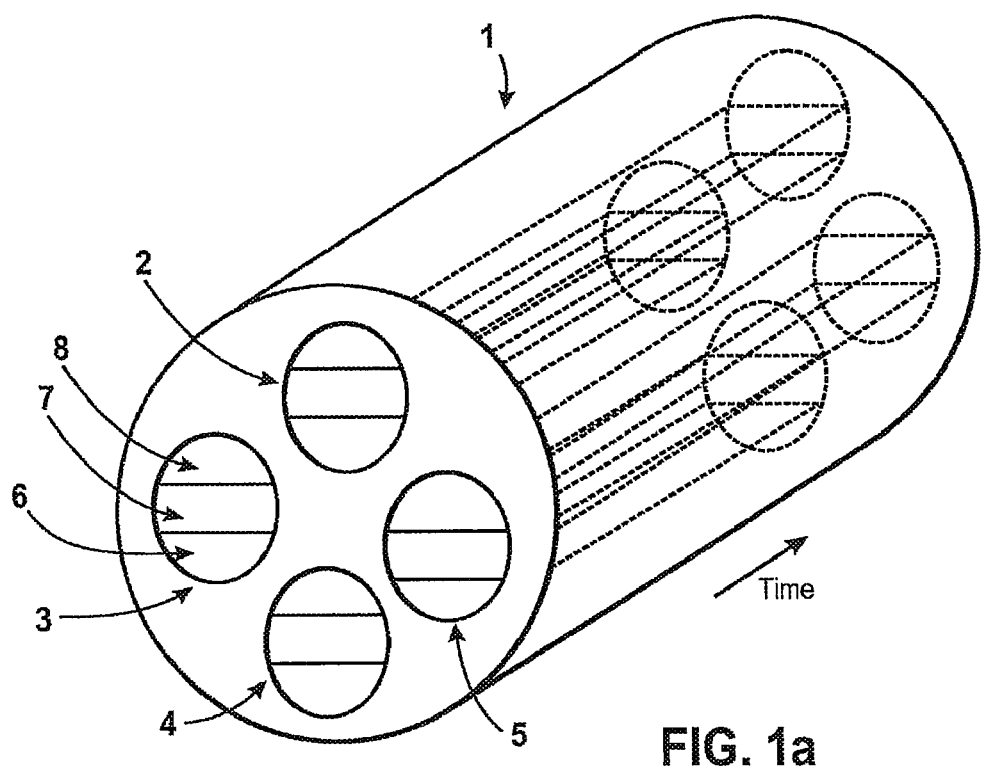
FIG. 1a shows a three-dimensional representation of the cylindrical data matrix comprised of corresponding, streaming, time-series of objects from four different timed data sets, with each of the four data sets divided into an ascending hierarchy of 3 levels in accordance with present embodiments.

The digital object processing system, according to the present disclosure, functions to provide multidimensional waveform object recognition both with respect to a single signal and multiple signals. Using this method, objects are identified and then compared and defined by, and with, objects from different levels and from different signals. FIG. 1a provides a representation of one presently preferred relational data processing structure of multiple time-series in accordance with present embodiments. As this representation shows, a plurality of time-series of objects are organized into different corresponding streams of objects, which can be conceptually represented as a cylindrical matrix of processed, analyzed, and objectified data 1 with time defining the axis along the length of the cylinder 1. In this example the cylinder 1 is comprised of the four time-series streams of processed objects each stream having three levels and all of the time-series and their respective levels are matched and stored together in a relational database, object database or object-relational database. Each streaming time-series of objects as from a single signal or source (e.g. airflow or oximetry, as in a matrix of physiologic signals) is represented in the main cylinder 1 by a smaller cylinder (2,3,4,5) and each of these smaller cylinders is comprised of a grouping of ascending levels of time-series of streaming objects (6,7,8) with the higher levels being derived from the level below it. The streaming objects in each ascending time-series level are more complex with each new level, and these more complex objects contain the simpler objects of the lower levels as will be described.

Figure 1B:
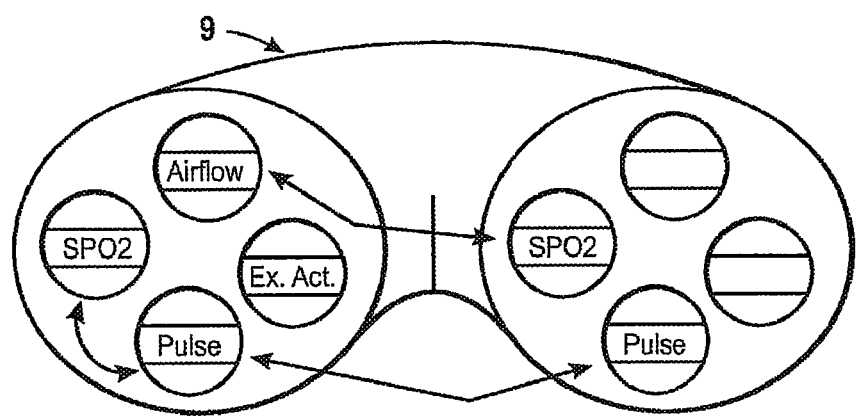
FIG. 1b shows a portion of FIG. 1a curved back upon it to illustrate the flexibility of object comparison between levels and different data sets within the same time period and across different levels of different data sets at different time periods to identify a dynamic pattern of interaction between the data sets in accordance with present embodiments.

FIG. 1b shows a cut section 9 of the cylindrical data matrix of FIG. 1a curved back upon itself to illustrate the one important advantage of organizing the data in this way in that each object from each grouping can be readily compared and matched to other objects along the grouping and can further be compared and matched to other objects from each other grouping. Furthermore, an object from one level of one signal at one time can be readily compared to an object from another level of a different signal at a different time. The time-series of streaming objects in FIG. 1b are airflow, SPO2, pulse, and a series of exogenous actions. This is a typical data structure, which would be used in accordance with present embodiments to monitor a patient at risk for sudden infant death syndrome and this will be discussed below in more detail.

Figure 2A:
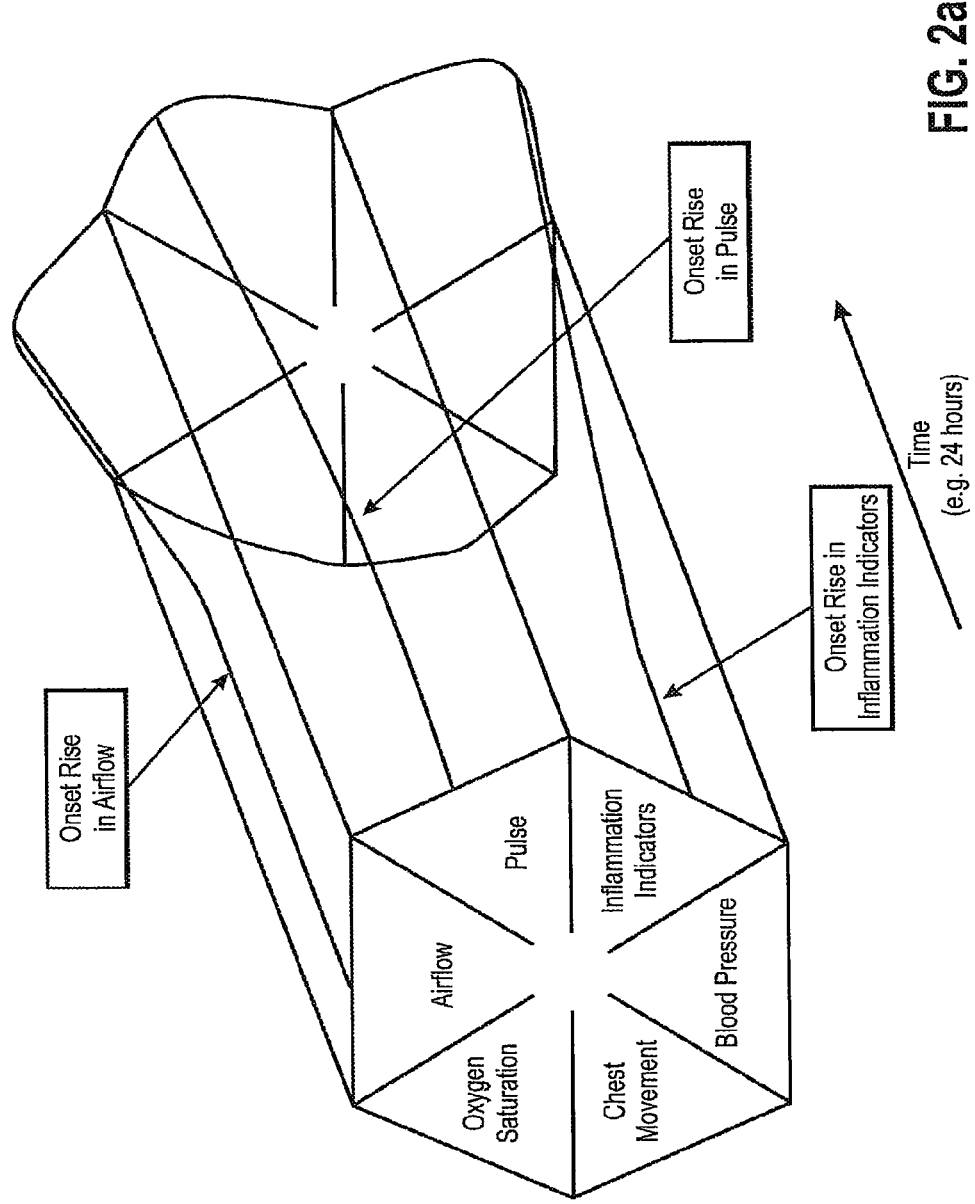
FIG. 2a shows a three-dimensional representation of collective conformation of corresponding time-series of objects of pulse (which can be heart rate and/or pulse amplitude), oxygen saturation, airflow, chest wall movement, blood pressure, and inflammatory indicators during early infection, organized in accordance with present embodiments.
Figure 2B:
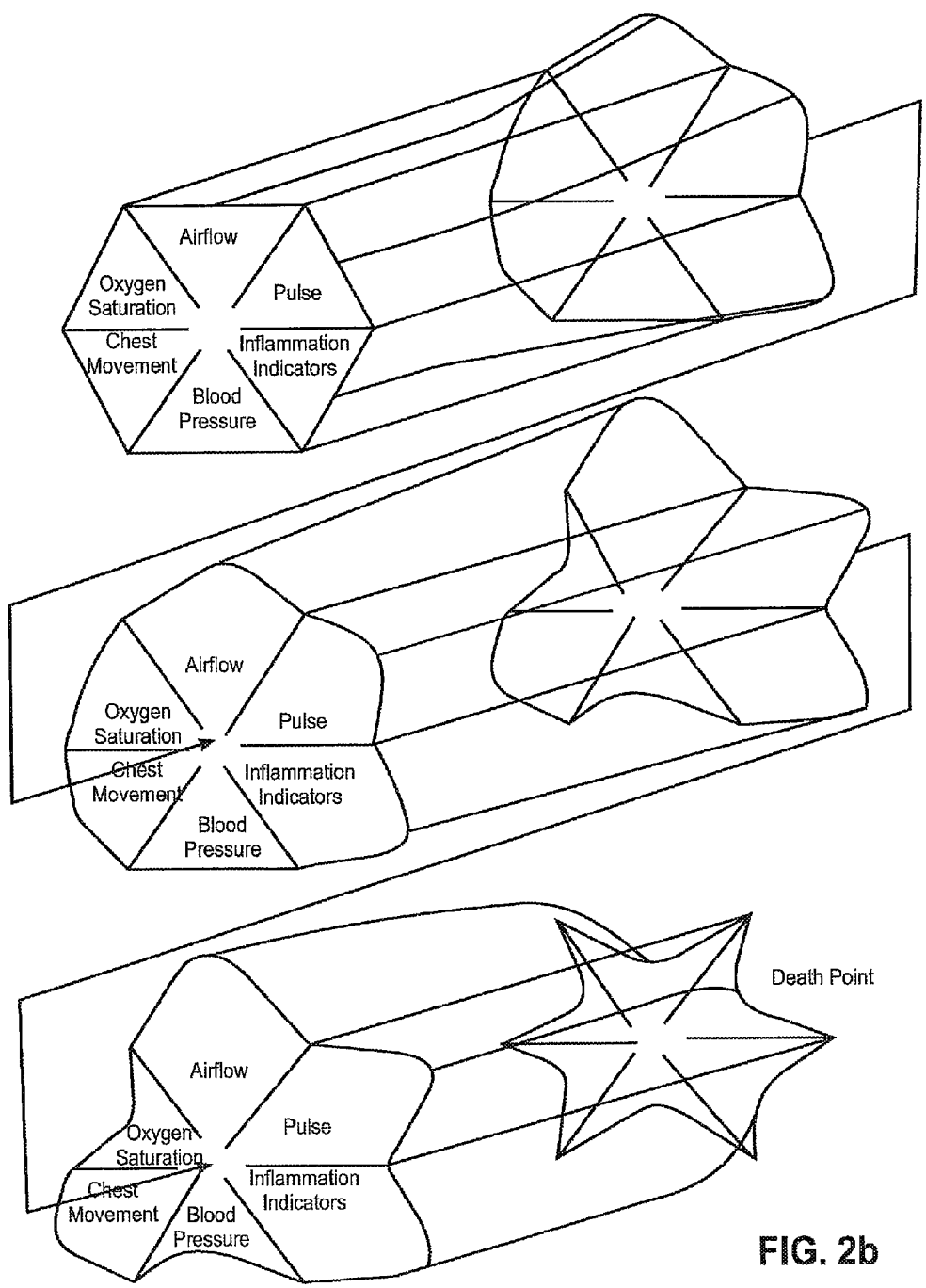
FIG. 2b shows the representation of the dynamic multi-parameter conformation of FIG. 2a extended through the evolution of septic shock to the death point (the point of pathologic divergence of the oxygen saturation and airflow is identified along this representation) in accordance with present embodiments.

Using this data structure, highly complex patterns and subtle relationships between interactive and interdependent streams of objects can be readily defined by searching the matched object streams as will be discussed. This allows for the recognition of the dynamic pattern interaction or conformation of the matrix of analyzed streaming interactive objects. FIG. 2a provides an illustration of one conformation of a collection of analyzed time-series during early sepsis. This is progressed through septic shock to the death point in FIG. 2b. Each particular expected conformation will be defined by the specific parameters chosen and the manner in which they are analyzed. In an extension of the example, a time-series of expenditures would reflect a significant increase in the slope of resource (as financial or other resources), which begins at a recognition point. If no recognition point occurs (i.e. the patient dies without the condition being diagnosed) the resource object time-series have a flat or even decreasing slope. The recognition of a specific dynamic pattern of interaction occurrence falling within a specified range is used to determine the presence and severity of a specific of a biologic or physical process, and its correlation with a time-series of resource allocation (such as timed expenditures) and a time-series of exogenous actions (such as pharmaceutical therapy or surgery) can be used to determine the cost and causes of a given dynamic pattern of interaction and to better define the efficacy of intervention. The conformation of FIGS. 2a and 2b can be seen as comprising a progressive expansion, evolving to divergence of the parameters and eventual precipitous collapse. This can be readily contrasted with the conformation of the cylindrical analyzed data matrix derived from the same analysis of the same time-series grouping during the state of evolving airway instability associated with excessive sequential or continuously infused dosing of sedation or narcotics. In this case the pattern is one of precipitous, cyclic, and convergent expansion and contraction with eventual terminal contraction.

The following discussion presents one embodiment of the present disclosure for application to the patient care environment to achieve organization and analysis of physiologic data and particularly physiologic signals and timed data sets of laboratory data from patients during a specific time period such as a hospitalization or perioperative period.

The interaction of physiologic signals and laboratory data is particularly complex, and requires a widely varied analysis to achieve comprehensive recognition of the many dynamic patterns of interaction indicative of potential threatening pathophysiologic events. This wide variation is due, in part, to the remarkable variation in both patient and disease related factors. Such analysis is best performed in real-time to provide timely intervention. To accomplish this level of organization and DPI identification through multiple levels of each data set or waveform and then across multiple levels of multiple data sets or waveforms, the system processes and orders all of the datasets from each system of the patient into a cylindrical matrix with each of the smaller cylinders containing the levels in a specific ascending fashion. An illustrative example of one preferred method sequence for organizing the data set of a single smaller cylinder (comprised of a single signal of airflow) is shown in FIGS. 3a-3g.

Figure 3A:
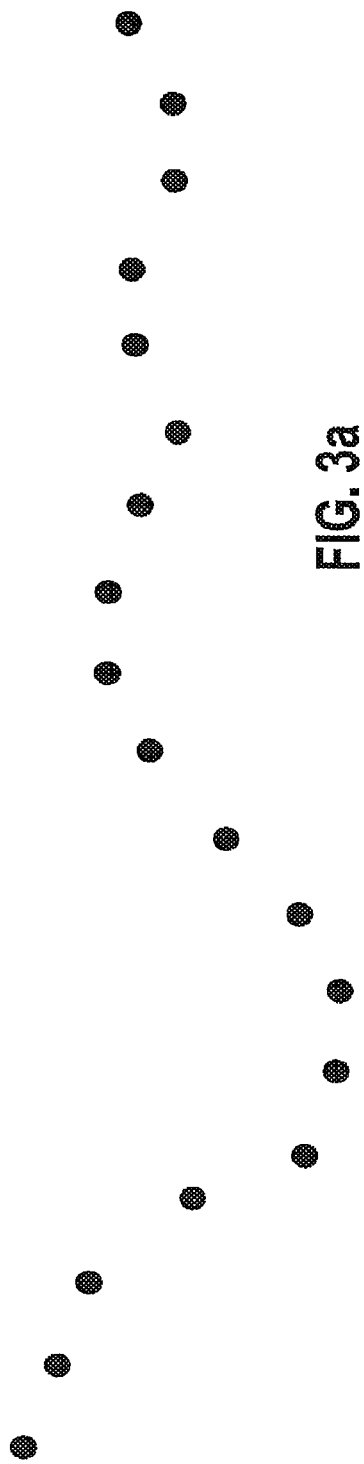
FIG. 3a shows a time-series of raw data points in accordance with present embodiments.
Figure 3B:
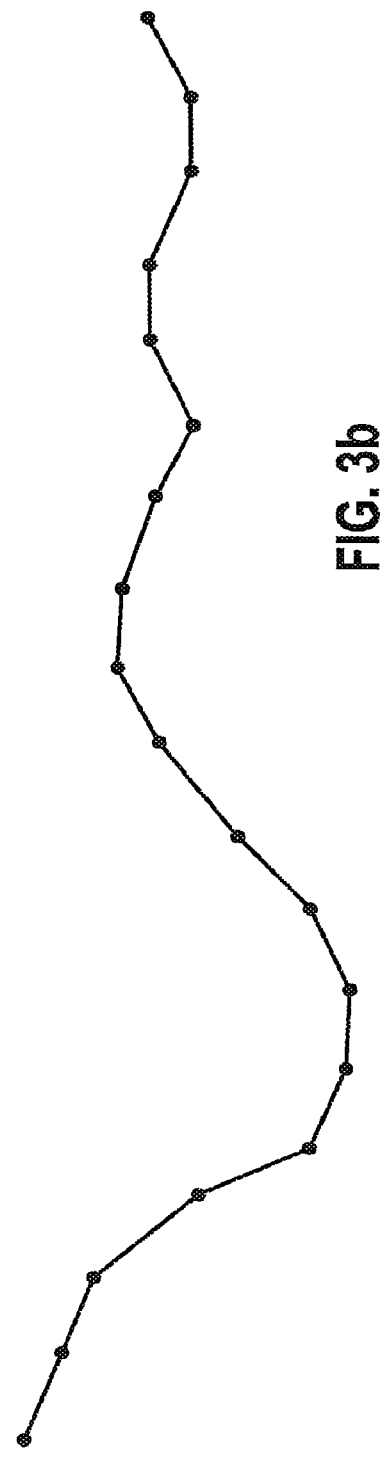
FIG. 3b shows a time-series of dipole objects in accordance with present embodiments.
Figure 3C:
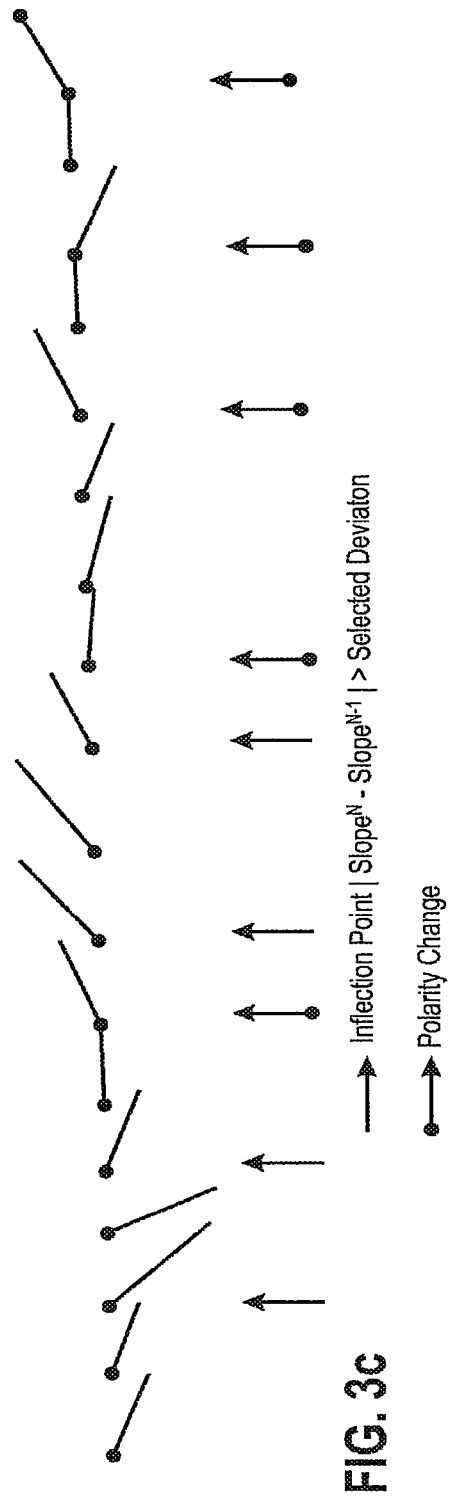
FIG. 3c shows a time-series of a slope set of the dipole objects of FIG. 3b, which removes the spatial attributes of the points and highlights relative change in accordance with present embodiments.
Figure 3D:
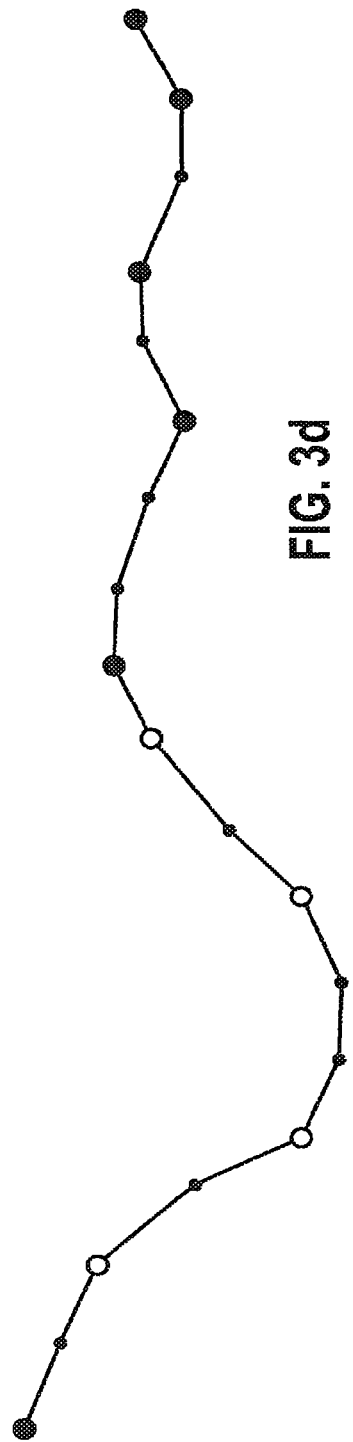
FIG. 3d shows a time-series with critical boundary points from which the wave pattern can be segmented and the objects can be derived and associated properties calculated in accordance with present embodiments.

According to this method, the processor first derives from a time-series of raw data points (FIG. 3a) a series of dipole objects with their associated polarities and slopes (FIG. 3b). As shown in FIG. 3c these dipoles can be represented as a slope set which removes the spatial attributes of the points and highlights relative change. As shown in FIG. 3c, various boundary types can be used to separate the dipoles into composite sequential objects and the figure shows three illustrative boundary types: pattern limits, inflection points, and polarity changes. As shown in FIG. 3d, the system now has the critical boundary points from which the wave pattern can be segmented and the composite objects can be derived and associated properties calculated. Although this is represented here as linear segments, each composite object is actually comprised of the original set of dipoles so that the user can choose to consider it a straight segment with one slope or a curved segment defined by the entire slope set of the segmented object. FIG. 3e shows how the "trend" composite objects can be identified to provide a simplified linear trend (or polarity) analysis.

Figure 3G:
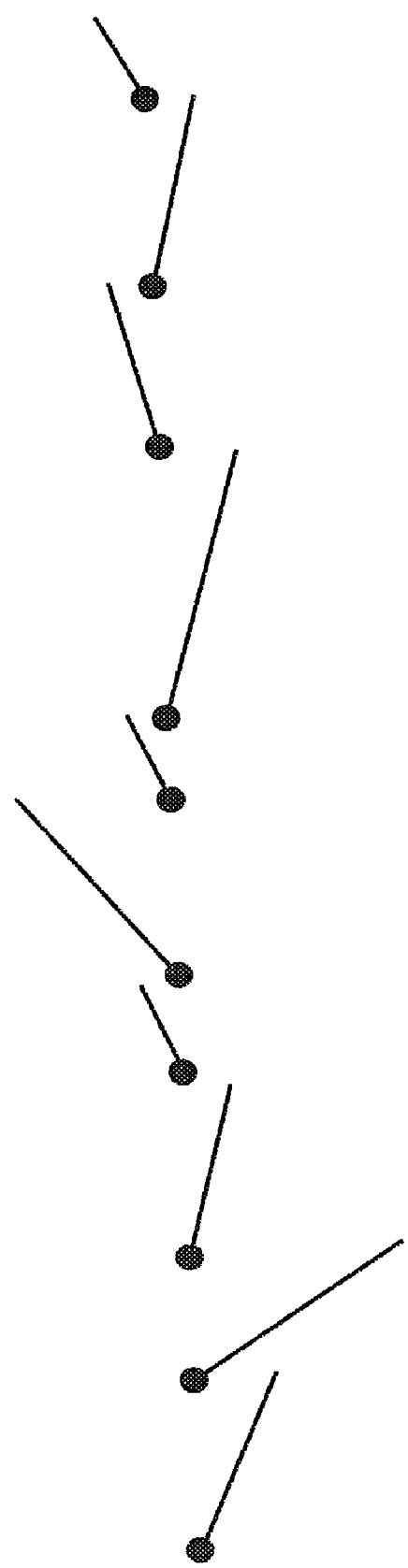
FIG. 3g shows a representation for the manipulation by the user for object slope or duration deviation specification in accordance with present embodiments.

Though the "trend" object set is very useful as shown in FIG. 3e the time-series can be segmented into other composite objects derived from the utilization of more or different user-defined boundary types. This can be useful even if the curved shapes can be analyzed in the simpler trend analysis because the selection of object boundaries at specific ranges or deflections helps to organize the objects as a direct function of changes in the physiologic output. In the example below, all three boundary types are employed to derive a wave pattern wire frame. The wire frame provides a simplified and very manageable view of the pattern and has boundary attributes that can be vary useful in waveform pattern searching. This type of object segmentation can be shown (FIG. 3f) as a set of object slopes with associated durations with the spatial relationships removed. As is shown in FIG. 3g, this provides a representation for the manipulation by the user for object slope or duration deviation specification. Such deviations may be specified specifically to individual segment objects or may be globally designated. Deviations may or may not be designated symmetrically. Multiple deviations can be specified per segment with scoring attributes (weighted deviations) to provide even more flexibility to the user to search for and correlate derived patterns. In some illustrated embodiments, figures may show specified deviations per segment (but not weighted deviations) for slope and duration.

In the above exemplary manner, the time-series can be organized with its associated objects and user-specified deviations, all of which are stored and categorized in a relational database, object database or object-relational database. Also as will be discussed, once processed, portions of such a time-series can then be applied as target search objects to other waveforms to search for similar objects and to score their similarity.

In accordance with present embodiments, those skilled in the art will recognize that complex curved shape variations can be specified in a similar way through the selection of specific ranges in variations of the dipole slope data set (FIG. 3c) defining the ranges of the curved target search object. (It should be noted that while the dipole set shown appears linearized, in fact, it can be seen that the dipoles can contain all of the information in the data points so that any curve present in the original raw data can be reproduced.) It is cumbersome to input such ranges for each dipole so this can be provided by specifying a curved shape and then moving a pointer adjacent a curved shape to identify a range of shapes defining a curved target search object.

Figure 4:
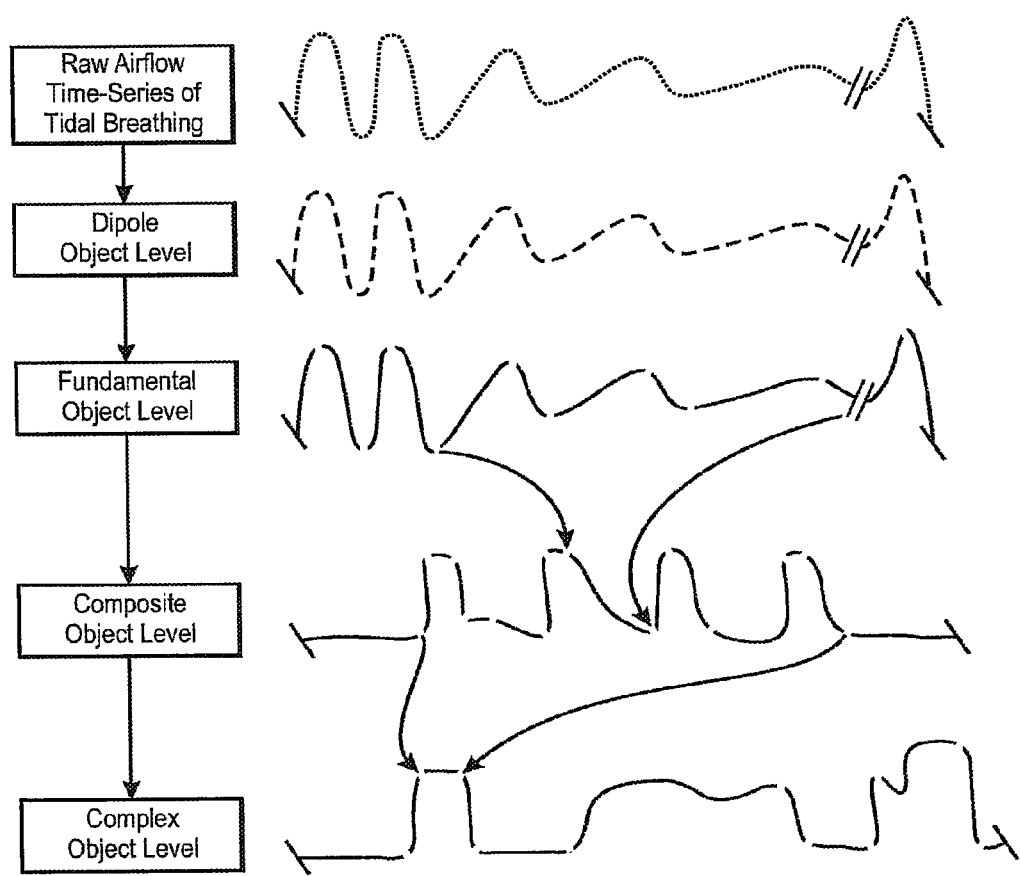
FIG. 4 shows the organization of the waveforms of FIG. 3 into ascending object levels in accordance with present embodiments.

FIG. 4 illustrates the ascending object processing levels according to the present disclosure, which are next applied to order the objects. In the preferred embodiment, these levels are defined for each signal and comparisons can be made across different levels between different signals. The first level is comprised of the raw data set. The data from this first level are then converted by the processor into a sequence of fundamental objects called dipoles to form the second (fundamental object) level. All of the objects, which will ultimately define complex multi-signal objects, are comprised of these sequential fundamental objects having the simple characteristics of slope polarity, and duration. At this level, the dipoles can be processed to achieve a "best fit" dipole matching of two or more signals (as will be discussed) and are used render the next level, called the "composite object level".

The composite object level is comprised of sequential and overlapping composite objects, which are composed of a specific sequence of slope dipoles as defined by selected search criteria. Each of these composite objects has similar primary characteristics of a slope duration, and polarity to the fundamental objects. However, for the composite objects, the characteristic of slope can comprise a time-series characteristic given as a slope dataset. The composite object level also has the characteristic of "intervening interval time-series" defined by a time-series of the intervals between the recognized or selected composite objects. At this level, a wide range of discretionary index characteristics can be derived from the comparison of basic characteristics of composite objects. Examples of such index characteristics include: a "shape characteristic" as derived from any specified portion of the slope dataset of the object, a "positional characteristic" as derived from, for example, the value of the lowest or highest points of the object, or a "dimensional value characteristic" as derived by calculating the absolute difference between specified data points such as the value of the lowest and the highest values of the object, or a "frequency characteristic" such as may be derived from performing a Fourier transform on the slope dataset of the object.

The next analysis level is called the "complex object level". In this level, each sequential complex object comprises a plurality of composite objects meeting specific criteria. A complex object has the same categories of primary characteristics and derived index characteristics as a composite object. A complex object also has the additional characteristics of "composite object frequency" or "composite object order" which can be used as search criteria defined by a selected frequency or order of composite object types, which are specified as defining a given complex object. A complex object also has additional higher-level characteristics defined by the time-series of the shapes, dimensional values, and positional characteristics of its component composite objects. As described for the composite objects, similar index characteristics of the complex objects can be derived from these characteristics for example: a "shape characteristic" derived from the mean rate of change along the dataset of the mean slopes of composite objects. Alternatively, characteristics or index characteristics may be combined with others. For example, a shape characteristic may be combined with a frequency characteristic to provide a time-series of a mathematical index of the slopes and the frequencies of the composite objects.

The next level, termed the "global objects level" is then derived from the time-series of complex objects. At this level, global characteristics are derived from the time-series datasets of complex objects (and all of their characteristics). At the global objects level, the processor can identify general specific patterns over many hours of time. An example of one specific pattern which is readily recognizable at this level would be a regular monotonous frequency of occurrence of one substantially complex object comprised of composite objects having alternating polarities, each with progressively rising or falling slope datasets. This pattern is typical of Cheyene-Stokes Respirations and is distinctly different from the pattern typical of upper airway instability at this global object level. Additional higher levels can be provided if desired as by a "comprehensive objects level" (not shown) which can include multiple overnight studies wherein a comprehensive object is comprised of a dataset of "global objects".

While FIG. 3b and FIG. 4 illustrate the levels of object derivations of a ventilation signal, in another example a similar hierarchical architecture can be derived for the timed data set of the pulse waveform (as from an arterial pressure monitor or the plethesmographic pulse). Here the fundamental level is provided by the pulse tracing itself and includes all the characteristics such as ascending and descending slope, amplitude, frequency, etc. This signal also includes the characteristic of pulse area (which, if applied to a precise signal such as the flow plot through the descending aorta, is analogous to tidal volume in the fundamental minute ventilation plot). When the pulse signal is plethesmographic, it is analogous to a less precise signal of ventilation such as nasal pressure or thermister derived airflow. With these less precise measurements, because the absolute values are not reliable indicators of cardiac output or minute ventilation, the complex spatial relationships along and between signals become more important than any absolute value of components of the signal (such as absolute amplitude of the ascending pulse or inspiration curve). In other word, the mathematical processing of multiple signals that are simply related to physiologic parameters (but are not a true measurement of those parameters) is best achieved by analyzing the complex spatial relationships along and between those signals. To achieve this purpose, according to the present disclosure, as with ventilation, the pulse signal is organized into a similar multi-level hierarchy of overlapping time-series of objects. Subsequently these are combined and compared with the processed objects of respiration to derive a unified object time-series defined by multiple corresponding data sets.

Figure 5A:
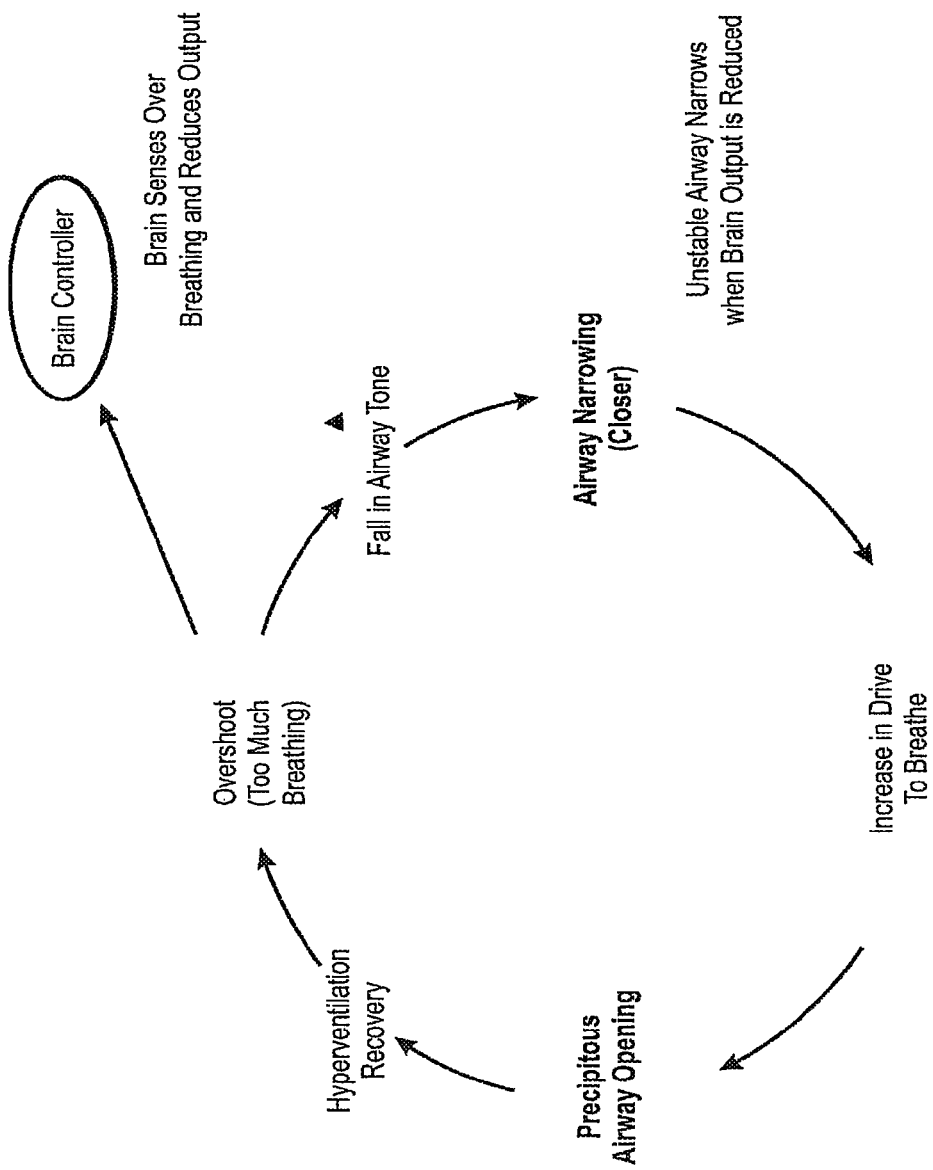
FIG. 5a shows an illustration of the complexity of the mechanisms defining the timed interactions of physiologic systems induced by upper airway instability, which the present inventor calls an "apnea cluster reentry cycle" in accordance with present embodiments.
Figure 5B:
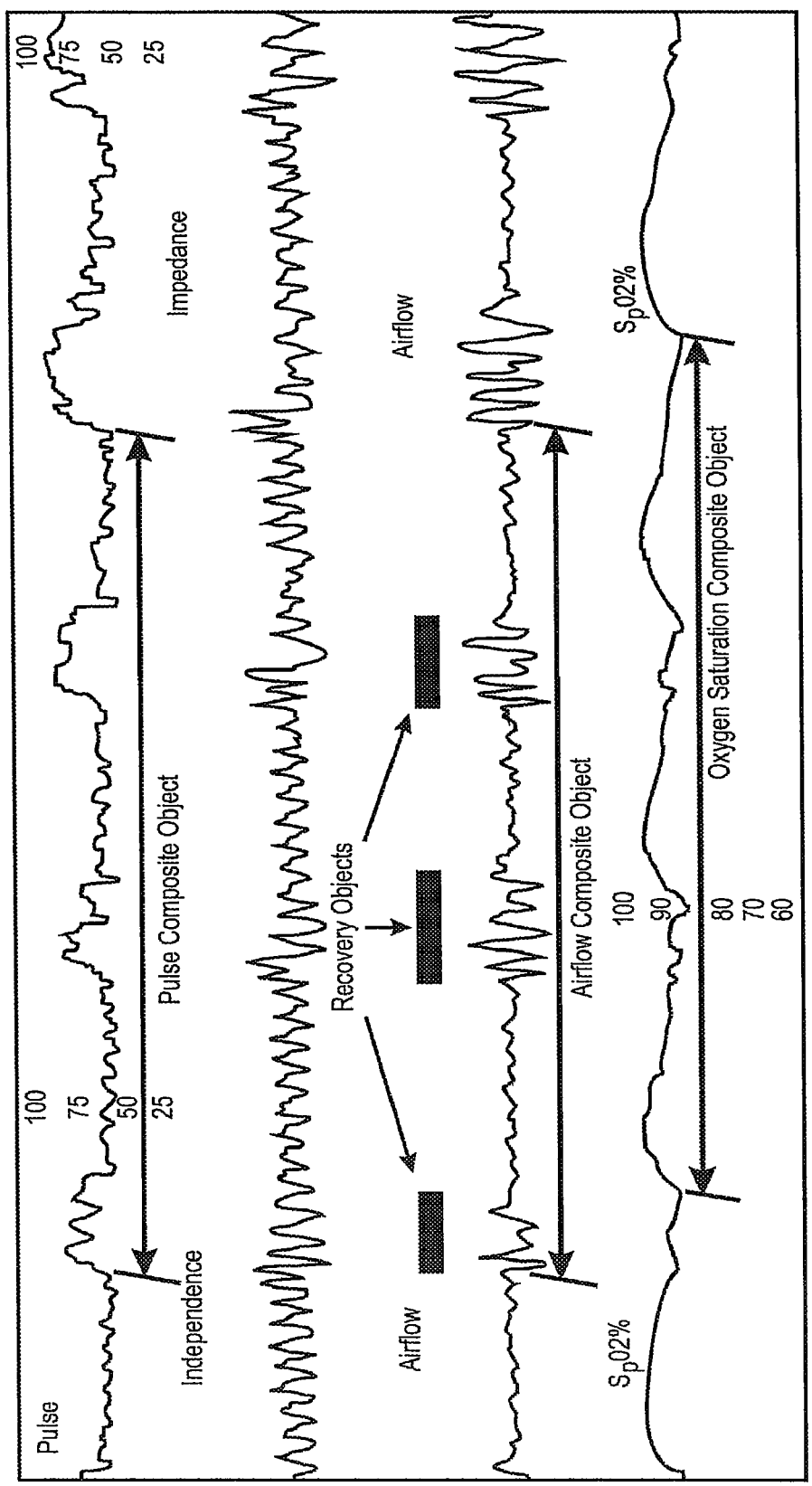
FIG. 5b shows an illustration of a raw data set of a plurality of signals derived from the mechanism of FIG. 5a and which may be represented as a multi-signal three-dimensional hierarchal object as shown in FIG. 5a in accordance with present embodiments.
Figure 5C:
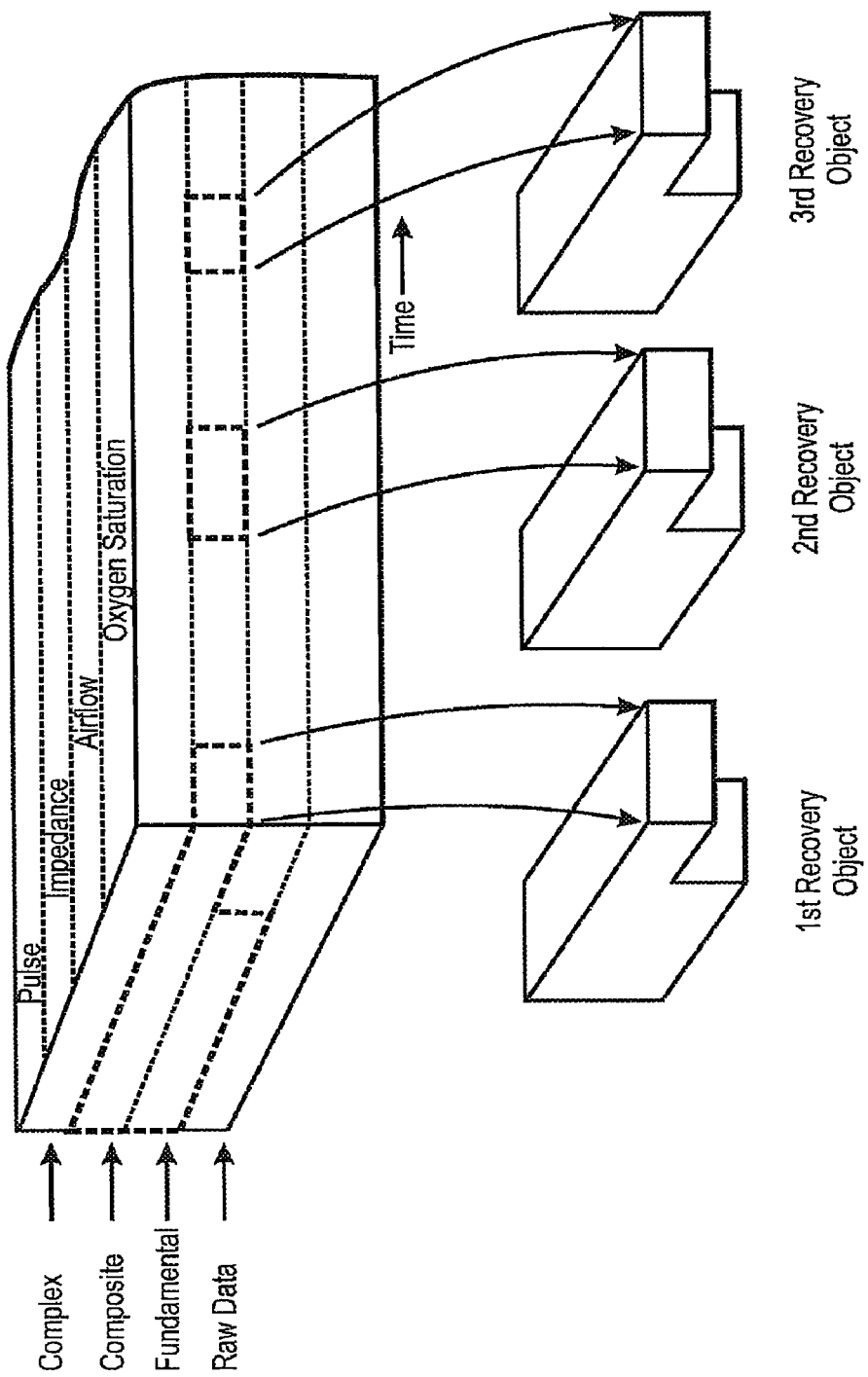
FIG. 5c shows a schematic representation of a portion of a multi-signal object as derived from the multiple corresponding time-series of FIG. 5b with three multi-signal recover objects up to the composite object level identified for additional processing in accordance with present embodiments.
Figure 6A:
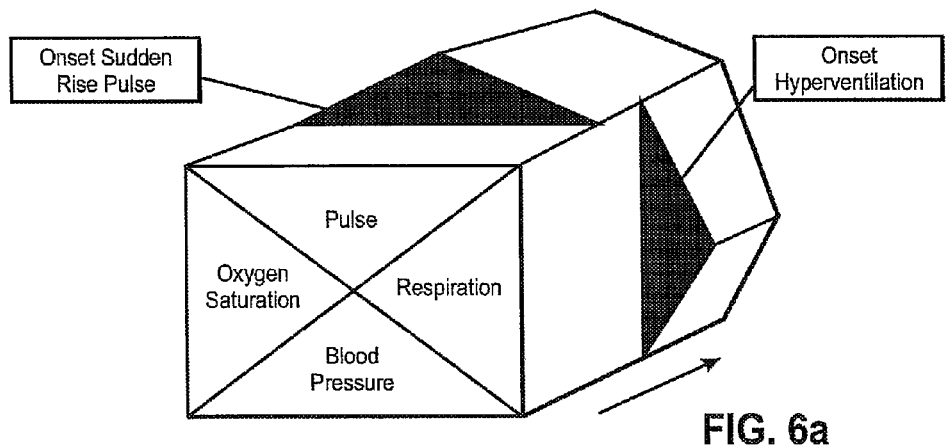
FIG. 6a shows a three-dimensional graphical output for clinical monitoring for enhanced representation of the dependent and dynamic relationships between patient variables, which the present inventors term the "monitoring cube" in accordance with present embodiments.
Figure 6B:
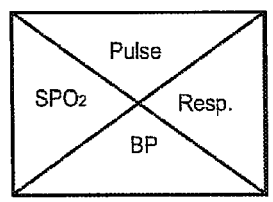
FIG. 6b shows a two-dimensional output of the "monitoring cube" during a normal physiologic state in accordance with present embodiments.
Figure 6C:
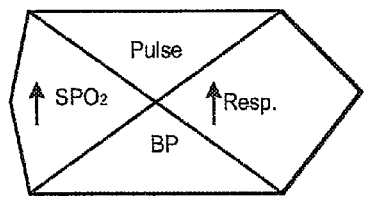
FIG. 6c shows a two-dimensional output of the "monitoring cube" showing physiologic convergence during an episode of volitional hyperventilation in accordance with present embodiments.
Figure 6D:
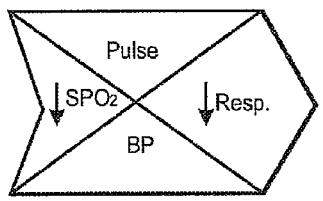
FIG. 6d shows a two-dimensional output of the "monitoring cube" showing pathophysiologic divergence as with pulmonary embolism in accordance with present embodiments.
Figure 6E:
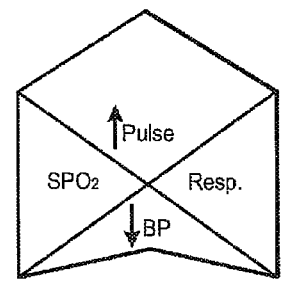
FIG. 6e shows a two-dimensional output of the "monitoring cube" showing a concomitant increase in blood pressure and heart rate, wherein the cube would be rotated to see which increase came first in accordance with present embodiments.

FIG. 5a shows an exemplary pathophysiologic process associated with a characteristic dynamic pattern of interaction. As discussed previously, this cyclic process is induced by upper airway instability. FIG. 5b shows four corresponding signals derived from monitoring different outputs of the patient during a time interval wherein the dynamic process of FIG. 5a is operative. The basic signals shown are Pulse, Chest Wall Impedance, Airflow, and Oxygen Saturation (SPO2). According to the present disclosure, these signals are processed into time-series fragments (as objects) and organized into the object levels as previously discussed. For the purpose of organizing and analyzing complex interactions between these corresponding and/or simultaneously derived signals, the same basic ascending process is applied to each signal. As shown in FIG. 5c these streaming objects, many of which overlap, project along a three-dimensional time-series comprised of multiple levels of a plurality of corresponding signals. A "multi-signal object" is comprised of at least one object from a first signal and at least one object from another signal. The multi-signal object of FIG. 5c has the primary and index characteristics derived from each component signal and from the spatial, temporal, and frequency relationships between the component signals. As illustrated, the objects defining a multi-signal object can include those from analogous or non-analogous levels. With this approach even complex and subtle dynamic patterns of interaction can be recognized.

This type of representation is too complex for presentation to hospital personnel but is preferred for the purpose of general representation of the data organization because, at this level of complexity, a complete representation of the time-series does not lend itself well to a two-dimensional graphical (and in some cases a three dimensional) representation. Along the time-series of sequential multi-signal objects, the spatial characteristics of these multi-signal objects change as a function of a plurality of interactive and different characteristics derived from the different signals.

The mathematical power of this approach to characterize the achieved organization of the complexity of the timed behavior of a physiologic system is illustrated by the application of this method to characterize the codependent behavior of ventilation and arterial oxygen saturation and plethesmographic pulse. While these variables are codependent in that a chance in one variable generally causes a change in the other two. They are also each affected differently by different pathologic insults and different preexisting pathologic changes. For example, the multi-signal objects comprising a time-series of ventilation and arterial oxygen saturation and plethesmographic pulse in a sedated 50-year-old obese smoker with asthma and sleep apnea are very different than those of a sleeping 50 year-old patient with Cheyene Stokes Respiration and severe left ventricular dysfunction. These differences are poorly organized or represented by any collection of two-dimensional graphical and/or mathematical representations. Despite this, throughout this disclosure, many of the signal interactions (such as those relating to pathophysiologic divergence) will be discussed as a function of a simplified two-dimensional component representation for clarity based on older standards of mathematical thought. However, it is one of the express purposes of the present disclosure to provide a much more mathematical robust system for the organization and analysis of the complex mathematical interactions of biologic systems through the construction of time-series sets of multidimensional and overlapping objects.

To illustrate the complexity ordered by this approach, consider the components of just one of the three simple recovery objects shown in FIGS. 5b and 5c. This single recovery object includes the following exemplary characteristics, each of which may have clinical relevance when considered in relation to the timing and characteristics of other objects;

1. Amplitude, slope, and shape of the oxygen saturation rise event at the composite level.
2. Amplitude, slope, and shape of the ventilation rise event at the composite level which contains the following characteristics at the fundamental level;
   Amplitude, slope, and shape of the inspiration rise object.
   Amplitude, slope, and shape of the expiration fall object.
   Frequency and slope dataset of the breath to breath interval of tidal breathing objects.
   Frequency and slope data sets of the amplitude, slope, and shape of the pulse rise and fall events.
3. Amplitude, slope, and shape of the pulse rise event at the composite level which contains the following exemplary characteristics at the fundamental level;
   Amplitude, slope, and shape of the plethesmographic pulse rise event.
   Amplitude, slope, and shape of the plethesmographic pulse fall event.
   Frequency and slope datasets of beat-to-beat interval of the pulse rate.
   Frequency and slope data set of the amplitude, slope, and shape of the pulse rise and fall events.

As is readily apparent, it is not possible for a health care worker to timely evaluate the values or relationships of even a modest traction of these parameters. For this reason, the output based on the analysis of these time-series of objects are presented in a succinct and interpretive format as will be discussed.

FIGS. 6a-6d shows one example of a method for animation of the summarized relationships between multiple interacting objects on the hospital monitor display. Such an animation can be shown as a small icon next to the real-time numeric values typically displayed on present monitors. Once the baseline is established for a patient either for example as the patient's baseline settings for a selected or steady state time period (of for example 10-15 minutes) or by a selected or calculated set of normal ranges, this is illustrated as a square. (The patient may initially have parameters out of the normal ranges and never exhibit a square output). After the square for this patient is established, the cube is built from the evolving time-series of these parameters. A given region of the cube can be enlarged or reduced as the particular value monitored increases or decreases respectively. The relationship between these variables can be readily seen even if they remain within the normal range. The computer can flag with a red indicator a cube that is showing pathophysiologic divergence when compared with the baseline values even though none of the values are at a typical alarm threshold. If other abnormalities (such as the development of pulse irregularity or a particular arrhythmia or ST segment change), this can be flagged on the cube so that the onset of these events can be considered in relation to other events. If preferred the time-series components of the cube and their relationships to occurrences on other monitored time-series can be provided in a two-dimensional timeline.

Using this approach the time-series relationships of multiple physiologic events can be characterized on the screen with a small dynamic animated icon in a succinct and easily understood way. There are many other alternative ways to animate a summary of the dynamic relationships and some of these will be discussed later in the disclosure.

One of the longstanding problems associated with the comparison of outputs of multiple sensors to derive simultaneous multiple time-series outputs for the detection of pathophysiologic change is that the accuracy and/or output of each sensor may be affected by different physiologic mechanisms in different ways. Because of this, the value of matching an absolute value of one measurement to an absolute value of another measurement is degraded. This is particularly true if the measurement technique or either of the values is imprecise. For example, when minute ventilation is measured by a precise method such as a pneumotachometer, then the relationship between the absolute values of the minute ventilation and the oxygen saturation are particularly relevant. However, if minute ventilation is being trended as by nasal thermister or nasal pressure monitoring or by chest wall impedance then the absolute values become much less usefulHowever, according to one aspect of the present disclosure, the application of the slope dipole method, the relationship between a plurality of simultaneously derived signals can be determined independent of the relationships of the absolute values of the signals. In this way, simultaneously derived signals can be identified as having convergence consistent with physiologic subordination or divergent shapes consistent with the development of a pathologic relationship or inaccurate data acquisition.

Figure 9:
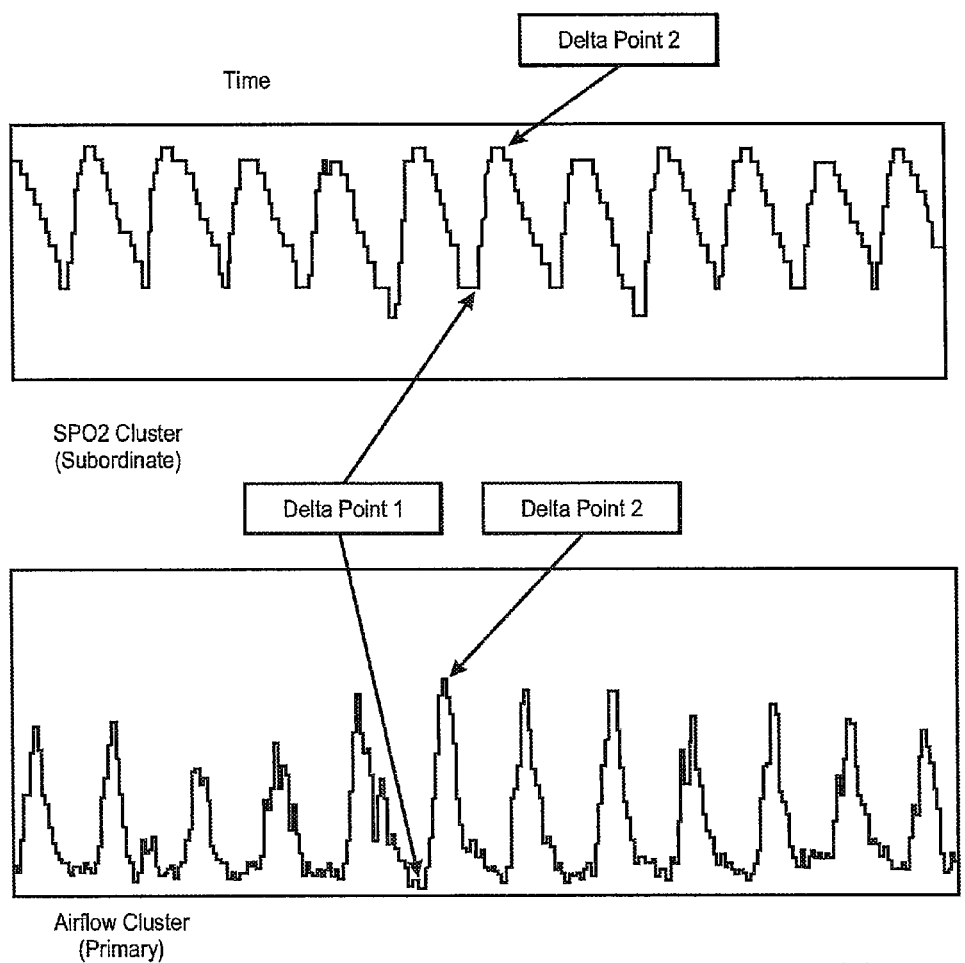
FIG. 9 shows corresponding data at the raw data level of airflow and oxygen saturation wherein the subordinate saturation signal segment demonstrates physiologic convergence with respect to the primary airflow signal segment in accordance with present embodiments.
Figure 10:
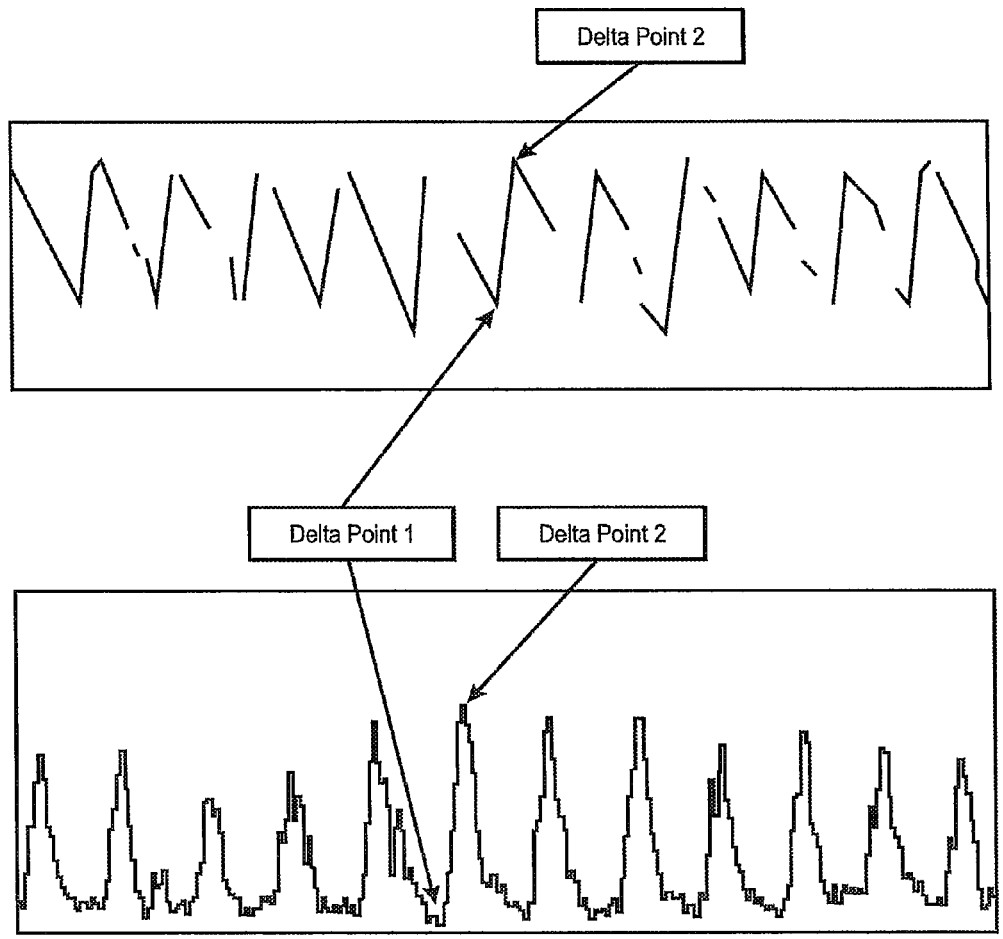
FIG. 10 shows the raw data level of FIG. 9 converted to the composite level where the data is now comprised of a time-series of sequential composite objects derived from the data sets of airflow and oxygen saturation signals in accordance with present embodiments.
Figure 11:
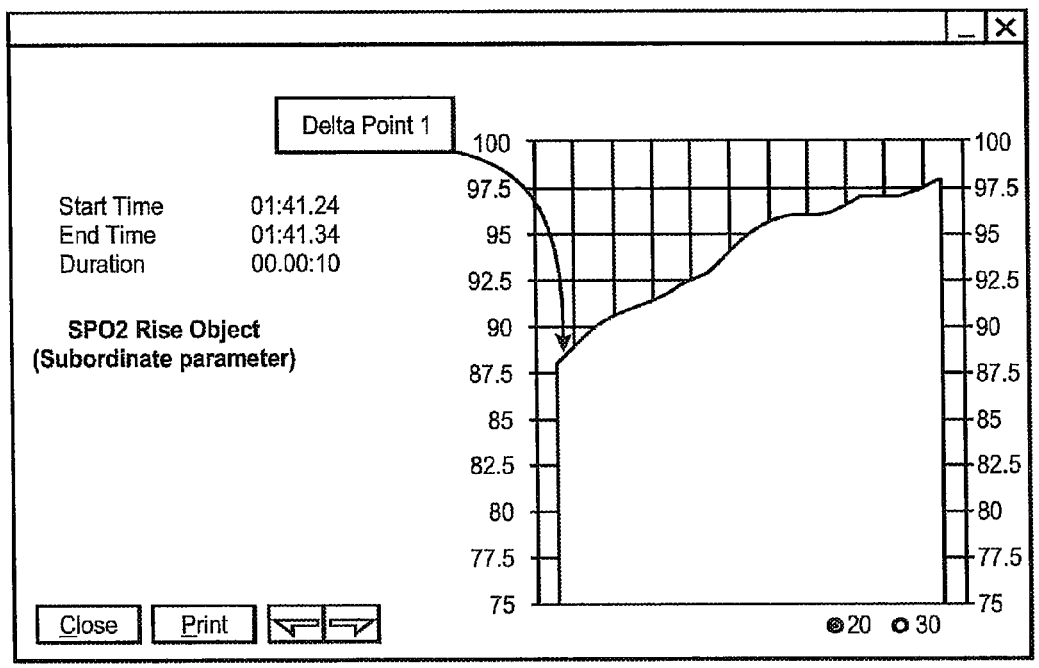
FIG. 11 shows a selected composite subordinate object of oxygen saturation from FIG. 10 matched with its corresponding primary composite object of airflow, as they are stored as a function of dipole datasets in the relational database, object database or object-relational database in accordance with present embodiments.
Figure 11:
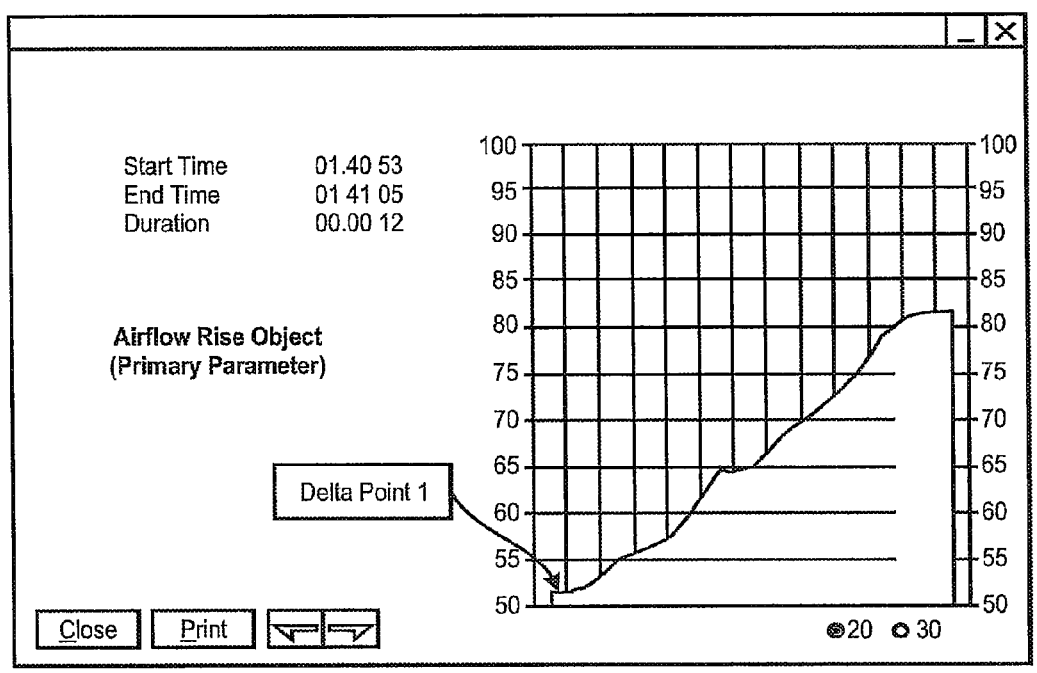

As noted, with physiologically linked signals a specific occurrence or magnitude of change in one signal in relationship to such a change in another signal may be more important and much more reproducible than the absolute value relationships of the respective signals. For this reason, the slope dipole method provides an important advantage to integrate such signals. Using this signal integration method, two simultaneously acquired physiologic linked signals are compared by the microprocessor over corresponding intervals by matching the respective slope dipoles between the signals. Although the exact delay between the signals may not be known, the processor can identify this by identifying the best match between the dipole sets. In the preferred embodiment, this "best match" is constrained by preset limits. For example, with respect to ventilation and oximetry, a preset limit could be provided in the range of 10-40 seconds although other limits could be used depending on the hardware, probe site and averaging, intervals chosen. After the best match is identified, the relationships between the signals are compared (for example, the processor can compare the slope dipole time-series of oxygen saturation to the slope dipole time-series of an index of the magnitude of ventilation). In this preferred embodiment, each slope dipole is compared. It is considered preferable that the dipoles of each respective parameter relate to a similar duration (for example. 1-4 seconds). With respect to airflow, calculation of the magnitude value of airflow may require sampling at a frequency of 25 hertz or higher, however, the sampling frequency of the secondary plot of the magnitude value of the index can, for example, be averaged in a range of one hertz to match the averaging interval of the data set of oxygen saturation. Once the signals have been sufficiently matched at the dipole level, they can be further matched at the composite level. According to the present disclosure, most object matching across different signals is performed at the fundamental level or higher, however timing matching can be performed at the dipole level and this can be combined with higher level matching to optimize a timing match. FIGS. 9, 10, and 11, show schematic mapping of matched clusters of airway instability (of the type shown in FIG. 5*b*) where clusters are recognized and their components matched at the composite object level. When the objects are matched, the baseline range relationship between the signals can be determined. This baseline range relationship can be a magnitude value relationship or a slope relationship. The signals can then be monitored for variance from this baseline range, which can indicate pathology or signal inaccuracy. The variance from baseline can be, for example, an increase in the relative value of ventilation in relation to the oximetry value or a greater rate of fall in oxygen saturation in relation to the duration and/or slope of fall of ventilation. In another example, the variance can include a change from the baseline delay between delta points along the signals.

With multiple processed signals as defined above, the user, which can be the program developer, can then follow the following to complete the process of searching for a specific pattern of relationships between the signals.

1. Specify a search wave pattern.
2. Analyze and divide the search pattern into objects.
3. Input the allowed deviation (if any) from the search pattern or the objects comprising it.
4. Input additional required relationships (if any) to other objects in the target waveform.
5. Apply the search pattern or selected component objects thereof to a target waveform.

Various methods of identification may be employed to provide a wave pattern to the system. Users may:

Choose from a menu of optional patterns.
Select dimensional ranges for sequential related patterns of ascending complexity.
Draw a wave pattern within the system with a pointing or pen device.
Provide a scanned waveform.
Provide a data feed from another system.
Describe the pattern in natural language.
Type in a set of points.
Highlight a sub-section of another waveform within the system.

The system can be automated such that such a search is automatically applied once the criteria are established. Also the method of identification of the search pattern can be preset. For example the occurrence of a specific sequence of objects can be used as a trigger to select a region (which can be one of those objects) as the specified search pattern, the processor can automatically search for other such patterns in the rest of the study. The result of any of these inputs would be a set of points with or without a reference coordinate system definition as shown in FIGS. 3*a*-3*g*.

The system now begins its analysis of the target set of points to derive a series of object sets. These sets will be used to identify key properties of the wave pattern. These objects (and their boundaries) will provide a set of attributes which are most likely to be significant in the wave pattern and that can be acted upon in the following ways:

To provide parameters on which sets of rules may be applied for the identification of expected conditions.
To provide parameters that can be associated with specifically allowable deviations and/or a globally applied deviations.
To provide parameters than can be used to score the relative similarity of patterns within the target waveform.

Using this method, a search can be carried out for specific pathophysiologic anomalies. This can be carried out routinely by the software or on demand.

One example of the clinical utility of the application of the object processing and recognition system to physiologic signals is provided by identification of upper airway instability. As discussed in the aforementioned patents and application, events associated with airway instability are precipitous. In particular, the airway closure is precipitous and results in a rapid fall in ventilation and oxygen saturation. Also the subsequent airway opening airway is precipitous, and because ventilation drive has risen during closure, the resulting ventilation flow rate (as represented by a measurement of airflow deflection amplitude) rises rapidly associated with recovery. Also, after the period of high flow rate associated with the recovery the flow rate precipitously declines when the chemoreceptors of the brain sense ventilation overshoot. In this way, along a single tracing of timed airflow deflection amplitude, three predictable precipitous relatively linear and unidirectional waveform deflections changes have occurred in a particular sequence in a manner analogous to the tracing of the SPO2 or pulse rate. Subsequent to this, the unstable airway attain closes suddenly propagating the cluster of cycles in all of these waveforms.

As noted above, a hallmark of airway instability is a particular cluster timed sequence of precipitous, unidirectional changes in the timed data set. For this reason, the first composite object to be recognized is defined by a precipitous unidirectional change in timed output of one of the above parameters. The system then recognizes along the fundamental sequential unipolar composite objects and builds the composite level comprised of time-series of these composite objects. One embodiment uses the following method to accomplish this task. A unipolar "decline object" is a set of consecutive points over which the parameter level of the patient is substantially continually falling. A unipolar "rise object" is a set of consecutive points over which the parameter is substantially continually increasing. A "negative pattern" is a decline together with a rise object wherein the rise follows the decline within a predetermined interval. A "positive pattern" is a rise together with a decline wherein the decline follows the rise within a predetermined interval. How closely these composite objects can follow each other is a specifiable parameter. At the complex object level, a cluster is a set of consecutive positive or negative patterns that appear close together. How closely these patterns must follow each other to qualify, as a cluster is a specifiable parameter. (Typical ranges for these parameters have been discussed in the aforementioned patents).

When applied, the digital pattern program proceeds in several phases. In the first phase, decline and rise objects are identified. In the second phase, negative and positive patterns are identified. In the third phase, clusters of negative and/or positive patterns are identified in the fourth phase of the relationship between the events and patterns is calculated and outputted. In the fifth phase a diagnosis and severity indexing of airway or ventilation instability or sleep/sedation apnea is made, in the sixth phase a textual alarm or signal is outputted and/or treatment is automatically modified to eliminate cluster, then the process is then repeated with each addition to the dataset in real-time or with stored timed datasets.

One system in accordance with present embodiments applies either a linear or iterative dipole slope approach to the recognition of waveform events. Since the events associated with airway collapse and recovery are generally precipitous and unipolar, the linear method suffices for the recognition and characterization of these nonlinear waves. However, the iterative dipole slope approach is particularly versatile and useful in situations wherein the user would like an option to select the automatic identification of a specific range of nonlinear or more complex waves. Using the iterative dipole slope method, the user can select specific consecutive sets of points from reference cases along a waveform as by sliding the pointer over a specific waveform region. Alternatively, the user can draw the desired target waveform on a scaled grid. The user can also input or draw range limits thereby specifying an object or set of objects for the microprocessor to recognize along the remainder of the waveform or along other waveforms. Alternatively, the processor can automatically select a set of objects based on pre-selected criteria (as will be discussed). Since the iterative dipole process output is shape (including frequency and amplitude) dependent but is not necessarily point dependent, it is highly suited to function as a versatile and discretionary engine for performing waveform pattern searches. According to the present invention, the waveform can be searched by selecting and applying objects to function as Boolean Operators to search a waveform. The user can specify whether these objects are required in the same order. Recognized object sequences along the waveform can be scored to show the degree of match with the selected range. If desired (as for research analysis of waveform behavior) anomalies within objects or occurring in one or more of a plurality of simultaneously processed tracings can be identified and stored for analysis.

For the purpose of mathematically defining the presently preferred object system, according to the present disclosure, for recognition of digital object patterns let $o_1, o_2, \ldots, o_m$ be the original data points. The data can be converted to a smoother data set, $x_1, x_2, \ldots, x_n$, by using a moving n average of the data points as a 1-4 second average for cluster recognition or as a 15-30 second average for the identification of a pathophysiologic divergence. For the sake of clarity of presentation, assume that $x_i$ is the average of the original data points for the $i^{th}$ second. A dipole is defined to be a pair of consecutive data points. Let $d_i=(x_i,x_i+1)$ be the $i^{th}$ dipole, for $i=1, 2, \ldots, n-1$. The polarity, say $p_i$ of the $i^{th}$ dipole is the sign of $x_i+1-xi$, (i.e. $p_i=1$ if $x_{i+1}>x_i$, $p_i=0$ if $x_{i+1}=x_i$, and $p_i=-1$ if $x_{i+1}<x_i$). For the purpose of automatic recognition of user specified, more complex nonlinear waveforms, the data can be converted to a set of dipole slopes, $z_1, z_2, \ldots, z_n$. Let $z_i=(x_{i+1}-x_i)$ be the $i^{th}$ dipole slope, for $i=1, 2, \ldots, n-1$.

To recognize a decline event by applying the iterative slope dipole method according to the present disclosure, let $\{z_1, z_2, \ldots, z_n\}$ be a set of consecutive dipole slopes. Then $\{z_1, z_2, \ldots, z_n\}$ is a decline if it satisfies the following conditions:

1. $z_1, z_2, \ldots, z_n$ are less than zero, i.e., the parameter level of the patient is continually falling over the set of dipole slopes. (This condition will be partially relaxed to adjust for outliers, as by the method described below for the linear method.)
2. The relationship of $Z_i$ to $z_2$, $z_2$ to $z_3$, $\ldots z_{n-1}$ to $z_n$ is/are specified parameter(s) defining the shape of the decline object, these specified parameters can be derived from the processor based calculations of the dipole slopes made from a user selected consecutive data set or from a set drawn by the user onto a scaled grid.

To recognize a rise event a similar method is applied wherein $z_1, z_2, \ldots, z_n$ are greater than zero. Complex events, which include rise and fall components are built from these more composite objects. Alternatively, a specific magnitude of change along a dipole slope dataset can be used to specify a complex object comprised of two composite objects separating at the point of change (a waveform deflection point). In one application the user slides the cursor over the portion of the wave, which is to be selected, and this region is highlighted and enlarged and analyzed with respect to the presence of more composite objects. The dimensions of the object and the slope data set, which defines it, can be displayed next to the enlarged waveform. If the object is complex (as having a plurality of segments of differing slope polarity or having regions wherein the slope rapidly changes as by a selectable threshold), then each composite object is displayed separately with the respective dimensions and slope data sets. In this way the operator can confirm that this is the actual configuration desired and the user is provided with a summary of the spatial and dimensional characteristics of the composite objects, which define the actual selected region. The operator can select a range of variations of the slope data set or chance the way in which the composite objects are defined, as by modifying the threshold for a sustained change in slope value along the slope dataset. For example, by allotting at least one portion of the slopes to vary by a specified amount, such as 10%, by inputting graphically the variations allowed. If the operator "OKs" this selection, the processor searches the entire timed dataset for the composite objects, building the selected object from the composite objects if identified.

To recognize a decline event by applying the linear method according to the present invention disclosure, let $\{x_i, x_{i+1}, \ldots, x_r\}$ be a set of consecutive points and let $s=(x_r-x_i)/(r-i)$ be the overall slope of these points. (The slope could be defined by using linear regression, but one definition in accordance with present embodiments allows for improved fidelity of the output by allotting rejection based on outlier identification, which will be discussed). Then $\{x_i, x_{i+1}, \ldots, x_r\}$ is a decline if it satisfies the following conditions:

3. $x_i > x_{i+1} 2 > \ldots x_r$, i.e. the parameter level of the patient is continually falling over the set of points. (This condition will be partially relaxed to adjust for outliers, as described below.)
4. $r-i \geq D_{min}$, where $D_{min}$ is a specified parameter that controls the minimum duration of a decline.
5. $s_{min} \leq s \leq s_{max}$, where $s_{min}$ and $s_{max}$ are parameters that specify the minimum and maximum slope of a decline, respectively.

The set $\{97, 95, 94, 96, 92, 91, 90, 88\}$, does not satisfy the current definition of a decline even though the overall level of the parameter is clearly falling during this interval. The fourth data point, 96, is an outlier to the overall pattern. In order to recognize this interval as a decline, the first condition must be relaxed to ignore outliers. The modified condition 1 is:

1*. Condition 1 with Outlier Detection
 a. $x_i > x_{i+1}$,
 b. $x_j > x_{j+1}$ or $x_{j+1} > x_{j+2}$ for $j=i+1, \ldots, r-2$.
 c. $x_{r-1} > x_r$.

To recognize a rise event, let $\{x_i, x_{i+1}, \ldots, x_r\}$ be a set of consecutive points and let $s=(x_r-x_i)/(r-i)$ be the overall slope of these points. Then $\{x_i, x_{i+1}, \ldots, x_r\}$ is a rise if it satisfies the following conditions:

1. $x_i < x_{i+1} < \ldots < x_r$, i.e., the parameter level of the patient is continually rising over the set of points. (This condition will be partially relaxed to adjust for outliers, as described below.)
2. $r-i \geq D_{min}$, where $D_{min}$ is a specified parameter that controls the minimum duration of rise.
3. $s_{min} \leq s \leq s_{max}$, where $s_{min}$ and $s_{max}$ are parameters that specify the minimum and maximum slope of a decline, respectively.

Similar to declines, the first condition of the definition of a rise is relaxed in order to ignore outliers. The modified condition 1 is:

1*. Condition 1 with Outlier Detection
 a. $x_i < x_{i+1}$.
 b. $x_j < x_{j+1}$ or $x_{j+1} < x_{j+2}$ for $j=i+1, \ldots, r-2$.
 c. $x_{r-1} < x_r$.

To recognize a negative pattern, the program iterates through the data and recognizes events and then identifies event relationships to define the patterns. The system uses polarities (as defined by the direction of parameter movement in a positive or negative direction) to test for condition (1*) rather than testing for greater than or less than. This simplifies the computer code by permitting the recognition of all decline and rise events to be combined in a single routine and ensures that decline events and rise events do not overlap, except that they may share an endpoint. The tables below show how condition (1*) can be implemented using polarities.

| Equivalent Condition 1* for Decline event | | |
|---|---|---|
| | Condition 1* | Equivalent Condition |
| a. | $x_i > x_{i-1}$ | $p_i = -1$ |
| b. | $x_j > x_{j-1}$ or $x_{j-1} > x_{j-2}$ | $p_j = -1$ or $p_{j+1} = -1$ |
| c. | $x_{r-1} > x_r$ | $p_{r-1} = -1$ |

| Equivalent Condition 1* for Rise event | | |
|---|---|---|
| | Condition 1* | Equivalent Condition |
| a. | $x_i < x_{i-1}$ | $p_i = 1$ |
| b. | $x_j < x_{j-1}$ or $x_{j-1} < x_{j-2}$ | $p_j = 1$ or $p_{j+1} = 1$ |
| c. | $x_{r-1} < x_r$ | $p_{r-1} = 1$ |

The pseudocode for the combined microprocessor method, which recognizes both unipolar decline events and unipolar rise events, is shown below. In this code, E is the set of events found by the method, where each event is either a decline or a rise.

```
Event Recognition
i = 1
event_polarity = p₁
for j = 2 to n-2
    if (p_j ≠ event_polarity) and (p_{j-1} ≠ event_polarity)
        r = j
        X = { x_p...x_r }
        if event_polarity = 1
            Add X to E if it satisfies rise conditions (2) and (3)
        elseif event_polarity = -1
            Add X to E if it satisfies decline conditions (2) and (3)
        endif
        i = j
        event_polarity = p_j
    endif
endfor
Add X={x_i, ..., x_n} to E if it satisfies either the rise or decline conditions.
```

Next, A specific pattern is recognized by identifying a certain sequence of consecutive events, as defined above, which comply with specific spatial relationships. For example, a negative pattern is recognized when a decline event, say $D=\{x_i, \ldots, x_j\}$, together with a rise event, say $R=\{x_k, \ldots, x_m\}$, that closely follows it. In particular, D and R must satisfy $k-i \leq t_{dr}$, where $t_{dr}$ is a parameter, specified by the user, that controls the maximum amount of time between D and R to qualify as a negative pattern.

The exemplary pseudocode for the microprocessor system to recognize a negative pattern is shown below. Let $E=\{E_1, E_2, \ldots, E_q\}$ be the set of events (decline events and rise events) found by the event recognition method, and let DR be the set of a negative pattern.

```
Negative Pattern Recognition
for h = 1 to q-1
    Let D = {x_i,...,x_j,} be the event E_h
    if D is a decline event
        Let R = {x_k,...,x_m} be the event E_{h+1}
        if R is a rise event
            gap = k - j
            if gap ≤ t_dr
                Add (D,R) to the list. DR of negative patterns
            endif
        endif
    endif
endfor
```

As noted, a cluster is a set of consecutive negative or positive patterns that appear close together. In particular, let $C=\{DR_i, DR_{i+1}, \ldots, DR_k\}$ be a set of consecutive negative patterns, $s_j$ be the time at which $DR_j$ starts, and $e_j$ be the time at which $DR_j$ ends. Then C is a cluster if it satisfies the following conditions:

1. $s_{j+1} - e_j \leq t_c$, for $j=i, \ldots, k-1$, where $t_c$ is a parameter, specified by the user, that controls the maximum amount of time between consecutive negative patterns in a cluster.
2. $k-i-1 \geq c_{min}$, where $e_{min}$ is a parameter, specified by the user, that controls the minimum number of negative patterns in a cluster.

The pseudocode for the algorithm to recognize clusters of negative patterns is shown below. Let $DR=\{DR_1, DR_2, \ldots, DR_r\}$ be the set of negative patterns found by the above pattern recognition method.

```
        Cluster Recognition (of negative patterns)
f = 1;
    for h = 2:r
        Let R = | x_l,.....x_m | be the rise in DR_{h-1}
        Let D = | x_i,.....x_j | be the decline in DR_h
        gap = i - m
        if gap > t_c
            g = h - 1
            if g - f + 1 ≥ c_min
                Add DR_1. DR_{i+1}...., DR_g to the list of clusters
            endif
            f = h
        endif
    endfor
    g = r
    if g - f - 1 ≥ c_min
        Add DR_{i - DRi-1}..... DR_g to the list of clusters
    endif
```

According to the present invention, this object-based linear method maps the unique events, patterns and clusters associated with airway instability because the sequential waveform events associated with airway closure and reopening are each both rapid, substantially unipolar and relatively linear. Also, the patterns and clusters derived are spatially predictable since these precipitous physiologic changes are predictably subject to rapid reversal by the physiologic control system, which is attempting to maintain tight control of the baseline range. Because timed data sets with predictable sequences of precipitous unidirectional deflections occur across a wide range of parameters, the same digital pattern recognition methods can be applied across a wide range of clustering outputs, which are derived from airway instability. Indeed the basic underlying mechanism producing each respective cluster is substantially the same (e.g. clusters of positive pulse rate deflections or positive airflow amplitude deflections). For this reason, this same system and method can be applied to a timed data set of the oxygen saturation, pulse rate (as for example determined by a beat to beat calculation), amplitude of the deflection of the chest wall impedance waveform per breath, amplitude of deflection of the airflow signal per breath (or other correlated of minute ventilation), systolic time intervals, blood pressure, deflection amplitude of the nasal pressure, the maximum exhaled $CO_2$ per breath, and other signals. Additional details of the application of this digital pattern recognition method to identify clusters are provided in patent application Ser. No. 09/409,264 to the present inventor.

Next, for the purpose of building the multi-signal object, a plurality of physiologically linked signals are analyzed for the purpose of recognizing corresponding patterns and corresponding physiologic convergence for the optimal identification of the cluster cycles. For example, a primary signal such as airflow is analyzed along with a contemporaneously measured secondary signal such as oxygen saturation as by the method and system discussed previously. As discussed previously, for the purpose of organizing the data set and simplifying the analysis, the raw airflow signal is processed to a composite object level. For example, the composite level of airflow can be a data set of the amplitude and/or frequency of the tidal airflow as by thermister or pressure sensor, or another plot, which is indicative of the general magnitude of the timed tidal airflow. In the presently preferred embodiment, a mathematical index (such as the product) of the frequency and amplitude is preferred, because such an index takes into account the important attenuation of both amplitude and frequency during obstructive breathing. Furthermore, both the frequency and amplitude are often markedly increased during the recovery interval between apneas and hypopneas. It is not necessary that such a plot reflect exactly the true value of the minute ventilation but rather, it is important that the plot reflect the degree of change of a given level of minute ventilation. Since these two signals are physiologically linked, an abrupt change in the primary signal (airflow) generally will produce readily identifiable change in the subordinate signal (oxygen saturation). As previously noted, since the events which are associated with airway collapse are precipitous, the onset of these precipitous events represent a brief period of rapid change which allows for optimal detection of the linkage between the primary signal and the subordinate signal.

The signals can be time matched by dipole slopes at the fundamental level. In addition, in one embodiment, the point of onset of precipitous change is identified at the composite object level of the primary signal and this is linked to a corresponding point of a precipitous change in the composite object level of the subordinate signal. This is referred to herein as a delta point. As shown in FIGS. 9, 10, and 11, a first delta point is identified in the primary signal and in this example is defined by the onset of a rise object. A corresponding first delta point is identified in the subordinate signal and this corresponds to the onset of a rise object in the subordinate signal. A second delta point is identified which is defined by the point of onset of a fall object in the primary signal and which corresponds to a second delta point in the subordinate signal defined by the onset of a fall event in the secondary signal. The point preceding the second delta point (the "hyperventilation reference point") is considered a reference indicating an output associated with a degree of ventilation, which substantially exceeds normal ventilation and normally is at least twice normal ventilation. When applying airflow as the primary signal and oximetry as the subordinate signal, the first delta point match is the most precise point match along the two integrated waveforms and therefore comprises a ("timing reference point") for optimally adjusting for any delay between the corresponding objects of the two or more signals. The mathematical aggregate (such as the mean) of an index of the duration and slope, and/or frequencies of composite rise and fall objects of the fundamental level of tidal ventilation along a short region adjacent these reference points can be applied as a general reference for comparison to define the presence of relative levels of ventilation within objects along other portions of the airflow time-series. Important fundamental object characteristics at these reference points are the slope and duration of the rise object or fall object because these are related to volume of air, which was moved during the tidal breath. The fundamental objects comprising the tidal breaths at the reference hyperventilation point along the composite level are expected to have a high slope (absolute value) and a high frequency. In this way, both high and low reference ranges are determined for the signal. In another embodiment, these points can be used to identify the spatial shape configuration of the rise and fall objects at the fundamental level during the rise and fall objects at the composite level.

As shown in FIGS. 9 and 10, using this method at the composite object level, a first object (FIG. 11) can then be identified in the primary signal between the first delta point and the second delta point which is designated a recovery object. As also shown in FIG. 11 the matched recovery object is also identified in the subordinate signal as the point of onset of the rise object to the point of the onset of the next subsequent fall object. In the preferred embodiment, the recovery object is preceded by the apnea/hypopnea object which is defined by the point of onset of the fall object to the point of onset of the next rise object in both the primary and subordinate signals.

Figure 12:
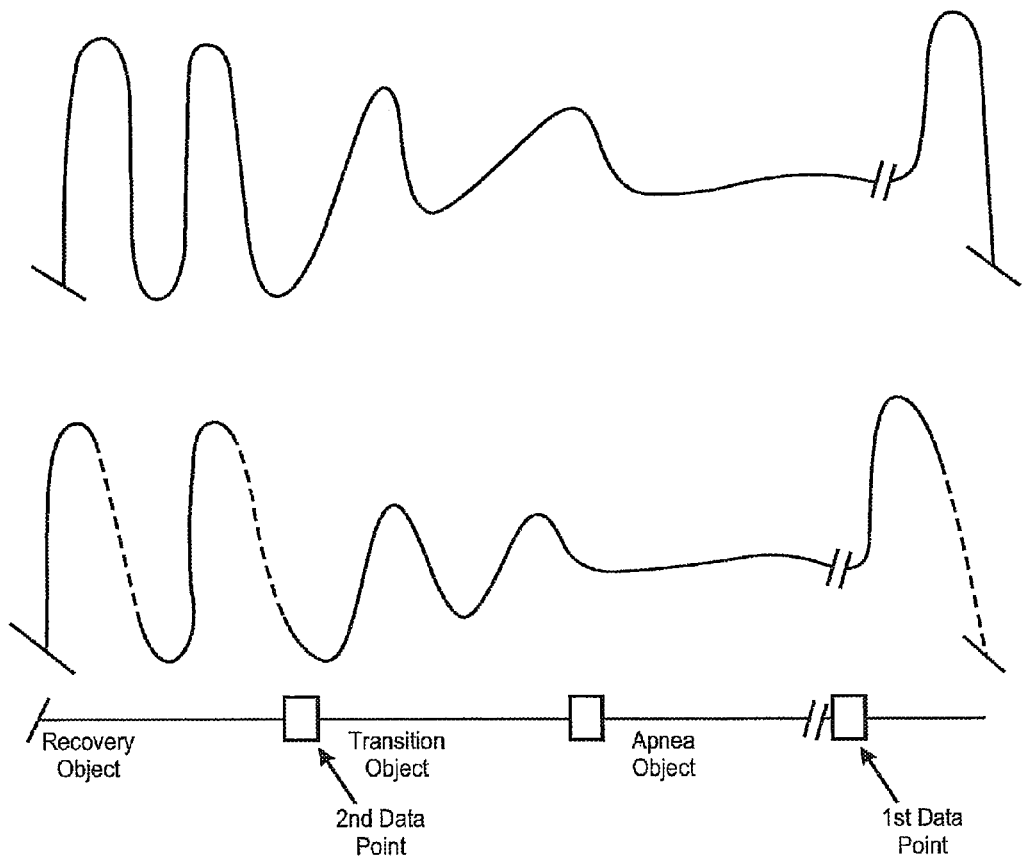
FIG. 12 shows a comparison between two data sets of airflow wherein at the fundamental level the second data set shows evidence of expiratory airflow delay during the recovery object, wherein the recovery object is recognized at the composite level in accordance with present embodiments.

As shown in FIG. 12, a recovery object recognized at the composite level can be used to specify a region for comparison of sequential objects at the fundamental object level. Here, upon recognition of the presence of a recovery object (where it is anticipated that the ventilation effort will be high) the ratio of the slope of exhalation objects to the slope of inhalation objects can be compared within the recovery object and the time-series derived from these comparisons can be plotted if desired. During upper airway obstruction, the inspiration is slowed to a greater degree than exhalation. The magnitude change of the ratio during the clusters of apneas provides an index of the magnitude of upper airway narrowing (which selectively slows inhalation during the clustered apnea/hypopnea objects). However, during the recovery object or at the "hyperentilation reference point", the upper airway should be wide open for both inhalation and exhalation and this can be used as a reference because, during this time, the absolute slope of the fundamental objects during recovery can then be compared to the absolute slope of the fundamental objects during other times along the night to provide an indication of upper or looser airway narrowing.

When airflow is the primary signal and oximetry the subordinate, the most reliable delta point is the point of onset of a rapid rise in ventilation (in a patient with an oxygen saturation, at the point of onset point, of less than 96-97%). Patients with very unstable airways will generally have relatively short recovery objects. Other patients with more stable airways may have a multi-phasic slope of decline in airflow during the recovery objects herein, for example, there is an initial precipitous decline event in the airflow parameter and then a plateau or a much more slight decline which can be followed by a second precipitous decline to virtual absence of ventilation. Using the slope dipole method these composite objects can be readily separated such that the occurrence of multiple composite objects (especially wherein the slopes are close to zero) or a single object Faith a prolonged slowly falling slope dataset occurring immediately after the first data point, can be identified. These patients generally have longer recovery intervals and more stable airways. The identification of a decline object associated with decline from the hyperventilation phase of recovery followed by a plateau and/or a second decline object associated with the onset of apnea is useful to indicate the presence of a greater degree of airway stability. Accordingly, with the airflow signal, a third delta point (FIG. 12) designated a "airflow deflection point" can often be identified in the airflow tracing corresponding to the deflection point at the nadir of drop in airflow at the end of the recovery. This point is often less definable than the second delta point and for this reason matching the second delta points in the airflow and oximetry signals is preferred although with some tracings a match between the airflow deflection point and the second delta point in the oximetry dataset provides a better match.

If a significant decline in airflow is identified after the "airflow deflection point", then the region of the intervening decline object and the next delta point (onset of the next recovery) is designated a reference "ventilation nadir region". If the region or object(s) from the second delta point to ventilation deflection point is very short (as 0-3 breaths) and the ventilation nadir region has a mean slope close to or equal to zero (i.e. the region is relatively flat) and the deflection amplitude is close to zero or otherwise very small indicating now or very little ventilation, then the airway is designated as highly unstable.

Another example of object processing at the fundamental object level, in accordance with present embodiments, includes the processor-based identification of fluttering of the plateau on the pressure signal to recognize partial upper airway obstruction. During the nasal pressure monitoring a fluttering plateau associated with obstructive breathing often occurs intervening a rise event and a fall event of tidal breathing. Since the plateau objects are easily recognizable at the fundamental level and readily separated using the present object recognition system the plateau can be processed for the tiny rise and fall objects associated with fluttering and the frequency of these objects can be determined. Alternatively, a Fourier transform can be applied to the plateau objects between the rise and fall events of the nasal pressure signal to recognize the presence of fluttering or another method can be utilized which provides an index of the degree of fluttering of the plateau objects.

Since reduced effort also lowers the slope of exhalation and inspiration, the configuration (as defined by the slope dataset of the dipoles defining the fundamental objects of both inspiration and expiration at the reference objects) can be applied as reference fundamental object configurations defining the presence of hyperventilation or hypopnea. This process is similar to the selection process for identifying search objects described earlier but in this case the input region is preselected. In an example, the range of characteristics of the objects at the fundamental level derived from one or more tidal breaths occurring prior to the second airflow delta point can be used to designate a reference hyperventilation objects range. Alternatively, the object based characteristics defined by the range of characteristics of the objects derived from one or more tidal breaths occurring prior to the first airflow delta point can be used to designate a reference hypopnea object's range. The processor can then automatically assess object ranges along other points of the tracing. In this way the processor can apply an artificial intelligence process to the identification of hypopneas by the following process:

1. Identify the region wherein a hypopnea is expected (as for example two to three tidal breaths prior to the first airflow delta point).
2. Select this as a region for objects processing to define the characteristics of hypopneas in this patient.
3. Process the region using the slope dipole method to define the range of fundamental objects comprising the target region.
4. Compare the identified range of objects to other analogous objects along to tracing to identify new objects having similar characteristics.
5. Using the criteria derived from the objects defining the target region search the processed waveform for other regions having matching sequences of new objects and identify those regions.
6. Provide an output based on said identification and/or take action (e.g. increase CPAP) based on said identification.

These processing methods exploit the recognition that certain regions along a multi-signal object (as within a cluster) have a very high probability of association with certain levels of ventilation. The objects defining those regions can then be used as a reference or as an opportunity to examine for the effects of a given level of ventilation effort on the flow characteristics. Patients with obstructive sleep apnea will have a fall in the slopes of fundamental inspiration objects during decline objects at the composite level indicative of upper airway occlusion. Also, as shown in FIG. 12, patients with asthma or chronic obstructive lung disease will have a reduced slope of the exhalation when compared to the slope of inhalation during the rise objects between apneas at the base level. According to one embodiment of the present disclosure, the time-series of the ratio of the slope of inhalation objects to exhalation objects is included with the basic time-series. Patients with simple, uncomplicated obstructive apnea will have clusters of increasing slope ratios with the ratio rising to about one during the recovery objects. Patients with combined obstructive apnea and asthma or chronic obstructive lung disease will have a greater rise in slope ratios during the recovery objects to into the range of 2-3 or greater, indicating the development of obstructive lower airways during the rapid breathing associated with recovery.

Figure 8:
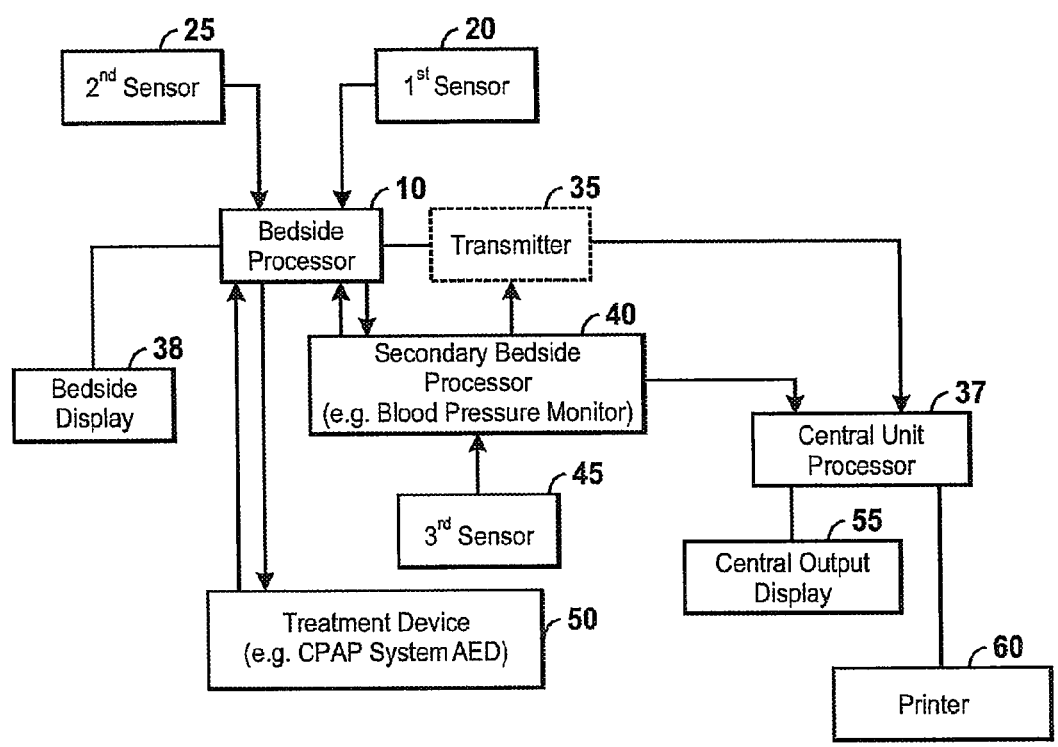
FIG. 8 shows a schematic of a monitor and automatic patient treatment system in accordance with present embodiments.

One system for processing, analyzing and acting on a time-series of multi-signal objects in accordance with present embodiments is shown in FIG. 8. The examples provided herein show the application of this system for real time detection, monitoring, and treatment of upper airway and ventilation instability and for the timely identification of pathophysiologic divergence. The system includes a portable bedside processor 10 having at least a first sensor 20 and a second sensor 25, which may provide input for at least two of the signals discussed supra. The system includes a transmitter 35 to a central processing unit 37. The bedside processor 10 includes an output screen 38, which provides the nurse with a bedside indication of the sensor output. The bedside processors can be connected to a controller of a treatment or stimulation device 50 (which can include a positive pressure delivery device, an automatic defibrillator, a vibrator or other tactile stimulator, or a drug delivery system such as a syringe pump or back to the processor to adjust the analysis of the time-series inputs), the central unit 37 preferably includes as output screen 55 and printer 60 for generating a hard copy for physician interpretation. According to present embodiments, as will be discussed in detail, the system thereby allows recognition of airway instability, complications related to such instability, and pathophysiologic divergence in real time from a single or multiple inputs. The bedside processor is connected to a secondary processor 40 which can be a unit, which performs measurements intermittently and/or on demand such as a non-invasive blood pressure monitor or an ex-vivo monitor, which draws blood into contact with a sensor on demand for testing to derive data points for addition to the multi-signal objects. The secondary monitor 40 includes at least one sensor 45. The output of the bedside processor can either be transmitted to the central processor 37 or to the bedside monitor 10 to render a new object output, action, or analysis.

The method of hypopnea recognition discussed previously can be coupled with a conventional CPAP auto titration system which can comprise one treatment device of FIG. 8 to improve CPAP titration. The previously described method for detecting hypopneas is particularly useful to identify milder events because, while the configuration of each tidal breath of within the hypopnea may be only mildly different, there is a cumulative decline in ventilation or increase in airway resistance which often, eventually directly triggers a recovery object or triggers an arousal which then triggers the occurrence of a recovery object. The recovery objects being a precipitous response to a mild but cumulative decline on airflow is easier to recognize and is exploited to specify timing of the target processing as noted above.

One of the problems with conventional CPAP is that many of them (if not all) operate with pre-selected criteria for recognition of a hypopnea (such as 50% attenuation of a breath or group of breaths when compared with a certain number of preceding breaths). These systems generally determine the correct pressures for a given patient by measuring parameters derived from the algorithms which monitor parameters through the nasal passage. Unfortunately, the nasal passage resistance is highly variable from patient to patient and may be variable in a single patient from night to night. These simplistic single parameter systems are even less system is less suitable in the hospital where many confounding factors (such as sedation, etc.) may severely affect the performance of conventional auto titration system. Since most auto-titration system monitors their effectiveness through nasal signals their algorithms are limited by this wide variability of nasal resistance from patient to patient. Studies have shown that, while apneas can be detected, the detection of hypopneas by these devices is often poor. This becomes even more important for the detection of mild hypopneas, which can be very difficult to reliably detect (without an unacceptably high false positive rate) through a nasal signal alone. Indeed these milder hypopneas are more difficult characterize and not readily definable as a set of function of a set of predetermined rules for general application to all patients.

Figure 17:
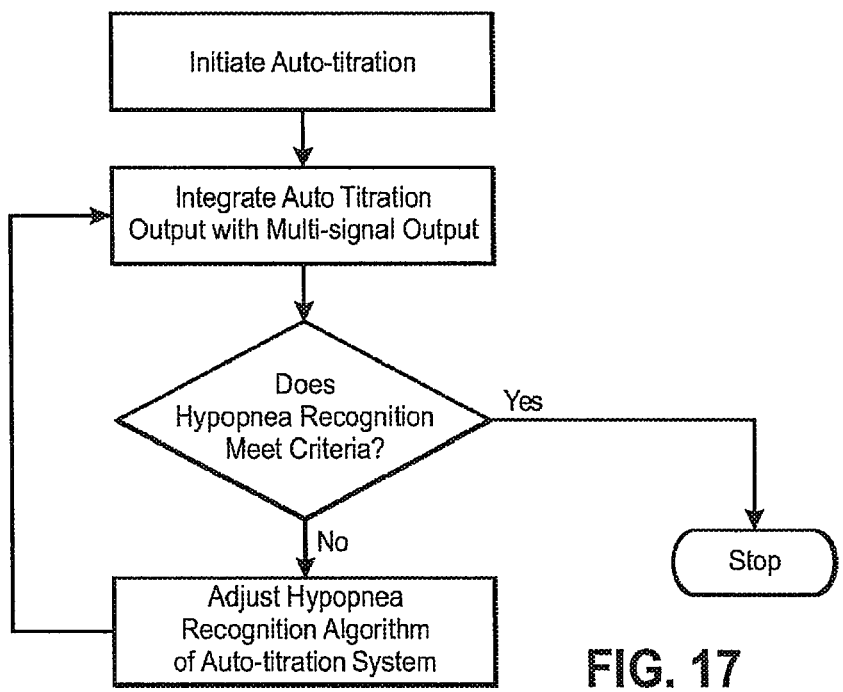
FIG. 17 shows a schematic of a system for customizing a CPAP auto-titration algorithm based on the analysis of multiple corresponding signals in accordance with present embodiments.

One process of applying the system of FIG. 8 to customize hypopnea recognition to match a given patients nasal output is represented in FIG. 17. The present disclosure includes an auto titration system, which adjusts its titration algorithm (which can be any of the conventional algorithms) based on the configurations of the multi-signal object, which can include oximetry, chest wall movement, or EEG data sets. With this system, for example, the initial titration algorithm is applied with the data set of CPAP pressure becoming part of the multi-signal object. The object time-series at the composite level is monitored for the presence of persistent clusters (especially clustered recovery objects or clustered EEG arousals). If these are identified then the region of the cluster occurrences is compared to the identified hypopnea region derived from the conventional method. If this region is as recognized as hypopneas then the pre-selected pressure for a given increment in titration is further incremented by 1-2 cm so that conventional titration occurs at higher-pressure levels and the process is repeated until all clusters are eliminated. (If EEG arousals worsen with this increase then the increment can be withdrawn). If on the other hand the algorithm did not recognize this region as a hypopnea the threshold criteria for a hypopnea is reduced until the clusters are eliminated (in some cases require a baseline fixed pressure of 2-3 or more cm.). FIG. 17 shows a CPAII auto-titration system which uses the multi-signal object dataset during one or more auto adjusting learning nights to customizes at least one of the treatment response to a given triggering threshold or the triggering threshold to a given treatment response. The application of a learning night can prevent inappropriate or unnecessary adjustments and can provide important information about treatment response while assuring that the basic algorithm itself is customized to the specific patient upon which it is applied. This is particularly useful in the hospital using hospital-based monitors where the monitor is coupled with the processor of the CPAP unit for the learning nights while in the hospital. In one embodiment, learning nights can be provided at home by connecting a primary processor for processing multiple signals with the processor of the CPAP unit for a few nights to optimize the algorithm for later use. In the hospital all of the components can be used to assure optimal titration, using the an objects based cluster analysis of simultaneous tracing of chest wall impedance and oximetry the titration can be adjusted to assure mitigation of all clusters, alternatively, if they are not mitigated by the titration then the nurse is warned that these clusters are refractory and to consider central apnea (particularly if the impedance movements during the apneas are equivocal or low). If for example, the patient's oxygen saturation falls (after adjusting for the delay) in response to an increase in pressure, the pressure can be withdrawn and the nurse warned that desaturation unresponsive to auto titration is occurring or bilevel ventilation can be automatically initiated. The self-customizing auto titration system can include a pressure delivery unit capable of auto adjusting either CPAP or BIPAP such that such a desaturation in response to CPAP can trigger the automatic application of BIPAP.

Figure 13:
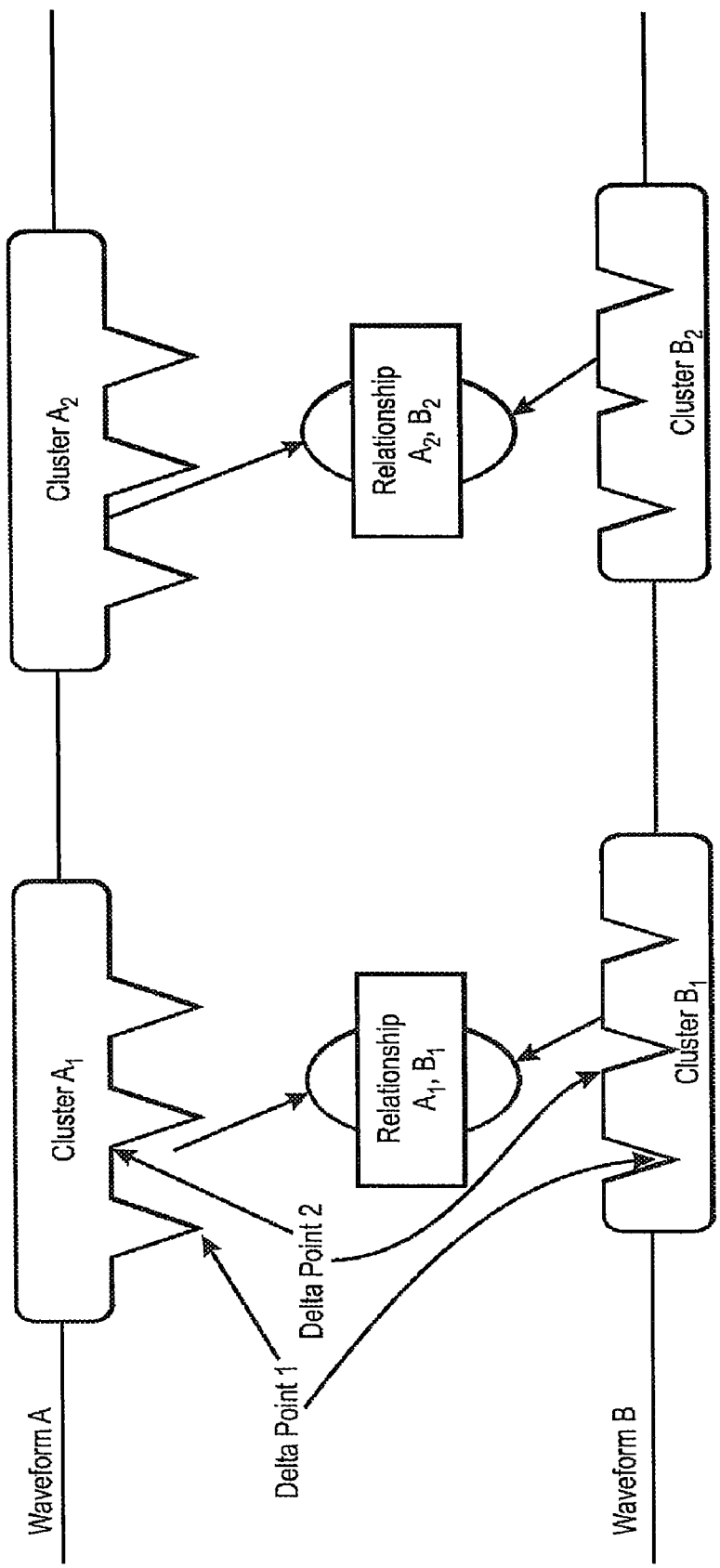
FIG. 13 shows a schematic object mapping at the composite level of corresponding signals of airflow and oxygen saturation in accordance with present embodiments.
Figure 14:
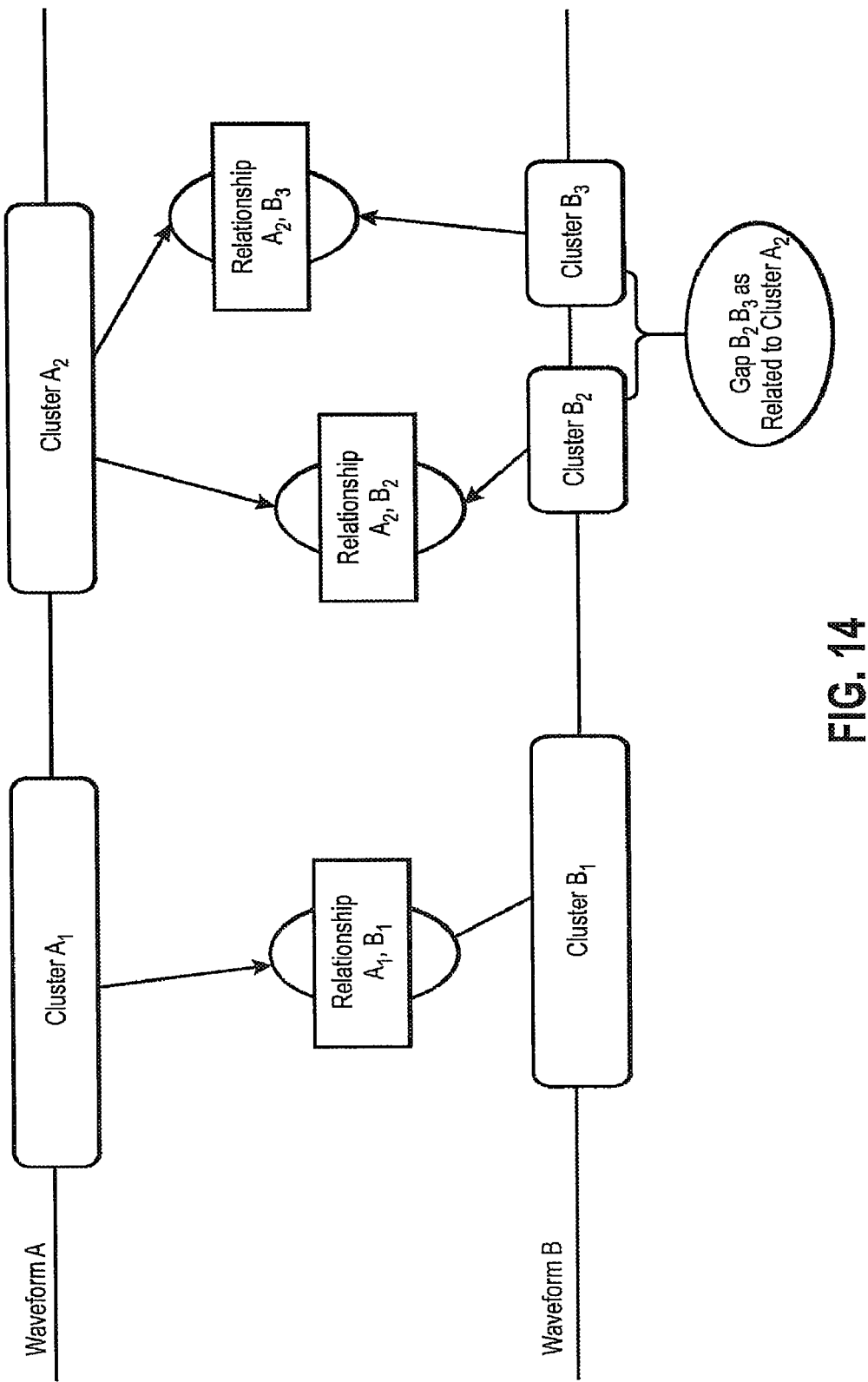
FIG. 14 shows a schematic object mapping at the composite level of two simultaneously measured parameters with a region of anticipated composite objects in accordance with present embodiments.
Figure 15:
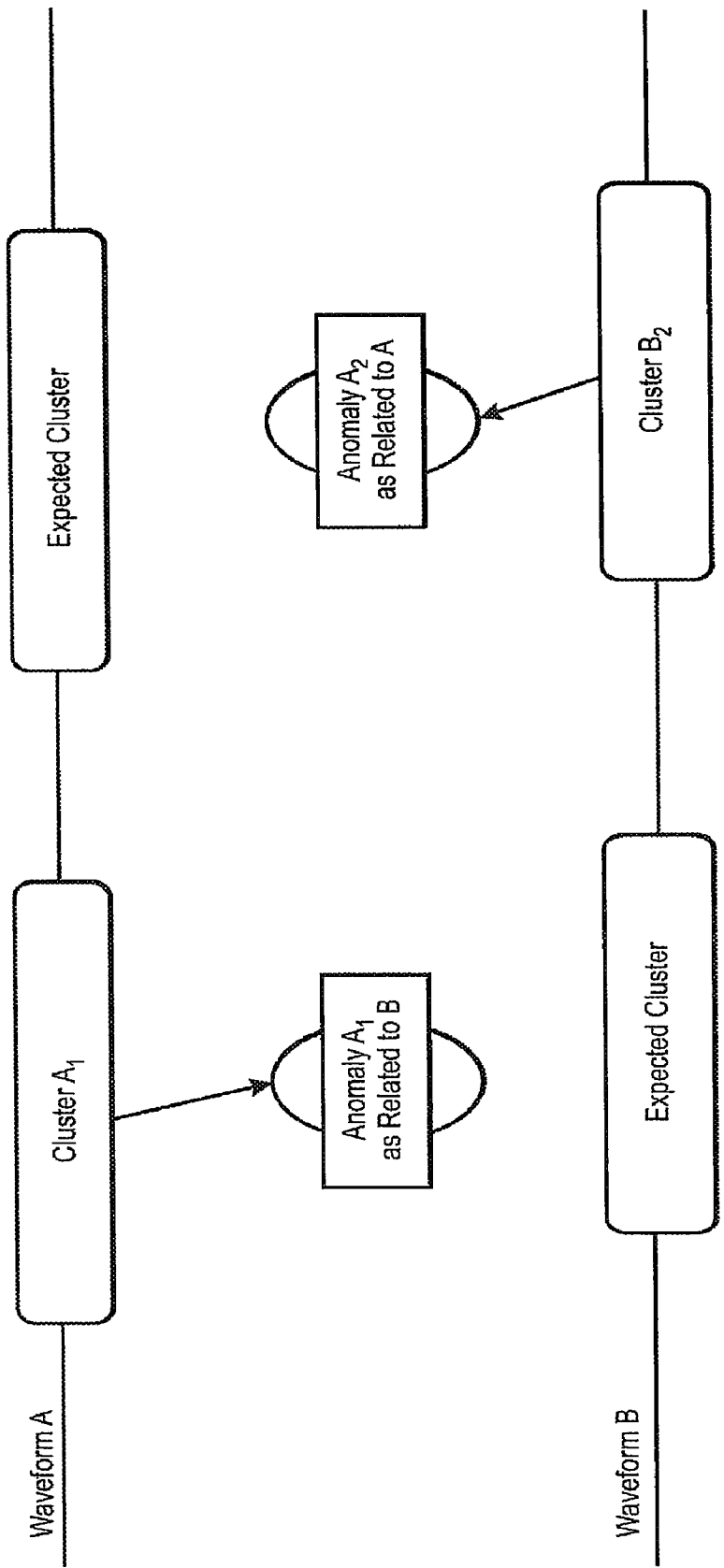
FIG. 15 shows a schematic object mapping and scoring at the composite level of two simultaneously measured parameters with the region of anticipated composite objects in accordance with present embodiments.

As discussed, according to the present disclosure, clusters of hypopneas can generally be reliably recognized utilizing with only a single parameter. However, when significant signal noise or reduced gain is present, the objects based system can combine matched clusters within a time-series of multi-signal objects in the presence of sub optimal signals by providing a scoring system for sequential objects. FIGS. 13, 14, and 15 show schematics of the basic cluster matching in situations wherein sub optimal signals may be present. The multi-signal objects defining the matched clusters of paired timed datasets of airflow and oximetry include a matched sequence of negative cycle objects in the airflow signal and corresponding negative cycle object in the oximetry signal. Each cycle object is defined by a set of coupled rise and fall objects meeting criteria and occurring within a predetermined interval of each other (as discussed previously). The occurrence of a cycle object in either dataset meeting all criteria is given a score of 1. The cycles are counted in sequence for each multi-signal cluster object. For the purpose of illustration, according to the present disclosure, the occurrence of a score of 3 in any one signal (meaning that a sequence of 3 cycles meeting criteria have occurred within a specified interval) provides sufficient evidence to identify a cluster object. When two simultaneous signals are processed, a total score of 4, derived from adding the number of cycles meeting criteria in each signal, is sufficient to indicate the presence of a cluster object. In this manner the cluster is continued by a sequential unbroken count greater than 3 with one signal, or greater than 4 with two signals. Once the presence of a cluster object has been established along the time-series, at any point along the cluster object the sequential count along one signal can be converted to a continuation of the sequential count along another signal allowing the cluster object to continue unbroken. The failure of the occurrence of a cycle meeting criteria within either signal within a specified interval (for example about 90-120 seconds, although other intervals may be used) breaks the cluster object. A new cluster object is again identified if the count again reaches the thresholds as noted above. It can be seen that this scoring method takes into account the fact that artifact often affects one signal and not another. Therefore if either signal alone provides a sufficient score, the presence of a cluster object is established. In addition, the effect of brief episodes of artifact affecting both signals is reduced by this scoring method. In this way, artifact, unless prolonged, may cause the cluster object to be broken but as soon as the artifact has reduced sufficiently in any one or more signals the process of scoring for a new cluster object will restart.

Another CPAP auto titration system according to the present disclosure includes a processor and at least one sensor for sensing a signal transmitted through the nose such as a pressure signal indicative of airflow, sound and/or impedance as is known in the art. An oximeter, which can be detachable or integrated into the CPAP unit, is connected with the processor. The processor detects hypoventilation using output from both the flow sensor and the oximeter, when the oximeter is attached, and in the embodiment with a detachable oximeter, when the oximeter is not attached the processor detects hypoventilation using the flow sensor without oximetry.

According to another aspect of the present disclosure, the multi-signal object time-series can be used for identifying pathophysiologic divergence. Pathophysiologic divergence can be defined at the fundamental, composite, or complex level. An example of divergence at the fundamental level is provided by the relationship between an airflow rise object (inspiration) and a fall object (expiration). Along a time-series of matched expiration and inspiration objects, the occurrence of a marked increase in amplitude of inspiration is commonly associated with an increase in the ratio of the absolute value of inspiration slope to the absolute value of the slope of exhalation. Should this value increase, this provides evidence suggesting pathophysiologic divergence. Alternatively, in one embodiment, the evaluation time period can be much longer. In one embodiment, the objects defining the data set of the first time interval are compared to the objects defining the data set of the second corresponding time interval. This comparison is performed in a similar manner to the aforementioned comparison of corresponding cluster objects noted supra. The specific parameters, which are compared, are parameters having known predictable physiologic linkages wherein a change of first physiologic parameter is known to induce a relatively predictable change in a second physiologic parameter. The second parameter is, therefore, a physiologically subordinate of the first parameter. As shown in FIG. 11, the first parameter can be a measure indicative of the timed volume of ventilation and the second parameter can be the timed arterial oxygen saturation. Here, as shown in FIG. 11, a progressive rise in minute ventilation is expected to produce a rise in oxygen saturation. The alveolar gas equation, the volume of dead space ventilation and the oxyhemoglobin disassociation curve predict the rise in oxygen saturation by known equations. However, according to one aspect of the present disclosure, it is not necessary to know the absolute predicted value of oxygen saturation rise for a given change in minute ventilation but rather the processor identifies and provides an output indicating whether or not an expected direction of change in the subordinate one parameter occurs in association with a given direction of change in the primary parameter. For example, with respect to arterial oxygen saturation and ventilation, it is the preferred purpose of one embodiment of the present disclosure to determine whether or not an expected direction and/or slope of change of oxygen saturation occur in association with a given direction and/or slope change in minute ventilation. The time course of the rise in ventilation of FIG. 11 is short however, as the time period lengthens the relationship is strengthened by the greater number of corresponding measurements and the greater measurement time. When minute ventilation slopes or trends upward over a sustained period, after the anticipated delay there would be an expected moderate upward change in oxygen saturation if the saturation is not already in the high range of 97-100%. On the other hand, if the oxygen saturation is falling during this period, this would suggest that the patient is experiencing a divergent pathophysiologic response which may warrant further investigation. Automatic recognition of falling or unchanged oxygen saturation in association with a rising minute ventilation can provide earlier warning of disease than is provided by the simple non-integrated monitoring and analysis of these two wave forms.

One of the advantages provided by the present disclosure is that it is not necessary to be exact with respect to the measurement of minute ventilation. Minute ventilation can be trended by conventional methods, without an absolute determination of the liters per minute for example, by plotting a measure of the amplitude and frequency of a nasal oral thermister or by the application of impedance electrodes on the chest, thereby monitoring the amplitude and frequency of tidal chest movement. Alternatively, conventional impedance or stretch sensitive belts around the chest and abdomen or other measures of chest stall and/or abdominal movement can be used to monitor tidal ventilation and then this can be multiplied times the tidal rate of breathing to provide a general index of the magnitude of the minute ventilation. In one embodiment, the minute ventilation are trended on a time data set over a five to thirty minute intervals along with the oxygen saturation.

In one embodiment, the monitoring system for identification of pathophysiologic divergence of timed output is shown in FIG. 8. As discussed previously, the monitor includes a microprocessor 10, the first sensor 20, a second sensor 25, and an output device 38 which can be a display or a printer, but preferably would include both. The processor 10 is programmed to generate a first timed waveform of the first parameter, derived from the first sensor 20, and a second timed waveform of second parameter, derived from the second sensor 25. Using the multi-signal processing system, described previously, the processor 10 compares the objects of the first timed output to the objects of the second timed output to identify unexpected divergence of the shape of the first timed output to the shape of the second timed output and particularly to recognize a divergence in directional relationship or polarity of one timed output of one parameter in relationship to another timed output of another related parameter. In one embodiment, this divergence comprises a fall in the slope of the oxygen saturation (for example, as defined by the recognition of a "decline object", as discussed previously) in relationship to a rise (referred to as a "rise object") in the slope of the corresponding minute ventilation. In another example, the processor integrates three signals to identify divergence. The processor identifies the relationship of other signals such as heart rate or R-to-R interval or a measure of the pulse magnitude (as the amplitude, slope of the upstroke, or area under the curve of the plethesmographic pulse). In particular, a rise object in minute ventilation may be identified in association with a decline object in oxygen saturation and a decline object in heart rate or pulse amplitude. These outputs can be plotted on a display 30 for further interpretation by a physician with the point of pathophysiologic divergence of one parameter in relationship to another parameter identified by a textural or other marker.

The identification of pathophysiologic divergence can result in significant false alarms if applied to the short time intervals used for rise and decline objects which are used for detection of cluster objects (and also the short averaging intervals for this purpose). In particular, if the identification of divergence is applied for short intervals, such as 1 to 2 minutes, a significant number of false episodes of divergence will be identified. One purpose of the present invention is to provide clear evidence of a trend in one measured parameter in relationship to a trend of another measured parameter so that the strong definitive evidence that divergence has indeed occurred. According to the present disclosure, this can be enhanced by the evaluation of the prolonged general shape or polarity of the signal so that it is considered preferable to identify divergence over segments of five to thirty minutes. The averaging of many composite objects to identify a rise object at the complex object level helps mitigate such false alarms. For this reason, the expected time course of a divergence type must be matched with the resolution (or averaging times) of the objects compared.

According to one aspect of the disclosure, to enhance the reliability of the analysis of the timed data set, the averaging interval, for this purpose, can be adjusted to avoid excessive triggering of the intermittent monitoring device. In one embodiment, the averaging interval is increased to between thirty and ninety seconds or only the analysis of complex objects can be specified. Alternative methods may be used to identify a rise and fall objects such as the application of line of best-fit formulas, as previously discussed. Elimination of outlier data points to define larger composite objects can also be applied as also previously discussed or by other methods. In this way the identification of a trend change, which evolves over a period of five to fifteen minutes, can be readily identified. The identification of divergence can produce a textual output, which can be maintained for a finite period until the secondary parameter corrects or a threshold period of time has elapsed. For example, if a rise in minute ventilation is identified over a predetermined interval period (such as about ten minutes) to define a rise object and a fall in oxygen saturation is identified over a corresponding period to define a fall object, the processor identifies the presence of divergence and can produce a textual output which can be provided on the bedside display or central processing display. This textual output can be maintained for a finite period, for example, one to two hours, unless the oxygen saturation returns to near its previous value, at which time the textual output may be withdrawn from the display.

In this way the presence of pathophysiologic divergence is readily identified, however, since divergence is defined by divergent rise and fall objects of corresponding physiologically linked parameters, its duration is necessarily limited since these slopes can not continue to diverge indefinitely. It is important to carry forward the identification of prior divergence in the patient's display for at least a limited period of time so that the nurse can be aware that this event has occurred. For example, a "fall object" identified in the secondary signal such as a fall in oxygen saturation from 95% to 90% over a period of ten minutes occurring in association with a rise object in the primary signal, such as, for example, a doubling of the amplitude of the airflow or chest wall impedance deflection over a period often minutes can produce an identification of pathophysiologic divergence which can be linked to the outputted saturation so that the display shows a saturation of 90% providing an associated textual statement "divergence-TIME". This identification of divergence can, over a period of time, be withdrawn from the display or it can be immediately withdrawn if the oxygen saturation corrects back close to 95%.

Figure 7:
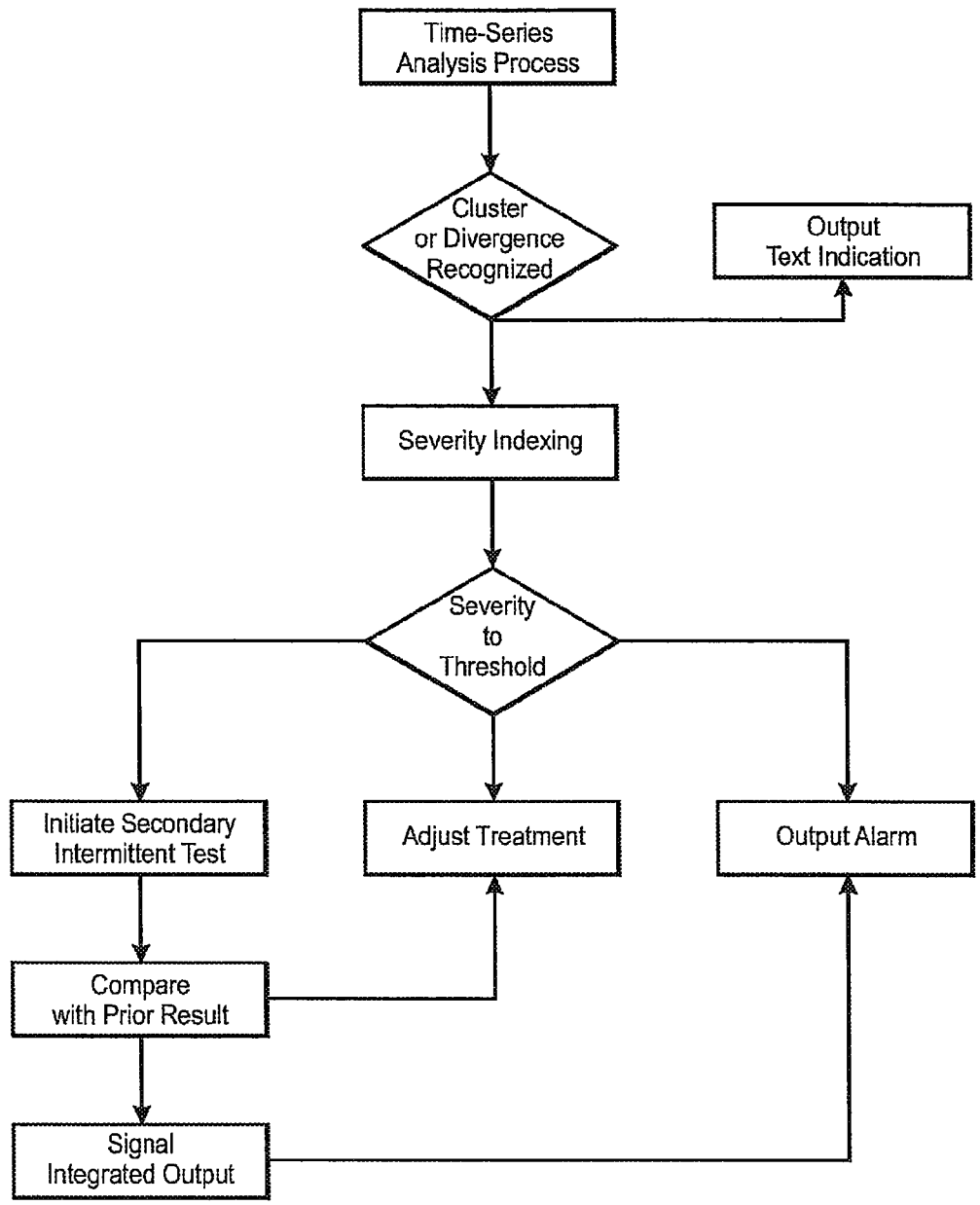
FIG. 7 shows a schematic of a processing system for outputting and/or taking action based on the analysis of the time-series processing in accordance with present embodiments.

FIG. 7 depicts a schematic of a processing system for outputting and/or taking action based on analysis of time-series processing in accordance with certain embodiments of the present technique.

The "Time-Series Analysis Process" block of FIG. 7 may represent a system component related to analyzing one or more time-series. In accordance with present embodiments, time-series analysis can be utilized to analyze multiple time-series of parameters generated by a patient in the assessment of disease. For example, a time-series of a patient's heart rate data may be analyzed. Other examples of parameters that may be analyzed include oxygen saturation, chest wall impedance, pulse rate, and blood pressure.

The system of FIG. 7 also includes a block titled "Cluster or Divergence Recognized," which may represent a system component configured to recognize a cluster or divergence of one or more time-series. Recognition of a cluster may be achieved by analyzing spatial and/or temporal relationships between different portions of a waveform. For example, a cluster may contain a high count of apneas with specified identifying features or patterns that occur within a short time interval along the waveform (such as 3 or more apneas within about 5-10 minutes). With regard to divergence, in accordance with present embodiments, a change in configuration of a multi-signal time-series can be used to trigger addition of one or more signals to the multi-signal time-series to identify whether or not physiological divergence is occurring with respect to the new, less frequently sampled signal.

By way of example, a processor in accordance with present embodiments may identify a significant rise in heart rate (e.g., a 25% rise and at least 15 beats per minute) over a period of 5 to 20 minutes. In view of such a rise, a monitor may automatically cause a measurement of blood pressure to be immediately taken. The processor may compare an output of the monitor to a previously recorded value and, if a significant fall in blood pressure (such as a fall in systolic of 15% and more) is identified in association with the identified rise in heart rate that triggered the test, a textual warning may be provided indicating that the patient is experiencing pathophysiologic divergence with respect to heart rate and blood pressure. The "Output Text Indication" block in FIG. 7 may represent a system component for providing such a warning.

In addition, the system may include features configured to index the severity of a recognized cluster or divergence, and make a severity to threshold determination. Such system components may be represented by the "Severity Indexing" and the "Severity to Threshold" blocks illustrated in FIG. 7. In accordance with present embodiments, the severity to threshold determination may result in an alarm. For example, mild clustering may result in outputting a single bar on a bar indicator, while a more severe clustering may result in generation of a larger warning. Such warnings may be represented by the "Output Alarm" box in FIG. 7.

The severity to threshold determination may also lead to adjusting a treatment, as indicated by the "Adjust Treatment" block. Further, the determination may also lead to initiation of a secondary intermittent test, as shown by the "Initiate Secondary Intermittent Test" block. The result of the secondary test may be compared to the prior results, as represented by the "Compare with Prior Result" block, which may also lead to a treatment adjustment. In addition, the results of the comparison may be combined into a signal integrated output, as illustrated by the "Signal Integrated Output" block, which may activate an alarm.

As discussed previously and as also illustrated in FIG. 8, in another embodiment of the present disclosure, a change in the configuration of the multi-signal time-series can be used to trigger the addition of one or more additional signals to the multi-signal time-series, such as a non-invasive blood pressure, to identify whether or not pathophysiologic divergence is occurring with respect to the new, less frequently sampled signal. For example, the trending rise in heart rate should not be generally associated with a fall in blood pressure. If, for example over a period of 5 to 20 minutes, a significant rise in heart rate (as for example a 25% rise and at least 15 beats per minute) is identified by the processor, according to the present disclosure, the monitor can automatically trigger the controller of a non-invasive blood pressure monitor to cause the measurement of blood pressure to be immediately taken. The output of the non-invasive blood pressure monitor is then compared by the processor to the previous value which was recorded from the blood pressure monitor and, if a significant fall in blood pressure (such as a fall in systolic of 15% and more) is identified in association with the identified rise in heart rate which triggered the test, a textual warning can be provided indicating that the patient is experiencing pathophysiologic divergence with respect to heart rate and blood pressure so that early action can be taken before either of these values reach life-threatening levels. According to another aspect of the disclosure, a timed dataset of the pulse rate is analyzed, if a significant change (for example a 30-50% increase in the rate or a 30-50% decrease in the interval or a 50-75% increase in the variability of the rate), then the blood pressure monitor can be triggered to determine if a significant change in blood pressure has occurred in relation to the change in pulse rate or the R to R interval.

This can be threshold adjusted. For instance, a significant rise in heart rate of 50% if lasting for a period of two and a half minutes can be used to trigger the intermittent monitor, whereas a more modest rise in heart rate of, for example, 25% may require a period of five or more minutes before the intermittent monitor is triggered.

In another embodiment, also represented in FIG. 8, identification by the bedside processor 10 of a sustained fall in oxygen saturation can be used to trigger an ex-vivo monitor 40 to automatically measure the arterial blood gas parameters. Alternatively, a significant rise in respiratory rate (for example, a 100% increase in respiratory rate for five minutes) can suffice as a trigger to automatically evaluate either the blood pressure or an ex-vivo monitor of arterial blood gasses.

There are vulnerabilities of certain qualitative indexes of minute ventilation in relationship to divergence, which the present disclosure serves to overcome to enhance the clinical applicability of the output. For example, a rise in the signal from chest wall impedance can be associated with a change in body position. Furthermore, a change in body position could result in a fall of oxygen saturation due to alteration in the level of ventilation, particularly in obese patients, such alterations can be associated with an alteration in the ventilation perfusion matching in patients with regional lung disease. Therefore, a change in body position could produce a false physiologic divergence of the signals when the multi-signal time-series includes chest wall impedance and oximetry. For this reason, according to the present disclosure, additional time-series components may be required, such as outputted by a position sensor, or alternatively, if this information is not available, a more significant fall in one parameter may be required in association with a more significant divergent rise in another. For example, a significant fall in oxygen saturation of, for example, 4-5% in association with a doubling of the product of the amplitude and frequency of the impedance monitor would provide strong evidence that this patient is experiencing significant pathophysiologic divergence and would be an indication for a textual output indicating that pathophysiologic divergence has occurred. The thresholds for defining divergence, according to the present disclosure, may be selectable by the physician or nurse. When the time-series output of a position monitor is incorporated into the system with a significant change in one or more parameter, which is temporarily related to a position change, it provides important additional information.

According to the present disclosure, the magnitude of pathophysiologic divergence can be provided on the central display 55 or bedside display 38. In some cases, as discussed previously, a mild degree of pathophysiologic divergence may not represent a significant change and the nurse may want to see, rather, an index of the degree of pathophysiologic divergence. A bar graph or other variable indicator, which can be readily observed such as the monitoring cubes of FIGS. 6a-6e, can provide this. In one embodiment the monitoring cube can be selectively time lapsed to observe the previous relational changes between parameters, or alternatively the animated object can be rotated and scaled to visually enhance the represented timed relationships and points of divergence.

In one embodiment, the multi-signal time-series output is placed into a format particularly useful for reviewing events preceding an arrest or for physician or nurse education. In this format the output controls an animation of multiple objects which, instead of being parts of a hexagon or cube are shaped into an animated schematic of the physiologic system being monitored. The animation moves over time and in response to the signals and in one embodiment the type of signals (or the reliability of such signals) determines which components of the schematic are "turned on" and visible. One example includes a multi-signal object defined by outputs of airflow, thoracic impedance, oximetry, and blood pressure rendering set of a connected set animation objects for the lungs, upper airway, lower airway, heart, and blood vessels which can be animated as;

Each inspiration causing an animated enlargement of the lungs tracking the inspiration slope, Each expiration causing an animated reduction in size of the lungs tracking the expiration slope, Each animated systolic beat of the heart tracks the QRS or upstroke of the oximetry output, The color of the blood in the arteries and left heart tracks the oxygen saturation, The diameter of the lower airway (a narrowing diameter can be highlighted in red) tracks the determination of obstruction by the slope ratio in situations of hyperventilation (as discussed previously), The patency of the upper airway (a narrowing or closure can be highlighted in red) tracks the determination of upper airway obstruction (as discussed previously).

The magnitude of an animated pressure gauge tracks the blood pressure.

This provides "physiologic animation" which can be monitored in real-time but will generally be derived and reviewed from the stored multi-signal objects at variable time scales. This is another example of an embodiment of the present disclosure providing a quickly, easily understood and dynamic animated output of a highly complex, interactive time-series derived form a patient. The animation can be reviewed at an increased time lapsed to speed through evolution of a given patients outputs or can be slowed or stopped to see the actual global physiologic state at the point of arrhythmia onset.

In another example of a more simple signal relationship indicator, a patient with a drop in oxygen saturation of 4% and a doubling of the product of the frequency and amplitude of the chest wall impedance tidal variation may have a single bar presented on the monitor, whereas, a patient with a 6% drop wherein the product of the impedance amplitude and frequency has tripled may have a double bar, and so on. This allows reduction in the occurrence of false alarms by providing a bar indicator of the degree of divergence which has occurred. A similar indicator can be provided for clustering, indicative of the severity of airway or ventilation instability. Since very mild clustering may simply represent the effect of moderate sedation, and not, therefore, represent a cause for great concern (although it is important to recognize that it is present). Such a clustering could be identified with a single bar, whereas more severe clustering would generate a larger warning and, it very severe, an auditory alarm. When the clustering becomes more severe and demonstrates greater levels of desaturation and/or shorter recovery intervals the bar can be doubled.

In another embodiment, which is particularly useful for neonates, the time-series of multi-signal objects is derived entirely from a pulse oximeter. Each object level for each signal and further a multi-signal object time-series of the oxygen saturation and pulse (as for example can be calculated below) is derived. This particular multi-signal time-series has specific utility for severity indexing of apnea of prematurity. The reason for this is that the diving reflex in neonates and infants is very strong and causes significant, cumulative bradycardia having a progressive down slope upon the cessation. In addition, the apnea is associated with significant hypoxemia, which also causes a rapid down slope due to low oxygen storage of these tiny infants. Even a few seconds of prolongation of apnea causes profound bradycardia because the fall in heart rate like that of the oxygen saturation does not have a reliable or nadir but rather falls throughout the apnea. These episodes of bradycardia cluster in a manner almost identical to that of the oxygen saturation, the pulse in the neonate being a direct subordinate to respiration.

In neonates, oxygen delivery to the brain is dependent both upon the arterial oxygen saturation and the cardiac output. Since bradycardia is associated with a significant fall in cardiac output, oxygen delivery to the neonatal brain is reduced both by the bradycardia and the fall in oxygen saturation. It is critical to have time-series measure, which relates to cumulative oxygen delivery (or the deficit thereof) both as a function of pulse and oxygen saturation. Although many indices can be derived within the scope of the present disclosure, the presently preferred index is given as the "Saturation Pulse". Although many calculations of this index are possible, in one embodiment, the index is calculated as:

$$SP = R(SO2-25)$$

Where:
SP is the saturation pulse in "% beats/sec.".
R is the instantaneous heart rate in beats per second, and
SO2 is the oxygen saturation of arterial blood in %.
The saturation-pulse is directly related to the brain oxygen delivery. The SPO2−25 is chosen because 25% approaches the limit of extractable oxygen in the neonatal brain. The index is preferably counted for each consecutive acquisition of saturation and pulse to produce a continuous time-series (which is an integral part of a multi-signal time-series of oxygen saturation and pulse). This index can be calculated for over the time interval of each apnea and each cluster to derive an apnea or cluster index of saturation-pulse during apnea and recovery in a manner analogous to that described in U.S. Pat. No. 6,223,064. This provides an enhanced tool for severity indexing of apnea of prematurity in infants. Both the duration and the absolute value of any decrement in saturation-pulse are relevant. If preferred the average maximum instantaneous, and cumulative deficit of the pulse saturation index can be calculated for each cluster (as by comparing to predicted normal or automatically calculated, non apnea related baseline values for a given patient).

In this way, according to the present disclosure, a general estimate of oxygen delivery over time to the infants brain is provided using a non-invasive pulse oximeter through the calculation of both oxygen saturation and pulse over an extended time-series deriving a cumulative deficit specifically within clusters of apneas to determine index of the total extent of global decrease in oxygen delivery to the brain during apnea clusters. The deficit can be calculated in relation to either the baseline saturation and pulse rate or predicted normals.

The processor can provide an output indicative of the pulse saturation index, which can include an alarm, or the processor can trigger an automatic stimulation mechanism to the neonate, which will arouse the neonate thereby aborting the apnea cluster. Stimulation can include a tactile stimulator such as a vibratory stimulator or other device, which preferably provides painless stimulation to the infant, thereby causing the infant to arouse and abort the apnea cluster.

In another embodiment of the system, the recognition of a particular configuration and/or order of objects can trigger the collection of additional data points of another parameter so that these new data points can be added to and compared with the original time-series to recognize or confirm an evolving pathophysiologic process. One application of this type of system is shown in FIG. 8 and illustrated further in FIG. 18. The time-series of pulse, oxygen saturation, and/or cardiac rhythm can be used to trigger an automatic evaluation of blood pressure by a non-invasive blood pressure device. The bedside processor 10, upon recognition of tachycardia by evaluation of the pulse or EKG tracing, automatically causes the controller of the secondary monitoring device 40 to initiate testing. The nurse is then immediately notified not only of the occurrence, but also is automatically provided with an indication of the hemodynamic significance of this arrhythmia. In this situation, for example, the occurrence of an arrhythmia lasting for at least twenty seconds can trigger the automatic comparison of the most recent blood pressure antecedent the arrhythmia and the subsequent blood pressure, which occurred after the initiation of the arrhythmia. The processor identifies the time of the initial blood pressure, which occurred prior to the point of onset of the arrhythmia, and the time of evaluation of the blood pressure after the onset of the arrhythmia and these are all provided in a textural output so that the nurse can immediately recognize the hemodynamic significance of the arrhythmia. Upon the development of a pulse less arrhythmia a printed output is triggered which provides a summary of the parameter values over a range (such as the 5-20 minutes) prior to the event as well as at the moment of the event. These are provided in a graphical format to be immediately available to the nurse and physician at the bedside during the resuscitation efforts so that the physician is immediately aware if hyperventilation, or oxygen desaturation preceded the arrhythmia (which can mean that alternative therapy is indicated).

According to another aspect of the disclosure, if the patient does not have a non-invasive blood pressure cuff monitor attached, but rather has only a pulse oximeter or an impedance based non-invasive cardiac output monitor and an electrocardiogram attached, then the multi-level time-series plethsmographic pulse objects can be used to help determine the hemodynamic significance of a given change in heart rate or the development of an arrhythmia. In this manner, the identification of significant change in the area under the curve associated with a significant rise in heart rate or the development of an arrhythmia can comprises a multi-signal object indicative of potential hemodynamic instability.

Figure 18:
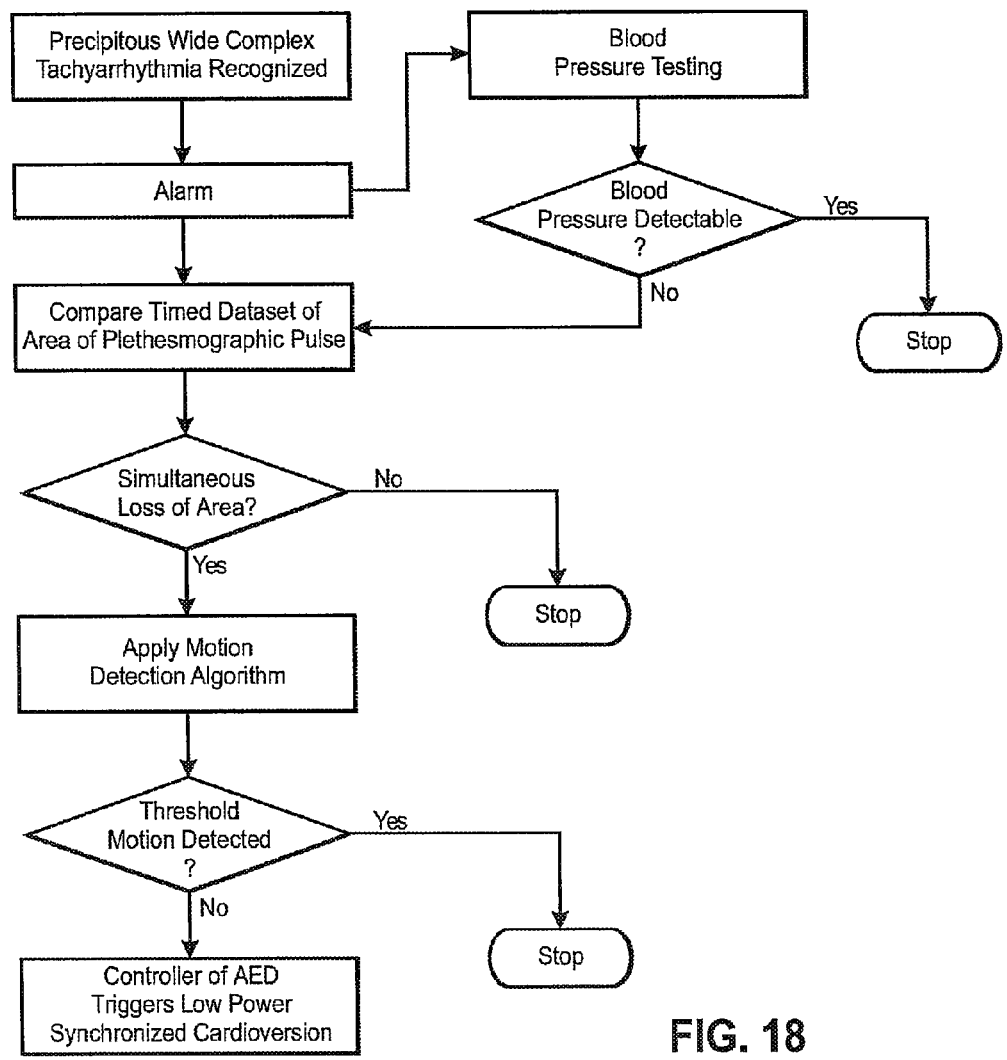
FIG. 18 shows a schematic system for comparing multiple signals and acting on the output of the comparison in accordance with present embodiments.

If the multi-signal object includes a new time-series of wide QRS complexes of this occurrence is compared to the area under the plethesmographic pulse to determine the presence of "pulseless" or "near pulseless" tachycardia. It is critical to identify early pulseless tachycardia (particularly ventricular tachycardia) since cardioversion of pulseless tachycardia may be more effective than the cardioversion of ventricular fibrillation. On the other hand, ventricular tachycardia associated with an effective pulse, in some situations, may not require cardioversion and may be treated medically. Timing in both situations is critical since myocardial lactic acidosis and irreversible intracellular changes rapidly develop and this reduces effective cardioversion. It is, therefore, very important to immediately recognize whether or not the significant precipitous increase in heart rate is associated with an effective pulse. The plethesmographic tracing of the oximeter can provide indication of the presence or absence of an effective pulse. However, displacement of the oximeter from the proper position on the digit can also result in loss of the plethesmographic tracing. For this reason, according to the present disclosure, the exact time in which the wide QRS complex time-series developed is identified and related to the time of the loss of the plethesmographic pulse. If the plethesmographic pulse is lost immediately upon occurrence of a sudden increase of heart rate (provided that the signal does not indicate displacement), this is nearly definitive evidence that this is a pulseless rhythm and requires cardioversion. The oxygen saturation and thoracic impedance portion of the multi-signal object is also considered relevant for the identification of the cause of arrhythmia. At this moment an automatic external cardioversion device can be triggered to convert the pulseless rhythm. In an alternative embodiment, as also shown in FIG. 18, a blood pressure monitor which can be a non-invasive blood pressure monitor integrated with the automatic defibrillator can be provided. Upon the recognition of a precipitous increase in heart rate, this event can trigger automatic non-invasive blood pressure evaluation. If the non-invasive blood pressure evaluation identifies the absence of significant blood pressure and pulse and this is confirmed by the absence of a plethesmographic pulse, then the processor can signal the controller of the automatic cardio version unit to apply and electrical shock to the patient based on these findings. It can be seen that multiple levels of discretionary analysis can be applied. The first being the identification of a precipitous development of a wide complex tachyarrhythmia in association with simultaneous loss of plethesmographic pulse which can trigger an automatic synchronized external cardio version before the patient develops ventricular fibrillation. The second requires confirmation by another secondary measurement such as loss of blood pressure, the lack of the anticipated cycle of chest impedance variation associated with normal cardiac output as with a continuous cardiac output monitor, or other indication.

It can be seen that even without the EKG time-series component object, an analysis of the multi-signal can be applied to compare the area under the curve of the plethesmographic pulse tracing generated by a pulse oximeter to a plot of peak-to-peak interval of the pulse tracings. The sudden decrease in the peak-to-peak interval or increase in pulse rate in association with a sudden decrease in the plethesmographic area is strong evidence that the patient has experienced a hemodynamically significant cardiac arrhythmia. In the alternative, a moderate and slowly trending upward increase in heart rate in association with a moderate and slowly trending downward plot of the area of the plethesmographic pulse would be consistent with intervascular volume depletion, or ineffective cardiac output resulting from significant sympathetic stimulation which is reducing the perfusion of the extremities as with as congestive heart failure. During such a slow evolution it would also be anticipated that the frequency of tidal respirations would increase.

In one embodiment, a motion detection algorithm can also be applied. The data set generated by the motion detection comprises a time-series component of the multi-signal object. If significant motion is identified at the time of the occurrence of both the tachyarrhythmia and the loss of the plethesmographic pulse and the motion continues to be present, then automatic external cardio version would not go forward and the device would simply provide a loud auditory and prominent visual alarm. The reason for this adjustment is that motion can in rare cases simulate the presence of a tachyarrhythmia and, further, such motion can result in loss of a detectable plethesmographic pulse. Rhythmic tapping of the chest wall lead of an electrocardiogram with the same finger to which the probe of the pulse oximeter is attached, theoretically, could simulate the occurrence of pulseless ventricular tachycardia. In addition, the development of a chronic seizure, which results in significant chest wall artifact, as well as rhythmic motion of the extremities could also simulate the development of pulseless tachycardia. For these reasons, according to the present invention, the presence of significant motion can be used to prevent the processor from signaling the controller of the automatic external cardio version device from shocking the patient.

Figure 16:
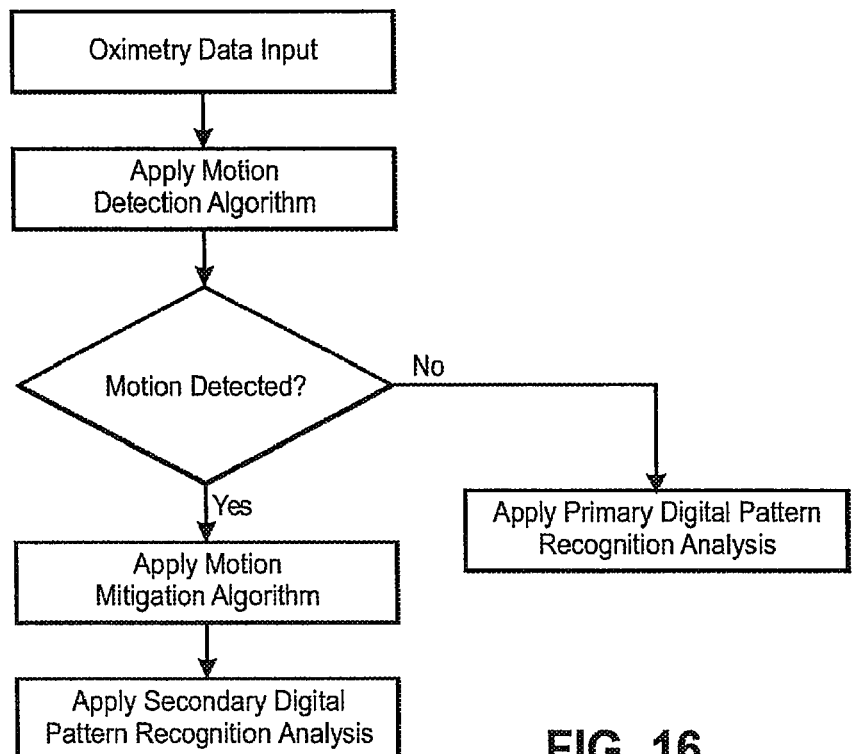
FIG. 16 shows a schematic of a system for automatically changing the processing analysis of subsequent time-series based on the analysis output of an earlier portion of the time-series in accordance with present embodiments.

According to another aspect of the present disclosure, a change in one or more time-series components of the multi-signal object can be used to change the processing algorithm of a time-series component of the multi-signal object. In an example, the recognition of airway instability is enhanced by improved fidelity of the timed waveform (as with pulse oximetry). FIG. 16 shows one method in accordance with present embodiments-of improving the general fidelity of the entire timed waveform of SPO2 for enhanced pattern cluster recognition in an environment where the patient, at times, has motion and, at other times, does not. It is optimal, for example, in monitoring oximetry for the probe to be placed on a portion of the patient, which is not associated with motion. However, in most cases, this is unrealistic and motion is commonly associated with routine clinical oximetry monitoring. It is well known that motion results in a fall in the saturation value, which is generated by the oximeter. Multiple theories for the cause of the fall have been promulgated. Several corporations, including Masimo, and Nellcor had developed algorithms, which can be used to mitigate the effect of motion on the accuracy of the output. However, such algorithms can include a significant amount of signal averaging, generally four seconds or more. This can result in significant smoothing of the waveform and reduces the fidelity of the waveform. Furthermore, it attenuates patterns of minor desaturations, which can be indicative of airway instability, and clusters of hypopneas associated with variations in airway resistance. As discussed in the aforementioned patents and patent application, even minor desaturations when occurring in clusters can be strong evidence for airway or ventilation instability and it is important to recognize such desaturations. Unfortunately, averaging intervals, especially those exceeding four seconds or more can result in attenuation of these desaturations and, therefore, hide these clusters so that the airway instability may not be recognized. However, motion itself results in artifact, which can simulate desaturations. Although such artifact is not expected to occur in typical cluster pattern, the presence of motion artifacts significantly reduces the value of the signal as an index of oxygen saturation and airway instability. The present disclosure thereby provides for more optimal continuous fidelity of the waveform through both motion and non-motion states. As illustrated in FIG. 16, when the motion time-series output suggests that substantial motion is not present, such as deep sleep or sedation, wherein the extremity is not moving, long averaging smoothing algorithms or motion mitigation algorithms are not applied to the oxygen saturation and plethesmographic pulse time-series. In the alternative, if the series indicates motion then these motion mitigation algorithms are applied. The variable application of averaging based on identification of the absence or presence of motion provides optimal fidelity of the waveform for monitoring airway instability.

Those skilled in the art will recognize that, the information provided from the data and analysis generated from the above-described system can form the basis for other hardware and/or software systems and has wide potential utility. Devices and/or software can provide input to or act as a consumer of the physiologic signal processing system of the present invention's data and analysis.

The following are examples of ways that the present physiologic signal processing system can interact with other hardware or software systems:

1. Software systems can produce data in the form of a waveform that can be consumed by the physiologic signal processing system.
2. Embedded systems in hardware devices can produce a real-time stream of data to be consumed by the physiologic signal processing system.
3. Software systems can access the physiologic signal processing system representations of populations of patients for statistical analysis.
4. Software systems can access the physiologic signal processing system for conditions requiring hardware responses (e.g. increased pressure in a CPAP device), signal the necessary adjustment and then analyze the resulting physiological response through continuous reading of the physiologic signal processing system data and analysis.

It is anticipated that the physiologic signal processing system will be used in these and many other ways. To facilitate this anticipated extension through related hardware and software systems the present system will provide an application program interface (API). This API can be provided through extendable source code objects, programmable components and/or a set of services. Access can be tightly coupled through software language mechanisms (e.g. a set of C++ modules or Java classes) or proprietary operating system protocols (e.g. Microsoft's DCOM, OMG's CORBA or the Sun Java Platform) or can be loosely coupled through industry standard non-proprietary protocols that provide real-time discovery and invocation (e.g. SOAP [Simple Object Access Protocol] or WSDL [Web Service Definition Language]).

In one embodiment, the physiologic signal processing system with the API as defined becomes a set of programmable objects providing a feature-rich development and operating environment for future software creation and hardware integration.

Although embodiments have been described, which relate to the processing of physiologic signals, it is also critical to recognize the present streaming parallel objects based data organization and processing method can be used to order and analyze a wide range of dynamic patterns of interactions across a wide range of corresponding signals and data sets in many environments. The invention is especially applicable to the monitoring of the variations or changes to a physical system, biologic system, or machine subjected to a specific process or group of processes over a specific time interval.

The present disclosure provides a new general platform for the organization and analysis of a very wide range of datasets during hospitalization or a surgical procedure. For example, in addition to the time-series of the monitored signals parameters, which may be sampled at a wide range (for example between about 500 hertz and 0.01 hertz), previously noted, the cylindrical data matrix can include a plurality of time-series of laboratory data, which may be sampled on a daily basis or only once during the hospitalization. These data points or time-series are stored as objects and can be included in the analysis. These objects can include, for example the results of an echocardiogram wherein a timed value ejection fraction of the left ventricle is provided as an object in the matrix for comparison with other relationships. In application, the presence of a low ejection fraction object along the matrix with a particular dynamic cyclic variation relationship between airflow and oxygen saturation time-series can, for example, provide strong evidence of periodic breathing secondary to congestive heart failure and this identified relationship can be provided for the healthcare worker in a textual output. In another example the medications are included in data matrix. For example in a patient receiving digoxin and furosemide (a diuretic) the daily serum potassium time-series is compared to a time-series indicative of the number and severity of ventricular arrhythmias such as premature ventricular contractions. A fall in the slope of the potassium time-series in association with a rise in slope of such an arrhythmia indication time-series could for example produce an output such as "increased PVCs—possibly secondary to falling potassium, consider checking digoxin level". In another example a first time-series of the total carbon dioxide level and a second time-series of the anion gap can be included in the general streaming object matrix and compared to the time-series of airflow. If a rise in the slope or absolute values of the airflow is identified with a fall in the slope or absolute value along the total carbon-dioxide time-series and a rise the slope or absolute values alone the anion gap time-series, the processor can provide an automatic identification that the airflow is rising and that the cause of a rise in airflow may be secondary to the development of a potentially life threatening acidosis, providing an output such as "hyperventilation—possibly due to evolving anion gap acidosis". In another example, the daily weight or net fluid balance is included with the total carbon dioxide and anion gap in the cylindrical data matrix. The identification of a fall in slope of airflow or absolute value along the associated with a fall in slope of the oxygen saturation, and a fall in slope of the fluid balance and weight can generated a output such as "possible hypoventilation-consider contraction alkalosis".

Alternatively with a matrix made up of the same parameters, a rise in the slope or absolute values of the airflow time-series and a rise in the pulse time-series may be recognized in comparison with a fall in the time-series of the total carbon dioxide, a flat slope of the time-series of the anion gap, and a rise in the slope or absolute values of the fluid balance time-series, confirmed by a trending rise in slope of the weight time-series, and a notification can be provided as "hyperventilation—potentially secondary to expansion acidosis or congestive heart failure". In one embodiment the cylindrical data matrix becomes the platform upon which substantially all relevant data derived during a hospitalization is stored and processed for discretionary and automatic comparison. Initial input values, which can be historical input, can also be included to set the initial state of the data matrix. For example, if the patient is known to have a history congestive heart failure, and that is inputted as an initial data point at the start of the matrix and that particular conformation in the initial matrix is considered in the analysis. The data matrix provides a powerful tool to compare the onset of dynamic changes in parameters with any external force acting on the organism whether this force is pharmacological, a procedure, related to fluid balance, or even simple transportation to other departments for testing. In one embodiment, as shown in FIG. 1b, a time-series of action applied to the patient is included called an "exogenous action time-series". This time-series includes a set of streaming objects indicating the actions being applied to the patient throughout the hospitalization. In this example, within the exogenous action time-series a time-series component indicative of dynamic occurrence of a particular invasive procedure, such as the performance of bronchoscopy, is included. This "bronchoscopic procedure object" may, for example, comprise a time-series component along the exogenous action time-series of 15 minutes within the total matrix derived from the hospitalization. The dynamic relationships of the parameters along the matrix are compared with the onset of the procedure (which comprising an object onset), dynamic patterns of interaction evolving subsequent to the onset of the procedure can be identified and the temporal relationship to the procedure object identified and outputted in a similar manner as has been described above for other objects. The dynamic patterns of interaction can be interpreted with consideration of the type of procedure applied. For example, after a 15 minute time-series associated with a bronchoscopic procedure, the occurrence of a progressive increase in slope of the airflow time-series associated with a significant decrease in the slope of the inspiration to expiration slope ratio time-series suggests the development of bronchospasm secondary to the bronchoscopy and can initiate an output such as "hyperventilation post-bronchoscopy with decreased I:E—consider bronchoscopy". A larger surgical procedure comprises a longer cylindrical data matrix and this can comprise a perioperative matrix, which can include the portion of time beginning with the administration of the first preoperative medication so that dynamic patterns of interaction are compared with consideration of the perioperative period as a global time-series object within the matrix, with the preoperative period, the operative period, and the post operative period representing time-series segment of the matrix within the total hospital matrix. Using this objects based relational approach a "dynamic pattern" of interaction occurring within this procedure related data stream or subsequent to it can be easily recognized and temporally correlated with the procedure so that the dynamic relationships between a procedure and plurality of monitored time-series outputs and/or laboratory data are stored, analyzed, and outputted. In another example, the continuous or intermittent infusion of a pharmaceutical such as a sedative, narcotic, or inotropic drug comprises a time-series which has as one of its timed characteristics the dose administered. This new time-series is added to the cylindrical matrix and the dynamic relationships between monitored signals and laboratory data is compared. For example, after the initiation of Dobutamine (an inotropic drug) the occurrence of a rising slope of pulse rate or a risings slope of premature ventricular contraction frequency, or the occurrence of an object of non-sustained ventricular tachycardia, can be recognized in relation to onset the time-series of medication infusion or a particular rise in the slope or absolute value of the of the dose of this medication. In another example the occurrence of a dynamic clustering of apneas such as those presented in FIGS. 10, 11, and 5c in relation to a rise in slope, or a particular absolute value, of the time-series of the sedative infusion can he identified and the pump can be automatically locked out to prevent further infusion and an output such as "Caution—pattern suggestive of mild upper airway instability at dose of 1 mg Versed." If in this example the nurse increases the doe to 2 mg and the pattern shows an increase in severity an output such as "Pattern suggestive of moderated upper airway instability at dose of 2 mg/hr. of Versed-dose locked out". To maintain Versed dose at the 2 mg, level in this patient the nurse or physician would have to override the lockout. Upon an override the processor then tracks the severity of the clusters and if the clusters reach a additional severity threshold then an output such as "Severe upper airway instability—Versed locked out".

The anticipated range of time-series for incorporation into the cylindrical relational matrix of streaming objects include: multiple pharmaceutical time-series, exogenous action time-series, monitored signal time-series (which can include virtually any monitored parameter or its derivative), fluid balance, weight, and temperature time-series, and time-series or single timed data points of laboratory values (including chemistry, hematology, drug level monitoring, and procedure based outputs (such as echocardiogram and pulmonary function test outputs). Interpreted radiology results may also be incorporated as data points and once the digital signal for such testing can be reasonably summarized to produce a time-series, which reliably reflects a trend (such as the degree of pulmonary congestion), such outputs can also be include in the data matrix as time-series for comparison with, for example, the net fluid balance and weight time-series. An additional time-series can be provided by nursing input, for example a time-series of the pain index, or Ramsey Scale based level of sedation. This time-series can be correlated with other monitored indices of sedation or anesthesia as is known in the art.

The cylindrical matrix of processed, analyzed, and objectified data provides an optimal new tool for the purpose of doing business to determine, much more exactly, the dynamic factors, occurrences, and patterns of relationships, which increase expense in any timed process. In the example of the hospital system discussed supra, the expense data is structured as a time-series of objects with the data point value represented by the total expense at each point. Expense values can be linked and or derived from certain procedures or laboratory tests, for example the time-series of the hemoglobin can be associated with a corresponding time-series of the calculated expense for that test. In the preferred embodiment the plurality of time-series of expense for each monitored laboratory tests are combined to produce a global expense time-series. Individual time-series for the expense of each class of exogenous actions (such as pharmaceutical, and procedural time-series) is also provided and can then be combined to form one global expense time-series. This is incorporated into the cylindrical data matrix to provide discretionary comparison with dynamic expense variables and dynamic patterns of relationships of other variables. This allows the hospital to determine the immediate expense related to the occurrence of an episode of ventricular fibrillation. This expense can be correlated with, for example, the timeliness of treatment, the application of different technologies, or the presence of a specific dynamic pattern of interaction of the signals. In other words the immediate cost, and resources expended over, for example, the 24 hours following the episode of ventricular fibrillation, can be compared with the true behavior and duration of the pathophysiologic components relating the ventricular fibrillation episode.

In a further example, consider a patient monitored with an embodiment of the present disclosure deriving a cylindrical data matrix comprised of streaming and overlapping objects of airflow, chest wall impedance, EKG, oximetry, and global expense. The occurrence of the procedure for insertion of the central line represents an object (which need not have a variable value) along a segment of the cylinder. If the patient develops a pneumothorax the processor can early identify and warn of the development of pathophysiologic divergence with respect to the airflow (and/or chest wall impedance) and the oxygen saturation (and/or pulse). In addition to earlier recognition, the expense related to this complication, the timeliness of intervention, the magnitude of pathophysiologic perturbation due to the complication, and the resources expended to correct the complication can all be readily determined using the processor method and data structure of the present disclosure.

Many other additional new component cylinders may be added to the matrix. During the implementation of embodiments of the present disclosure, it is anticipated that many subtle relationships between the many components will become evident to those skilled in the art and these are included within the scope of this disclosure. Those skilled in the art will recognize that various changes and modifications can be made without departing from the disclosure. While the present embodiments have been described in connection with what is presently considered to be the most practical and preferred embodiments, it is to be understood that the disclosure is not to be limited to the disclosed embodiments, but on the contrary, is intended to cover various modifications and equivalent arrangements included within the spirit and scope of the appended claims.

What is claimed is:

1. A microprocessor system for evaluation of a patient, the system comprising:
monitor having a first and a second sensor, wherein the monitor is positioned for positioning adjacent said patient, the first sensor obtaining first data associated a first physiologic parameter and the second sensor obtaining second data associated with a second physiologic parameter, wherein the second physiologic parameter comprises a measure of arterial oxygenation;
a processor in communication with the monitor, the processor programmed to:
receive the first data associated with the first physiologic parameter from the monitor;
receive the second data associated with the second physiologic parameter from the monitor;
produce a first timed waveform based on the first physiologic parameter of a patient;
produce a second timed waveform based on the second physiologic parameter which is generally subordinate to said first physiologic parameter, so that said second physiologic parameter normally changes in response to changes in said first physiologic parameters;

identify pathophysiologic divergence of at least one of said first and second physiologic parameters in relationship to the other of said physiologic parameters, the pathophysiologic divergence comprising a change that is both unexpected and pathological;

automatically determine a possible dysfunction associated with the change; and output an indication of the dysfunction.

2. The system, as in claim 1, wherein the at least one processor is further programmed to: a) calculate an index of said pathophysiologic divergence and, b) provide an indication based on said index.

3. The system of claim 1, wherein said first physiologic parameter comprises at least one of an indication and measure of a magnitude of timed ventilation of the patient.

4. The system of claim 3, wherein said first physiologic parameters includes at least one of an amplitude and a frequency of variation in chest wall impedance.

5. The system of claim 3, wherein said first physiologic parameter includes at least one of an amplitude and a frequency of variation in nasal pressure.

6. The system of claim 3, wherein the first physiologic parameter is a measure of timed volume of at least one gaseous component of ventilation.

7. The system of claim 1, wherein said first physiologic parameter is at least one of a measure and an indication of carbon dioxide.

8. A method of monitoring a patient comprising:

a processor monitoring a patient with a first sensor to produce a first timed waveform of a first physiologic parameter and a second sensor to produce a second timed waveform of a second physiologic parameter, wherein the second physiologic parameter comprises a measure of arterial oxygenation;

the processor transforming the sensed physiological inputs into visual data, wherein the visual data representing a first and second waveform, and wherein the second physiologic parameter being physiologically subordinate to said first physiologic parameters;

the processor identifying a pattern indicative of pathophysiologic divergence of at least one of the first waveform in relation to the second waveform, the pathophysiologic divergence comprising a change that is both unexpected and pathological; and the processor automatically determining a possible dysfunction associated with the change; and the processor outputting an indication of the possible dysfunction.

9. The method of claim 8, wherein said first timed waveform is defined by a time interval of 5 to 20 minutes.

10. The method of claim 8 wherein said first and second timed waveforms are derived from airflow and pulse oximetry measurements.

11. The method of claim 8, comprising controlling a diagnostic and/or treatment device with a secondary processor programmed to respond to the output of said processor.

12. The method of claim 11, comprising adjusting a program of said secondary processor with said processor.

13. The method of claim 11, comprising recognizing hypopneas with said secondary processor and providing airflow with said treatment device, said processor adjusting a program of said secondary processor based on said pattern.

14. The method of claim 11 wherein said treatment device is an automatic defibrillator.

15. The method of claim 11, comprising mounting said secondary processor with said treatment and/or diagnostic device, and wherein said processor is detachable from a connection with said secondary processor.

16. The method of claim 11, comprising monitoring and analyzing a plurality of different patient related signals including electrocardiographic signals with said processor.

17. The method of claim 11, wherein said processor is a polysomnography monitor, and comprising monitoring a plurality of different signals including encephalographic signals with said processor.

18. A tangible, non-transitory computer readable medium having stored thereon computer-executable instructions for performing a method for monitoring a patient, the instructions comprising:

instructions to receive a first timed waveform from a first sensor that monitors a patient, wherein the first timed waveform measures a first physiologic parameter;

instructions to receive a second timed waveform from a second sensor that monitors the patient, wherein the second timed waveform measures a second physiologic parameter, the second physiologic parameter being physiologically subordinate to said first physiologic parameter, and wherein said second physiologic parameter comprises a measure of arterial oxygenation;

instructions to identify a pattern indicative of a pathophysiologic divergence of the first and second timed waveforms, the pathophysiologic divergence comprising an unexpected change;

instructions to determine automatically a possible dysfunction associated with the change; and instructions to output an indication of the possible dysfunction.

* * * * *

UNITED STATES PATENT AND TRADEMARK OFFICE
CERTIFICATE OF CORRECTION

| | | |
|---|---|---|
| PATENT NO. | : 8,241,213 B2 | Page 1 of 1 |
| APPLICATION NO. | : 12/839177 | |
| DATED | : August 14, 2012 | |
| INVENTOR(S) | : Lawrence A. Lynn and Eric N. Lynn | |

It is certified that error appears in the above-identified patent and that said Letters Patent is hereby corrected as shown below:

In the Claims:

In Claim 1:

Column 54, line 51, should be corrected to read as follows:

--monitor is positioned adjacent the--

Column 55, line 2, should be corrected to read as follows:

--to changes in said first physiologic parameter;--

In Claim 4:

Column 55, line 19, should be corrected to read as follows:

--parameter includes at least one of an amplitude and a fre- --

In Claim 8:

Column 55, line 42, should be corrected to read as follows:

--nate to said first physiologic parameter;--

Signed and Sealed this
Twenty-eighth Day of May, 2013

Teresa Stanek Rea
*Acting Director of the United States Patent and Trademark Office*